US009745350B2

(12) United States Patent
Malm et al.

(10) Patent No.: US 9,745,350 B2
(45) Date of Patent: Aug. 29, 2017

(54) HER3 BINDING POLYPEPTIDES

(71) Applicant: AFFIBODY AB, Solna (SE)

(72) Inventors: Magdalena Malm, Stockholm (SE); John Löfblom, Huddinge (SE); Stefan Ståhl, Stockholm (SE)

(73) Assignee: AFFIBODY AB, Solna (SE)

( * ) Notice: Subject to any disclaimer, the term of this patent is extended or adjusted under 35 U.S.C. 154(b) by 0 days.

(21) Appl. No.: 14/431,336

(22) PCT Filed: Oct. 3, 2013

(86) PCT No.: PCT/EP2013/070605
§ 371 (c)(1),
(2) Date: Mar. 26, 2015

(87) PCT Pub. No.: WO2014/053586
PCT Pub. Date: Apr. 10, 2014

(65) Prior Publication Data
US 2015/0252079 A1  Sep. 10, 2015

Related U.S. Application Data

(60) Provisional application No. 61/753,963, filed on Jan. 18, 2013, provisional application No. 61/710,051, filed on Oct. 5, 2012.

(30) Foreign Application Priority Data

Oct. 5, 2012 (EP) .................................... 12187457
Jan. 18, 2013 (EP) .................................... 13151882

(51) Int. Cl.
*A61K 51/08* (2006.01)
*G01N 33/574* (2006.01)
*C07K 14/00* (2006.01)
*C07K 14/71* (2006.01)

(52) U.S. Cl.
CPC ............ *C07K 14/00* (2013.01); *A61K 51/088* (2013.01); *C07K 14/71* (2013.01); *G01N 33/57492* (2013.01); *G01N 2333/71* (2013.01)

(58) Field of Classification Search
None
See application file for complete search history.

(56) References Cited

FOREIGN PATENT DOCUMENTS

| EP | 2072525 A1 | 6/2009 |
| WO | 2005003156 A1 | 1/2005 |
| WO | 2007065635 A1 | 6/2007 |
| WO | 2008100624 | 8/2008 |
| WO | 2009019117 A1 | 2/2009 |
| WO | 2011056124 A1 | 5/2011 |

OTHER PUBLICATIONS

International Search Report of the International Searching Authority for International Patent Application No. PCT/EP2013/070805; International Filing Date: Oct. 3, 2013; Date of Mailing: Nov. 12, 2013; 4 Pages.
International Preliminary Report on Patentability and Written Opinion of the International Searching Authority for International Patent Application No. PCT/EP2013/070605; International Filing Date: Oct. 3, 2015 ; Date of Mailing: Apr. 16, 2015; 10 Pages.
Baker et al.; "Conversion of a T Cell Antagonist into an Agonist by Repairing a Defect in the TCR/Prptide/MHC Interface: Implications for TCR Signaling", Immunity, vol. 13, p. 475-484, 2000.
Burgess et al., "Possible Dissociation of hte Heparin-binding and mitogenic Activities of Heparin-binding (Acidic Fibroblast) Growth Factor-1 from Its Receptor-binding Activities by Site-directed Mutagenesis of a Single Lysine Residue" Journal of Cell Bi.
Ekerljung et al., "Effects of HER2-Binding Affibody Molecules on Intracellular Signaling Pathways" TurmorBiology, 2006, 27, pp. 201-210.
Friedman et al. "Directed Evolution to Low Nanomolar Affinity of a Tumor-Targeting Epidermal Growth Factor Receptor-Binding Affibody Molecule" Journal of Molecular Biology (2008), pp. 1388-1402, vol. 376.
Friedman et al., "Engineering and Characterization of a Bispecific HER x EGFR-binding Affibody Molecule", Biotechnol. Appl. Biochem. (2009) 54, pp. 121-131.
Gronwall et al. "Engineered Affinity Proteins—Generation and Applications" Journal of Biotechnology (2009, pp. 254-269, vol. 140.
Horan et al. Binding of Neu Differentiation Factor with the Extracellular Domain of Her2 and Her3* ; The Journal of Biological Chemistry, vol. 270, No. 41. p. 24604-24608.
Huang et al.; "Transformaing Growth Factor β Peptide Antagonists and their Conversion to Partial Agonists", Journal of Biological Chemistry, vol. 272, No. 43, p. 27155-27159, 1997.
Ju et al., "Conversion of the Interleukin 1 Receptor Antagonist into an Agonist by Site-Specific Mutagenesis" Proc. Natl. Acad. Sci, vol. 88, (1991), pp. 2658-2662.
Kontermann, "Strategies to Extend Plasma Half-Lives of Recombinant Antibodies" Biodrugs, 2009, 23 (2); pp. 93-109.
Kronqvist et al. "Combining phage and staphylococcal surface display for generation of ErbB3-specific Affibody molecules", Protein Engineering, Design & Selection vol. 24, No. 4, p. 385-392, published online Dec. 21, 2010.
Mendoza et al..; "Anti-tumor chemotherapy utilizing peptides-based approches-apoptotic pathways, kinases, and proteasomes as targets", Arch. Immunol Ther. Exp., vol. 53, p. 47-60, 2005.
Montrose-Rafizadeh et al.; High Potency Antagonists of the Pancreatic Glucagon-like Peptide-1 Receptor; Journal of Biological Chemistry, vol. 272, p. 21201-21206, 1997.
Nord et al. "A Combinatorial Library of an Alpha-Helical Bacterial Receptor Domain" Protein Engineering (1995), pp. 601-608, vol. 8, No. 6.

(Continued)

*Primary Examiner* — Karen Canella
(74) *Attorney, Agent, or Firm* — Cantor Colburn LLP

(57) ABSTRACT

The present disclosure relates to polypeptides which bind to human epidermal growth factor receptor 3 (HER3) and to use of such polypeptides in imaging and therapy. The disclosure provides an HER3 binding polypeptide comprising a HER3 binding motif, which motif consists of the amino acid sequence $EKYX_4AYX_7EIW X_{11}LPNLTX_{17}X_{18}QX_{20}$ $AAFIGX_{26}$ $LX_{28}D$ (SEQ ID NO:110).

24 Claims, 17 Drawing Sheets

(56) References Cited

OTHER PUBLICATIONS

Orlova et al. "Affibody Molecules for Molecular Imaging and Therapy for Cancer" Cancer Biotherapy and Radiopharmaceuticals (2007) pp. 573-584, vol. 22, No. 5.
Orlova et al., "Tumor Imaging Using a Picomolar Affinity HER2 BindingAffibody Molecule" Cancer Res 2006; 66: (8). Apr. 15, 2006.
Ronnmark et al., "Construction and Characterization of Affibody-Fc Chimeras Produced in *Escherichia coli*" Journal of Immunological Methods 261 (2002), pp. 199-211.
Tolmachev, "Imaging of HER-2 Overexpressioni n Tumors for Guiding Therapy" Current Pharmaceutical Design, 2008, 14, pp. 2999-3019.
Wikman et al., "Selection and Characterization of HER2/neu-binding Affibody Ligands" Protein Engineering, Design & Selection vol. 17 No. 5 (2004), pp. 455-462.

| Designation | Amino acid sequence | SEQ ID NO |
|---|---|---|
| BM08699 | EKYNAYYEIWQLPNLTKYQKAAFIGKLQD | 1 |
| BM08698 | EKYQAYYEIWQLPNLTKWQKAAFIGKLQD | 2 |
| BM08695 | EKYMAYYEIWQLPNLTKWQKAAFIGKLQD | 3 |
| BM08703 | EKYTAYFEIWQLPNLTKYQKAAFIGKLQD | 4 |
| BM08696 | EKYSAYFEIWQLPNLTKYQKAAFIGKLQD | 5 |
| BM08694 | EKYTAYYEIWQLPNLTKYQKAAFIGKLQD | 6 |
| BM08700 | EKYSAYYEIWQLPNLTKYQKAAFIGKLQD | 7 |
| BM08701 | EKYAAYYEIWQLPNLTKMQKAAFIGKLQD | 8 |
| BM08702 | EKYEAYYEIWQLPNLTKMQKAAFIGKLQD | 9 |
| BM08697 | EKYSAYYEIWQLPNLTRYQKAAFIGKLQD | 10 |
| BM1 | EKYNAYYEIWQLPNLTRYQKAAFIGKLQD | 11 |
| BM2 | EKYTAYYEIWQLPNLTRMQKAAFIGKLQD | 12 |
| BM3 | EKYQAYYEIWQLPNLTRRQAAAFIGKLQD | 13 |
| BM4 | EKYQAYYEIWQLPNLTRYQKAAFIGKLQD | 14 |
| BM8 | EKYAAYYEIWELPNLTVRQKAAFIGKLQD | 15 |
| BM10 | EKYQAYYEIWQLPNLTVRQKAAFIGKLQD | 16 |
| BM12 | EKYSAYFEIWQLPNLTKRQKAAFIGKLED | 17 |
| BM14 | EKYMAYFEIWQLPNLTKRQKAAFIGKLQD | 18 |
| BM15 | EKYNAYFEIWQLPNLTKWQKAAFIGKLQD | 19 |
| BM17 | EKYEAYFEIWQLPNLTKYQKAAFIGKLQD | 20 |
| BM21 | EKYAAYYEIWQLPNLTKYQKAAFISKLQD | 21 |
| BM23 | EKYRAYYEIWQLPNLTKFQKAAFIGKLQD | 22 |
| BM24 | EKYEAYYEIWQLPNLTKFQKAAFIGKLQD | 23 |
| BM25 | EKYAAYYEIWQLPNLTKFQKAAFIGKLQD | 24 |
| BM26 | EKYNAYYEIWQLPNLTKFQKAAFIGKLQD | 25 |
| BM27 | EKYTAYYEIWQLPNLTKFQKAAFIGKLQD | 26 |
| BM28 | EKYSAYYEIWQLPNLTKFQKAAFIGKLQD | 27 |
| BM30 | EKYLAYYEIWQLPNLTKMQKAAFIGKLQD | 28 |
| BM32 | EKYNAYYEIWQLPNLTKMQKAAFIGKLQD | 29 |

FIGURE 1A

| Designation | Amino acid sequence | SEQ ID NO |
|---|---|---|
| BM33 | EKYNAYYEIWQLPNLTKNQKAAFIGKLQD | 30 |
| BM35 | EKYSAYYEIWQLPNLTKNQKAAFIGKLQD | 31 |
| BM37 | EKYRAYFEIWQLPNLTRYQKAAFIGKLQD | 32 |
| BM38 | EKYEAYYEIWQLPNLTKTQKAAFIGKLQD | 33 |
| BM39 | EKYEAYYEIWQLPNLTVRQKAAFIGKLQD | 34 |
| BM40 | EKYNAYYEIWQLPNLTVRQKAAFIGKLQD | 35 |
| A08699 | KEKYNAYYEIWQLPNLTKYQKAAFIGKLQDDPSQSSELLSEAKKLNDSQ | 36 |
| A08698 | KEKYQAYYEIWQLPNLTKWQKAAFIGKLQDDPSQSSELLSEAKKLNDSQ | 37 |
| A08695 | KEKYMAYFEIWQLPNLTKWQKAAFIGKLQDDPSQSSELLSEAKKLNDSQ | 38 |
| A08703 | KEKYTAYFEIWQLPNLTKYQKAAFIGKLQDDPSQSSELLSEAKKLNDSQ | 39 |
| A08696 | KEKYSAYFEIWQLPNLTKYQKAAFIGKLQDDPSQSSELLSEAKKLNDSQ | 40 |
| A08694 | KEKYTAYYEIWQLPNLTKYQKAAFIGKLQDDPSQSSELLSEAKKLNDSQ | 41 |
| A08700 | KEKYSAYYEIWQLPNLTKYQKAAFIGKLQDDPSQSSELLSEAKKLNDSQ | 42 |
| A08701 | KEKYAAYYEIWQLPNLTKMQKAAFIGKLQDDPSQSSELLSEAKKLNDSQ | 43 |
| A08702 | KEKYEAYYEIWQLPNLTKMQKAAFIGKLQDDPSQSSELLSEAKKLNDSQ | 44 |
| A08697 | KEKYSAYYEIWQLPNLTRYQKAAFIGKLQDDPSQSSELLSEAKKLNDSQ | 45 |
| A1 | KEKYNAYYEIWQLPNLTRYQKAAFIGKLQDDPSQSSELLSEAKKLNDSQ | 46 |
| A2 | KEKYTAYYEIWQLPNLTRMQKAAFIGKLQDDPSQSSELLSEAKKLNDSQ | 47 |
| A3 | KEKYQAYYEIWQLPNLTRRQKAAFIGKLQDDPSQSSELLSEAKKLNDSQ | 48 |
| A4 | KEKYMAYFEIWQLPNLTKRQKAAFIGKLQDDPSQSSELLSEAKKLNDSQ | 49 |
| A8 | KEKYQAYYEIWQLPNLTRYQKAAFIGKLQDDPSQSSELLSEAKKLNDSQ | 50 |
| A10 | KEKYSAYYEIWELPNLTVRQKAAFIGKLQDDPSQSSELLSEAKKLNDSQ | 51 |
| A12 | KEKYQAYYEIWQLPNLTVRQKAAFIGKLQDDPSQSSELLSEAKKLNDSQ | 52 |
| A14 | KEKYMAYFEIWQLPNLTKRQKAAFIGKLEDDPSQSSELLSEAKKLNDSQ | 53 |
| A15 | KEKYNAYFEIWQLPNLTKWQKAAFIGKLQDDPSQSSELLSEAKKLNDSQ | 54 |
| A17 | KEKYEAYFEIWQLPNLTKYQKAAFISKLQDDPSQSSELLSEAKKLNDSQ | 55 |
| A21 | KEKYEAYYEIWQLPNLTVRQKAAFIGKLQDDPSQSSELLSEAKKLNDSQ | 56 |
| A23 | KEKYRAYYEIWQLPNLTKFQKAAFIGKLQDDPSQSSELLSEAKKLNDSQ | 57 |
| A24 | KEKYEAYYEIWQLPNLTKFQKAAFIGKLQDDPSQSSELLSEAKKLNDSQ | 58 |

FIGURE 1B

| Designation | Amino acid sequence | SEQ ID NO |
|---|---|---|
| A25 | KEKYAAYYEIWQLPNLTKFQKAAFIGKLQDDPSQSSELLSEAKKLNDSQ | 59 |
| A26 | KEKYNAYYEIWQLPNLTNFQKAAFIGKLQDDPSQSSELLSEAKKLNDSQ | 60 |
| A27 | KEKYTAYYEIWQLPNLTKFQKAAFIGKLQDDPSQSSELLSEAKKLNDSQ | 61 |
| A28 | KEKYSAYYEIWQLPNLTKFQKAAFIGKLQDDPSQSSELLSEAKKLNDSQ | 62 |
| A30 | KEKYLAYYEIWQLPNLTKMQKAAFIGKLQDDPSQSSELLSEAKKLNDSQ | 63 |
| A32 | KEKYNAYYEIWQLPNLTKMQKAAFIGKLQDDPSQSSELLSEAKKLNDSQ | 64 |
| A33 | KEKYNAYYEIWQLPNLTKNQKAAFIGKLQDDPSQSSELLSEAKKLNDSQ | 65 |
| A35 | KEKYSAYYEIWQLPNLTKNQKAAFIGKLQDDPSQSSELLSEAKKLNDSQ | 66 |
| A37 | KEKYRAYFEIWQLPNLTRYQKAAFIGKLQDDPSQSSELLSEAKKLNDSQ | 67 |
| A38 | KEKYEAYYEIWQLPNLTKTQKAAFIGKLQDDPSQSSELLSEAKKLNDSQ | 68 |
| A39 | KEKYEAYYEIWQLPNLTVRQKAAFIGKLQDDPSQSSELLSEAKKLNDSQ | 69 |
| A40 | KEKYNAYYEIWQLPNLTVRQKAAFIGKLQDDPSQSSELLSEAKKLNDSQ | 70 |
| Z08699 | AEAKYAKEKYNAYYEIWQLPNLTKYQKAAFIGKLQDDPSQSSELLSEAKKLNDSQAPK | 71 |
| Z08698 | AEAKYAKEKYQAYYEIWQLPNLTKMQKAAFIGKLQDDPSQSSELLSEAKKLNDSQAPK | 72 |
| Z08695 | AEAKYAKEKYMAYYEIWQLPNLTKMQKAAFIGKLQDDPSQSSELLSEAKKLNDSQAPK | 73 |
| Z08703 | AEAKYAKEKYTAYFEIWQLPNLTKYQKAAFIGKLQDDPSQSSELLSEAKKLNDSQAPK | 74 |
| Z08696 | AEAKYAKEKYTAYYEIWQLPNLTKYQKAAFIGKLQDDPSQSSELLSEAKKLNDSQAPK | 75 |
| Z08694 | AEAKYAKEKYSAYYEIWQLPNLTKYQKAAFIGKLQDDPSQSSELLSEAKKLNDSQAPK | 76 |
| Z08700 | AEAKYAKEKYAAYYEIWQLPNLTKMQKAAFIGKLQDDPSQSSELLSEAKKLNDSQAPK | 77 |
| Z08701 | AEAKYAKEKYAAYYEIWQLPNLTKMQKAAFIGKLQDDPSQSSELLSEAKKLNDSQAPK | 78 |
| Z08702 | AEAKYAKEKYEAYYEIWQLPNLTKMQKAAFIGKLQDDPSQSSELLSEAKKLNDSQAPK | 79 |
| Z08697 | AEAKYAKEKYSAYYEIWQLPNLTRYQKAAFIGKLQDDPSQSSELLSEAKKLNDSQAPK | 80 |
| Z1 | AEAKYAKEKYNAYYEIWQLPNLTRYQKAAFIGKLQDDPSQSSELLSEAKKLNDSQAPK | 81 |
| Z2 | AEAKYAKEKYTAYYEIWQLPNLTRMQKAAFIGKLQDDPSQSSELLSEAKKLNDSQAPK | 82 |
| Z3 | AEAKYAKEKYQAYYEIWQLPNLTRRQAAAFIGKLQDDPSQSSELLSEAKKLNDSQAPK | 83 |
| Z4 | AEAKYAKEKYQAYYEIWQLPNLTRYQKAAFIGKLQDDPSQSSELLSEAKKLNDSQAPK | 84 |
| Z8 | AEAKYAKEKYAAYYEIWELPNLTVRQKAAFIGKLQDDPSQSSELLSEAKKLNDSQAPK | 85 |
| Z10 | AEAKYAKEKYQAYYEIWQLPNLTVRQKAAFIGKLQDDPSQSSELLSEAKKLNDSQAPK | 86 |
| Z12 | AEAKYAKEKYSAYFEIWQLPNLTKRQKAAFIGKLEDDPSQSSELLSEAKKLNDSQAPK | 87 |

FIGURE 1C

| Designation | Amino acid sequence | SEQ ID NO |
|---|---|---|
| Z14 | AEAKYAKEKYMAYFEIWQLPNLTKRQKAAFIGKLQDDPSQSSELLSEAKKLNDSQAPK | 88 |
| Z15 | AEAKYAKEKYNAYFEIWQLPNLTKWQKAAFIGKLQDDPSQSSELLSEAKKLNDSQAPK | 89 |
| Z17 | AEAKYAKEKYEAYFEIWQLPNLTKYQKAAFIGKLQDDPSQSSELLSEAKKLNDSQAPK | 90 |
| Z21 | AEAKYAKEKYAAYYEIWQLPNLTKYQKAAFISKLQDDPSQSSELLSEAKKLNDSQAPK | 91 |
| Z23 | AEAKYAKEKYRAYYEIWQLPNLTKFQKAAFIGKLQDDPSQSSELLSEAKKLNDSQAPK | 92 |
| Z24 | AEAKYAKEKYEAYYEIWQLPNLTKFQKAAFIGKLQDDPSQSSELLSEAKKLNDSQAPK | 93 |
| Z25 | AEAKYAKEKYAAYEIWQLPNLTKFQKAAFIGKLQDDPSQSSELLSEAKKLNDSQAPK | 94 |
| Z26 | AEAKYAKEKYNAYEIWQLPNLTNFQKAAFIGKLQDDPSQSSELLSEAKKLNDSQAPK | 95 |
| Z27 | AEAKYAKEKYTAYYEIWQLPNLTKFQKAAFIGKLQDDPSQSSELLSEAKKLNDSQAPK | 96 |
| Z28 | AEAKYAKEKYSAYYEIWQLPNLTKFQKAAFIGKLQDDPSQSSELLSEAKKLNDSQAPK | 97 |
| Z30 | AEAKYAKEKYLAYYEIWQLPNLTKMQKAAFIGKLQDDPSQSSELLSEAKKLNDSQAPK | 98 |
| Z32 | AEAKYAKEKYNAYYEIWQLPNLTKMQKAAFIGKLQDDPSQSSELLSEAKKLNDSQAPK | 99 |
| Z33 | AEAKYAKEKYNAYYEIWQLPNLTKNQKAAFIGKLQDDPSQSSELLSEAKKLNDSQAPK | 100 |
| Z35 | AEAKYAKEKYSAYYEIWQLPNLTKNQKAAFIGKLQDDPSQSSELLSEAKKLNDSQAPK | 101 |
| Z37 | AEAKYAKEKYRAYYEIWQLPNLTRYQKAAFIGKLQDDPSQSSELLSEAKKLNDSQAPK | 102 |
| Z38 | AEAKYAKEKYEAYYEIWQLPNLTKTQKAAFIGKLQDDPSQSSELLSEAKKLNDSQAPK | 103 |
| Z39 | AEAKYAKEKYEAYYEIWQLPNLTVRQKAAFIGKLQDDPSQSSELLSEAKKLNDSQAPK | 104 |
| Z40 | AEAKYAKEKYNAYYEIWQLPNLTVRQKAAFIGKLQDDPSQSSELLSEAKKLNDSQAPK | 105 |
| Z05416 | VDNKFNKEKYTAYFEIWQLPNLNVRQKAAFISSLQDDPSQSANLLAEAKKLNDAQAPK | 106 |
| Z05417 | VDNKFNKERYSAYYEIWQLPNLNVRQKAAFIGSLQDDPSQSANLLAEAKKLNDAQAPK | 107 |
| PP013 | LAEAKEAANAELDSYGVSDFYKRLIDKAKTVEGVEALKDAILAALP | 109 |

FIGURE 1D

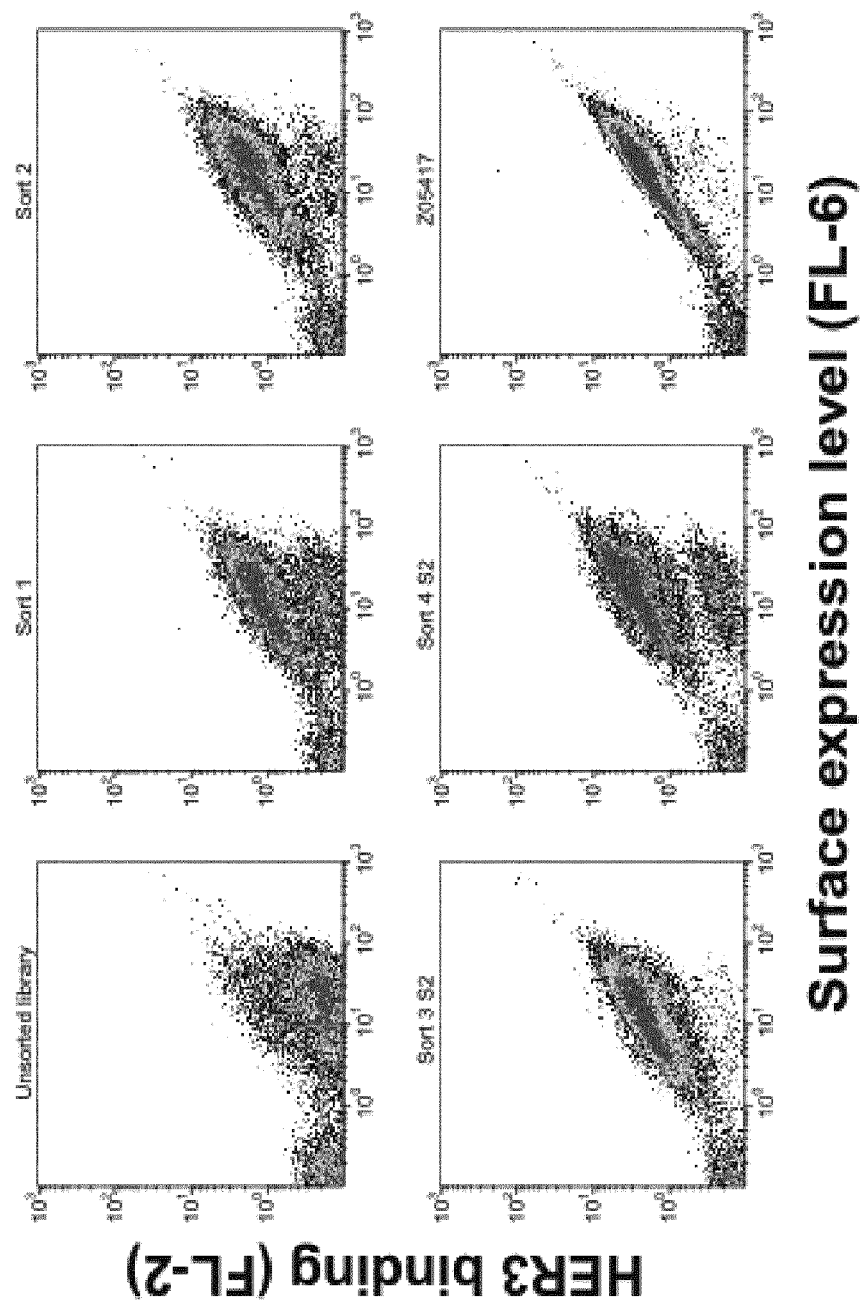

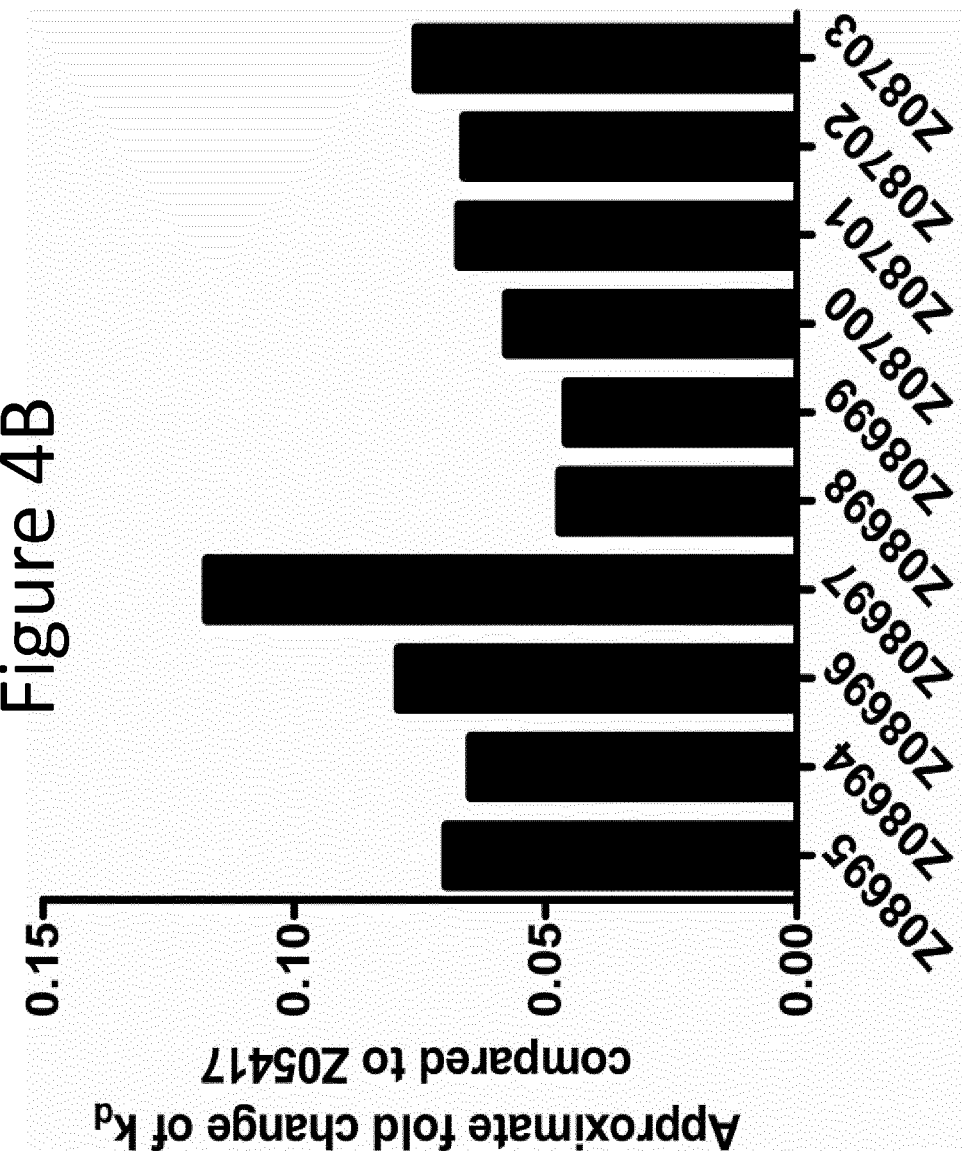

```
                        SEQUENCE LISTING

<160> NUMBER OF SEQ ID NOS: 133

<210> SEQ ID NO 1
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 1

Glu Lys Tyr Asn Ala Tyr Tyr Glu Ile Trp Gln Leu Pro Asn Leu Thr
1               5                   10                  15

Lys Tyr Gln Lys Ala Ala Phe Ile Gly Lys Leu Gln Asp
            20                  25

<210> SEQ ID NO 2
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 2

Glu Lys Tyr Gln Ala Tyr Tyr Glu Ile Trp Gln Leu Pro Asn Leu Thr
1               5                   10                  15

Lys Trp Gln Lys Ala Ala Phe Ile Gly Lys Leu Gln Asp
            20                  25

<210> SEQ ID NO 3
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 3

Glu Lys Tyr Met Ala Tyr Phe Glu Ile Trp Gln Leu Pro Asn Leu Thr
1               5                   10                  15

Lys Trp Gln Lys Ala Ala Phe Ile Gly Lys Leu Gln Asp
            20                  25
```

```
<210> SEQ ID NO 4
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 4

Glu Lys Tyr Thr Ala Tyr Phe Glu Ile Trp Gln Leu Pro Asn Leu Thr
1               5                   10                  15

Lys Tyr Gln Lys Ala Ala Phe Ile Gly Lys Leu Gln Asp
            20                  25

<210> SEQ ID NO 5
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 5

Glu Lys Tyr Ser Ala Tyr Phe Glu Ile Trp Gln Leu Pro Asn Leu Thr
1               5                   10                  15

Lys Tyr Gln Lys Ala Ala Phe Ile Gly Lys Leu Gln Asp
            20                  25

<210> SEQ ID NO 6
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 6

Glu Lys Tyr Thr Ala Tyr Tyr Glu Ile Trp Gln Leu Pro Asn Leu Thr
1               5                   10                  15

Lys Tyr Gln Lys Ala Ala Phe Ile Gly Lys Leu Gln Asp
            20                  25

<210> SEQ ID NO 7
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 7

Glu Lys Tyr Ser Ala Tyr Tyr Glu Ile Trp Gln Leu Pro Asn Leu Thr
1               5                   10                  15

Lys Tyr Gln Lys Ala Ala Phe Ile Gly Lys Leu Gln Asp
            20                  25

<210> SEQ ID NO 8
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 8

Glu Lys Tyr Ala Ala Tyr Tyr Glu Ile Trp Gln Leu Pro Asn Leu Thr
1               5                   10                  15

Lys Met Gln Lys Ala Ala Phe Ile Gly Lys Leu Gln Asp
            20                  25
```

```
<210> SEQ ID NO 9
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 9

Glu Lys Tyr Glu Ala Tyr Tyr Glu Ile Trp Gln Leu Pro Asn Leu Thr
1               5                   10                  15

Lys Met Gln Lys Ala Ala Phe Ile Gly Lys Leu Gln Asp
            20                  25

<210> SEQ ID NO 10
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 10

Glu Lys Tyr Ser Ala Tyr Tyr Glu Ile Trp Gln Leu Pro Asn Leu Thr
1               5                   10                  15

Arg Tyr Gln Lys Ala Ala Phe Ile Gly Lys Leu Gln Asp
            20                  25

<210> SEQ ID NO 11
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 11

Glu Lys Tyr Asn Ala Tyr Tyr Glu Ile Trp Gln Leu Pro Asn Leu Thr
1               5                   10                  15

Arg Tyr Gln Lys Ala Ala Phe Ile Gly Lys Leu Gln Asp
            20                  25

<210> SEQ ID NO 12
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 12

Glu Lys Tyr Thr Ala Tyr Tyr Glu Ile Trp Gln Leu Pro Asn Leu Thr
1               5                   10                  15

Arg Met Gln Lys Ala Ala Phe Ile Gly Lys Leu Gln Asp
            20                  25

<210> SEQ ID NO 13
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 13

Glu Lys Tyr Gln Ala Tyr Tyr Glu Ile Trp Gln Leu Pro Asn Leu Thr
1               5                   10                  15

Arg Arg Gln Ala Ala Ala Phe Ile Gly Lys Leu Gln Asp
            20                  25
```

```
<210> SEQ ID NO 14
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 14

Glu Lys Tyr Gln Ala Tyr Tyr Glu Ile Trp Gln Leu Pro Asn Leu Thr
1               5                   10                  15

Arg Tyr Gln Lys Ala Ala Phe Ile Gly Lys Leu Gln Asp
            20                  25

<210> SEQ ID NO 15
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 15

Glu Lys Tyr Ala Ala Tyr Tyr Glu Ile Trp Glu Leu Pro Asn Leu Thr
1               5                   10                  15

Val Arg Gln Lys Ala Ala Phe Ile Gly Lys Leu Gln Asp
            20                  25

<210> SEQ ID NO 16
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 16

Glu Lys Tyr Gln Ala Tyr Tyr Glu Ile Trp Gln Leu Pro Asn Leu Thr
1               5                   10                  15

Val Arg Gln Lys Ala Ala Phe Ile Gly Lys Leu Gln Asp
            20                  25

<210> SEQ ID NO 17
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 17

Glu Lys Tyr Ser Ala Tyr Phe Glu Ile Trp Gln Leu Pro Asn Leu Thr
1               5                   10                  15

Lys Arg Gln Lys Ala Ala Phe Ile Gly Lys Leu Glu Asp
            20                  25

<210> SEQ ID NO 18
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 18

Glu Lys Tyr Met Ala Tyr Phe Glu Ile Trp Gln Leu Pro Asn Leu Thr
1               5                   10                  15

Lys Arg Gln Lys Ala Ala Phe Ile Gly Lys Leu Gln Asp
```

20                  25

<210> SEQ ID NO 19
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 19

Glu Lys Tyr Asn Ala Tyr Phe Glu Ile Trp Gln Leu Pro Asn Leu Thr
1               5                   10                  15

Lys Trp Gln Lys Ala Ala Phe Ile Gly Lys Leu Gln Asp
            20                  25

<210> SEQ ID NO 20
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 20

Glu Lys Tyr Glu Ala Tyr Phe Glu Ile Trp Gln Leu Pro Asn Leu Thr
1               5                   10                  15

Lys Tyr Gln Lys Ala Ala Phe Ile Gly Lys Leu Gln Asp
            20                  25

<210> SEQ ID NO 21
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 21

Glu Lys Tyr Ala Ala Tyr Tyr Glu Ile Trp Gln Leu Pro Asn Leu Thr
1               5                   10                  15

Lys Tyr Gln Lys Ala Ala Phe Ile Ser Lys Leu Gln Asp
            20                  25

<210> SEQ ID NO 22
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 22

Glu Lys Tyr Arg Ala Tyr Tyr Glu Ile Trp Gln Leu Pro Asn Leu Thr
1               5                   10                  15

Lys Phe Gln Lys Ala Ala Phe Ile Gly Lys Leu Gln Asp
            20                  25

<210> SEQ ID NO 23
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 23

Glu Lys Tyr Glu Ala Tyr Tyr Glu Ile Trp Gln Leu Pro Asn Leu Thr
1               5                   10                  15

Lys Phe Gln Lys Ala Ala Phe Ile Gly Lys Leu Gln Asp
            20                  25

<210> SEQ ID NO 24
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 24

Glu Lys Tyr Ala Ala Tyr Tyr Glu Ile Trp Gln Leu Pro Asn Leu Thr
1               5                   10                  15

Lys Phe Gln Lys Ala Ala Phe Ile Gly Lys Leu Gln Asp
            20                  25

<210> SEQ ID NO 25
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 25

Glu Lys Tyr Asn Ala Tyr Tyr Glu Ile Trp Gln Leu Pro Asn Leu Thr
1               5                   10                  15

Asn Phe Gln Lys Ala Ala Phe Ile Gly Lys Leu Gln Asp
            20                  25

<210> SEQ ID NO 26
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 26

Glu Lys Tyr Thr Ala Tyr Tyr Glu Ile Trp Gln Leu Pro Asn Leu Thr
1               5                   10                  15

Lys Phe Gln Lys Ala Ala Phe Ile Gly Lys Leu Gln Asp
            20                  25

<210> SEQ ID NO 27
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 27

Glu Lys Tyr Ser Ala Tyr Tyr Glu Ile Trp Gln Leu Pro Asn Leu Thr
1               5                   10                  15

Lys Phe Gln Lys Ala Ala Phe Ile Gly Lys Leu Gln Asp
            20                  25

<210> SEQ ID NO 28
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 28

Glu Lys Tyr Leu Ala Tyr Tyr Glu Ile Trp Gln Leu Pro Asn Leu Thr
1               5                   10                  15

```
Lys Met Gln Lys Ala Ala Phe Ile Gly Lys Leu Gln Asp
            20                  25
```

<210> SEQ ID NO 29
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 29

```
Glu Lys Tyr Asn Ala Tyr Tyr Glu Ile Trp Gln Leu Pro Asn Leu Thr
1               5                   10                  15

Lys Met Gln Lys Ala Ala Phe Ile Gly Lys Leu Gln Asp
            20                  25
```

<210> SEQ ID NO 30
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 30

```
Glu Lys Tyr Asn Ala Tyr Tyr Glu Ile Trp Gln Leu Pro Asn Leu Thr
1               5                   10                  15

Lys Asn Gln Lys Ala Ala Phe Ile Gly Lys Leu Gln Asp
            20                  25
```

<210> SEQ ID NO 31
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 31

```
Glu Lys Tyr Ser Ala Tyr Tyr Glu Ile Trp Gln Leu Pro Asn Leu Thr
1               5                   10                  15

Lys Asn Gln Lys Ala Ala Phe Ile Gly Lys Leu Gln Asp
            20                  25
```

<210> SEQ ID NO 32
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 32

```
Glu Lys Tyr Arg Ala Tyr Phe Glu Ile Trp Gln Leu Pro Asn Leu Thr
1               5                   10                  15

Arg Tyr Gln Lys Ala Ala Phe Ile Gly Lys Leu Gln Asp
            20                  25
```

<210> SEQ ID NO 33
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 33

```
Glu Lys Tyr Glu Ala Tyr Tyr Glu Ile Trp Gln Leu Pro Asn Leu Thr
```

```
1               5                   10                  15
Lys Thr Gln Lys Ala Ala Phe Ile Gly Lys Leu Gln Asp
            20                  25
```

<210> SEQ ID NO 34
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 34

```
Glu Lys Tyr Glu Ala Tyr Tyr Glu Ile Trp Gln Leu Pro Asn Leu Thr
1               5                   10                  15
Val Arg Gln Lys Ala Ala Phe Ile Gly Lys Leu Gln Asp
            20                  25
```

<210> SEQ ID NO 35
<211> LENGTH: 29
<212> TYPE: PRT
<213> ORGANISM: Artificial Sequence
<220> FEATURE:
<223> OTHER INFORMATION: Engineered HER3 binding polypeptide

<400> SEQUENCE: 35

```
Glu Lys Tyr Asn Ala Tyr Tyr Glu Ile Trp Gln Leu Pro Asn Leu Thr
1               5                   10                  15
Val Arg Gln Lys Ala Ala Phe Ile Gly Lys Leu Gln Asp
            20                  25
```

<210> SEQ ID NO 36
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 36

```
Lys Glu Lys Tyr Asn Ala Tyr Tyr Glu Ile Trp Gln Leu Pro Asn Leu
1               5                   10                  15
Thr Lys Tyr Gln Lys Ala Ala Phe Ile Gly Lys Leu Gln Asp Asp Pro
            20                  25                  30
Ser Gln Ser Ser Glu Leu Leu Ser Glu Ala Lys Lys Leu Asn Asp Ser
        35                  40                  45
Gln
```

<210> SEQ ID NO 37
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 37

```
Lys Glu Lys Tyr Gln Ala Tyr Tyr Glu Ile Trp Gln Leu Pro Asn Leu
1               5                   10                  15
Thr Lys Trp Gln Lys Ala Ala Phe Ile Gly Lys Leu Gln Asp Asp Pro
            20                  25                  30
Ser Gln Ser Ser Glu Leu Leu Ser Glu Ala Lys Lys Leu Asn Asp Ser
        35                  40                  45
Gln
```

<210> SEQ ID NO 38
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 38

Lys Glu Lys Tyr Met Ala Tyr Phe Glu Ile Trp Gln Leu Pro Asn Leu
1               5                   10                  15

Thr Lys Trp Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 39
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 39

Lys Glu Lys Tyr Thr Ala Tyr Phe Glu Ile Trp Gln Leu Pro Asn Leu
1               5                   10                  15

Thr Lys Tyr Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 40
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 40

Lys Glu Lys Tyr Ser Ala Tyr Phe Glu Ile Trp Gln Leu Pro Asn Leu
1               5                   10                  15

Thr Lys Tyr Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 41
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 41

Lys Glu Lys Tyr Thr Ala Tyr Tyr Glu Ile Trp Gln Leu Pro Asn Leu
1               5                   10                  15

Thr Lys Tyr Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 42
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 42

Lys Glu Lys Tyr Ser Ala Tyr Tyr Glu Ile Trp Gln Leu Pro Asn Leu
1               5                   10                  15

Thr Lys Tyr Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 43
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 43

Lys Glu Lys Tyr Ala Ala Tyr Tyr Glu Ile Trp Gln Leu Pro Asn Leu
1               5                   10                  15

Thr Lys Met Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 44
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 44

Lys Glu Lys Tyr Glu Ala Tyr Tyr Glu Ile Trp Gln Leu Pro Asn Leu
1               5                   10                  15

Thr Lys Met Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 45
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 45

Lys Glu Lys Tyr Ser Ala Tyr Tyr Glu Ile Trp Gln Leu Pro Asn Leu

```
                1               5                  10                 15
         Thr Arg Tyr Gln Lys Ala Ala Phe Ile Gly Lys Leu Gln Asp Asp Pro
                           20                  25                  30

Ser Gln Ser Ser Glu Leu Leu Ser Glu Ala Lys Lys Leu Asn Asp Ser
                   35                  40                  45

Gln

<210> SEQ ID NO 46
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 46

Lys Glu Lys Tyr Asn Ala Tyr Tyr Glu Ile Trp Gln Leu Pro Asn Leu
1               5                  10                  15

Thr Arg Tyr Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 47
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 47

Lys Glu Lys Tyr Thr Ala Tyr Tyr Glu Ile Trp Gln Leu Pro Asn Leu
1               5                  10                  15

Thr Arg Met Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 48
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 48

Lys Glu Lys Tyr Gln Ala Tyr Tyr Glu Ile Trp Gln Leu Pro Asn Leu
1               5                  10                  15

Thr Arg Arg Gln Ala Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 49
<211> LENGTH: 49
<212> TYPE: PRT
<213> ORGANISM: Artificial Sequence
<220> FEATURE:
```

<223> OTHER INFORMATION: Engineered HER3 binding polypeptide

<400> SEQUENCE: 49

Lys Glu Lys Tyr Gln Ala Tyr Tyr Glu Ile Trp Gln Leu Pro Asn Leu
1               5                   10                  15

Thr Arg Tyr Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 50
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 50

Lys Glu Lys Tyr Ala Ala Tyr Tyr Glu Ile Trp Glu Leu Pro Asn Leu
1               5                   10                  15

Thr Val Arg Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 51
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 51

Lys Glu Lys Tyr Gln Ala Tyr Tyr Glu Ile Trp Gln Leu Pro Asn Leu
1               5                   10                  15

Thr Val Arg Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 52
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 52

Lys Glu Lys Tyr Ser Ala Tyr Phe Glu Ile Trp Gln Leu Pro Asn Leu
1               5                   10                  15

Thr Lys Arg Gln Lys Ala Ala Phe Ile Gly Lys Leu Glu Asp Asp Pro
            20                  25                  30

Ser Gln Ser Ser Glu Leu Leu Ser Glu Ala Lys Lys Leu Asn Asp Ser
        35                  40                  45

Gln

```
<210> SEQ ID NO 53
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 53

Lys Glu Lys Tyr Met Ala Tyr Phe Glu Ile Trp Gln Leu Pro Asn Leu
1               5                   10                  15

Thr Lys Arg Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 54
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 54

Lys Glu Lys Tyr Asn Ala Tyr Phe Glu Ile Trp Gln Leu Pro Asn Leu
1               5                   10                  15

Thr Lys Trp Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 55
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 55

Lys Glu Lys Tyr Glu Ala Tyr Phe Glu Ile Trp Gln Leu Pro Asn Leu
1               5                   10                  15

Thr Lys Tyr Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 56
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 56

Lys Glu Lys Tyr Ala Ala Tyr Tyr Glu Ile Trp Gln Leu Pro Asn Leu
1               5                   10                  15

Thr Lys Tyr Gln Lys Ala Ala Phe Ile Ser Lys Leu Gln Asp Asp Pro
            20                  25                  30

Ser Gln Ser Ser Glu Leu Leu Ser Glu Ala Lys Lys Leu Asn Asp Ser
```

-continued

```
                    35                  40                  45

Gln

<210> SEQ ID NO 57
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 57

Lys Glu Lys Tyr Arg Ala Tyr Tyr Glu Ile Trp Gln Leu Pro Asn Leu
1               5                   10                  15

Thr Lys Phe Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 58
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 58

Lys Glu Lys Tyr Glu Ala Tyr Tyr Glu Ile Trp Gln Leu Pro Asn Leu
1               5                   10                  15

Thr Lys Phe Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 59
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 59

Lys Glu Lys Tyr Ala Ala Tyr Tyr Glu Ile Trp Gln Leu Pro Asn Leu
1               5                   10                  15

Thr Lys Phe Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 60
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 60

Lys Glu Lys Tyr Asn Ala Tyr Tyr Glu Ile Trp Gln Leu Pro Asn Leu
1               5                   10                  15
```

-continued

Thr Asn Phe Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 61
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 61

Lys Glu Lys Tyr Thr Ala Tyr Tyr Glu Ile Trp Gln Leu Pro Asn Leu
1               5                   10                  15

Thr Lys Phe Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 62
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 62

Lys Glu Lys Tyr Ser Ala Tyr Tyr Glu Ile Trp Gln Leu Pro Asn Leu
1               5                   10                  15

Thr Lys Phe Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 63
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 63

Lys Glu Lys Tyr Leu Ala Tyr Tyr Glu Ile Trp Gln Leu Pro Asn Leu
1               5                   10                  15

Thr Lys Met Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 64
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 64

Lys Glu Lys Tyr Asn Ala Tyr Tyr Glu Ile Trp Gln Leu Pro Asn Leu
1               5                   10                  15

Thr Lys Met Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 65
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 65

Lys Glu Lys Tyr Asn Ala Tyr Tyr Glu Ile Trp Gln Leu Pro Asn Leu
1               5                   10                  15

Thr Lys Asn Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 66
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 66

Lys Glu Lys Tyr Ser Ala Tyr Tyr Glu Ile Trp Gln Leu Pro Asn Leu
1               5                   10                  15

Thr Lys Asn Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 67
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 67

Lys Glu Lys Tyr Arg Ala Tyr Phe Glu Ile Trp Gln Leu Pro Asn Leu
1               5                   10                  15

Thr Arg Tyr Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 68

-continued

```
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 68

Lys Glu Lys Tyr Glu Ala Tyr Tyr Glu Ile Trp Gln Leu Pro Asn Leu
1               5                   10                  15

Thr Lys Thr Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 69
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 69

Lys Glu Lys Tyr Glu Ala Tyr Tyr Glu Ile Trp Gln Leu Pro Asn Leu
1               5                   10                  15

Thr Val Arg Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 70
<211> LENGTH: 49
<212> TYPE: PRT
<213> ORGANISM: Artificial Sequence
<220> FEATURE:
<223> OTHER INFORMATION: Engineered HER3 binding polypeptide

<400> SEQUENCE: 70

Lys Glu Lys Tyr Asn Ala Tyr Tyr Glu Ile Trp Gln Leu Pro Asn Leu
1               5                   10                  15

Thr Val Arg Gln Lys Ala Ala Phe Ile Gly Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 71
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 71

Ala Glu Ala Lys Tyr Ala Lys Glu Lys Tyr Asn Ala Tyr Tyr Glu Ile
1               5                   10                  15

Trp Gln Leu Pro Asn Leu Thr Lys Tyr Gln Lys Ala Ala Phe Ile Gly
            20                  25                  30

Lys Leu Gln Asp Asp Pro Ser Gln Ser Ser Glu Leu Leu Ser Glu Ala
        35                  40                  45
```

```
Lys Lys Leu Asn Asp Ser Gln Ala Pro Lys
    50                  55
```

<210> SEQ ID NO 72
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 72

```
Ala Glu Ala Lys Tyr Ala Lys Glu Lys Tyr Gln Ala Tyr Tyr Glu Ile
1               5                   10                  15

Trp Gln Leu Pro Asn Leu Thr Lys Trp Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 73
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 73

```
Ala Glu Ala Lys Tyr Ala Lys Glu Lys Tyr Met Ala Tyr Phe Glu Ile
1               5                   10                  15

Trp Gln Leu Pro Asn Leu Thr Lys Trp Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 74
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 74

```
Ala Glu Ala Lys Tyr Ala Lys Glu Lys Tyr Thr Ala Tyr Phe Glu Ile
1               5                   10                  15

Trp Gln Leu Pro Asn Leu Thr Lys Tyr Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 75
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 75

Ala Glu Ala Lys Tyr Ala Lys Glu Lys Tyr Ser Ala Tyr Phe Glu Ile
1               5                   10                  15

Trp Gln Leu Pro Asn Leu Thr Lys Tyr Gln Lys Ala Ala Phe Ile Gly
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 76
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 76

Ala Glu Ala Lys Tyr Ala Lys Glu Lys Tyr Thr Ala Tyr Tyr Glu Ile
1               5                   10                  15

Trp Gln Leu Pro Asn Leu Thr Lys Tyr Gln Lys Ala Ala Phe Ile Gly
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 77
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 77

Ala Glu Ala Lys Tyr Ala Lys Glu Lys Tyr Ser Ala Tyr Tyr Glu Ile
1               5                   10                  15

Trp Gln Leu Pro Asn Leu Thr Lys Tyr Gln Lys Ala Ala Phe Ile Gly
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 78
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 78

Ala Glu Ala Lys Tyr Ala Lys Glu Lys Tyr Ala Ala Tyr Tyr Glu Ile
1               5                   10                  15

Trp Gln Leu Pro Asn Leu Thr Lys Met Gln Lys Ala Ala Phe Ile Gly
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 79
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 79

Ala Glu Ala Lys Tyr Ala Lys Glu Lys Tyr Glu Ala Tyr Tyr Glu Ile
1               5                   10                  15

Trp Gln Leu Pro Asn Leu Thr Lys Met Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 80
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 80

Ala Glu Ala Lys Tyr Ala Lys Glu Lys Tyr Ser Ala Tyr Tyr Glu Ile
1               5                   10                  15

Trp Gln Leu Pro Asn Leu Thr Arg Tyr Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 81
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 81

Ala Glu Ala Lys Tyr Ala Lys Glu Lys Tyr Asn Ala Tyr Tyr Glu Ile
1               5                   10                  15

Trp Gln Leu Pro Asn Leu Thr Arg Tyr Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 82
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 82

Ala Glu Ala Lys Tyr Ala Lys Glu Lys Tyr Thr Ala Tyr Tyr Glu Ile
1               5                   10                  15

-continued

Trp Gln Leu Pro Asn Leu Thr Arg Met Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 83
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 83

Ala Glu Ala Lys Tyr Ala Lys Glu Lys Tyr Gln Ala Tyr Tyr Glu Ile
1               5                   10                  15

Trp Gln Leu Pro Asn Leu Thr Arg Arg Gln Ala Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 84
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 84

Ala Glu Ala Lys Tyr Ala Lys Glu Lys Tyr Gln Ala Tyr Tyr Glu Ile
1               5                   10                  15

Trp Gln Leu Pro Asn Leu Thr Arg Tyr Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 85
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 85

Ala Glu Ala Lys Tyr Ala Lys Glu Lys Tyr Ala Ala Tyr Tyr Glu Ile
1               5                   10                  15

Trp Glu Leu Pro Asn Leu Thr Val Arg Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 86
<211> LENGTH: 58
<212> TYPE: PRT

<213> ORGANISM: Artificial Sequence
<220> FEATURE:
<223> OTHER INFORMATION: Engineered HER3 binding polypeptide

<400> SEQUENCE: 86

Ala Glu Ala Lys Tyr Ala Lys Glu Lys Tyr Gln Ala Tyr Tyr Glu Ile
1               5                   10                  15

Trp Gln Leu Pro Asn Leu Thr Val Arg Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 87
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 87

Ala Glu Ala Lys Tyr Ala Lys Glu Lys Tyr Ser Ala Tyr Phe Glu Ile
1               5                   10                  15

Trp Gln Leu Pro Asn Leu Thr Lys Arg Gln Lys Ala Ala Phe Ile Gly
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 88
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 88

Ala Glu Ala Lys Tyr Ala Lys Glu Lys Tyr Met Ala Tyr Phe Glu Ile
1               5                   10                  15

Trp Gln Leu Pro Asn Leu Thr Lys Arg Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 89
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 89

Ala Glu Ala Lys Tyr Ala Lys Glu Lys Tyr Asn Ala Tyr Phe Glu Ile
1               5                   10                  15

Trp Gln Leu Pro Asn Leu Thr Lys Trp Gln Lys Ala Ala Phe Ile Gly
            20                  25                  30

Lys Leu Gln Asp Asp Pro Ser Gln Ser Ser Glu Leu Leu Ser Glu Ala

-continued

<210> SEQ ID NO 90
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 90

Ala Glu Ala Lys Tyr Ala Lys Glu Lys Tyr Glu Ala Tyr Phe Glu Ile
1               5                   10                  15

Trp Gln Leu Pro Asn Leu Thr Lys Tyr Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 91
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 91

Ala Glu Ala Lys Tyr Ala Lys Glu Lys Tyr Ala Ala Tyr Tyr Glu Ile
1               5                   10                  15

Trp Gln Leu Pro Asn Leu Thr Lys Tyr Gln Lys Ala Ala Phe Ile Ser
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 92
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 92

Ala Glu Ala Lys Tyr Ala Lys Glu Lys Tyr Arg Ala Tyr Tyr Glu Ile
1               5                   10                  15

Trp Gln Leu Pro Asn Leu Thr Lys Phe Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 93
<211> LENGTH: 58
<212> TYPE: PRT
<213> ORGANISM: Artificial Sequence
<220> FEATURE:
<223> OTHER INFORMATION: Engineered HER3 binding polypeptide -continued

<400> SEQUENCE: 93

Ala Glu Ala Lys Tyr Ala Lys Glu Lys Tyr Glu Ala Tyr Tyr Glu Ile
1               5                   10                  15

Trp Gln Leu Pro Asn Leu Thr Lys Phe Gln Lys Ala Ala Phe Ile Gly
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 94
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 94

Ala Glu Ala Lys Tyr Ala Lys Glu Lys Tyr Ala Ala Tyr Tyr Glu Ile
1               5                   10                  15

Trp Gln Leu Pro Asn Leu Thr Lys Phe Gln Lys Ala Ala Phe Ile Gly
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 95
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 95

Ala Glu Ala Lys Tyr Ala Lys Glu Lys Tyr Asn Ala Tyr Tyr Glu Ile
1               5                   10                  15

Trp Gln Leu Pro Asn Leu Thr Asn Phe Gln Lys Ala Ala Phe Ile Gly
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 96
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 96

Ala Glu Ala Lys Tyr Ala Lys Glu Lys Tyr Thr Ala Tyr Tyr Glu Ile
1               5                   10                  15

Trp Gln Leu Pro Asn Leu Thr Lys Phe Gln Lys Ala Ala Phe Ile Gly
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 97
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 97

```
Ala Glu Ala Lys Tyr Ala Lys Glu Lys Tyr Ser Ala Tyr Tyr Glu Ile
1               5                   10                  15

Trp Gln Leu Pro Asn Leu Thr Lys Phe Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 98
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 98

```
Ala Glu Ala Lys Tyr Ala Lys Glu Lys Tyr Leu Ala Tyr Tyr Glu Ile
1               5                   10                  15

Trp Gln Leu Pro Asn Leu Thr Lys Met Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 99
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 99

```
Ala Glu Ala Lys Tyr Ala Lys Glu Lys Tyr Asn Ala Tyr Tyr Glu Ile
1               5                   10                  15

Trp Gln Leu Pro Asn Leu Thr Lys Met Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 100
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 100

```
Ala Glu Ala Lys Tyr Ala Lys Glu Lys Tyr Asn Ala Tyr Tyr Glu Ile
1               5                   10                  15
```

```
Trp Gln Leu Pro Asn Leu Thr Lys Asn Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 101
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 101

Ala Glu Ala Lys Tyr Ala Lys Glu Lys Tyr Ser Ala Tyr Tyr Glu Ile
1               5                   10                  15

Trp Gln Leu Pro Asn Leu Thr Lys Asn Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 102
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 102

Ala Glu Ala Lys Tyr Ala Lys Glu Lys Tyr Arg Ala Tyr Phe Glu Ile
1               5                   10                  15

Trp Gln Leu Pro Asn Leu Thr Arg Tyr Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 103
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 103

Ala Glu Ala Lys Tyr Ala Lys Glu Lys Tyr Glu Ala Tyr Tyr Glu Ile
1               5                   10                  15

Trp Gln Leu Pro Asn Leu Thr Lys Thr Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 104
<211> LENGTH: 58
```

```
<212> TYPE: PRT
<213> ORGANISM: Artificial Sequence
<220> FEATURE:
<223> OTHER INFORMATION: Engineered HER3 binding polypeptide

<400> SEQUENCE: 104

Ala Glu Ala Lys Tyr Ala Lys Glu Lys Tyr Glu Ala Tyr Tyr Glu Ile
1               5                   10                  15

Trp Gln Leu Pro Asn Leu Thr Val Arg Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 105
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 105

Ala Glu Ala Lys Tyr Ala Lys Glu Lys Tyr Asn Ala Tyr Tyr Glu Ile
1               5                   10                  15

Trp Gln Leu Pro Asn Leu Thr Val Arg Gln Lys Ala Ala Phe Ile Gly
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 106
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 106

Val Asp Asn Lys Phe Asn Lys Glu Lys Tyr Thr Ala Tyr Phe Glu Ile
1               5                   10                  15

Trp Gln Leu Pro Asn Leu Asn Val Arg Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 107
<211> LENGTH: 58
<212> TYPE: PRT
<213> ORGANISM: Artificial Sequence
<220> FEATURE:
<223> OTHER INFORMATION: Engineered HER3 binding polypeptide

<400> SEQUENCE: 107

Val Asp Asn Lys Phe Asn Lys Glu Arg Tyr Ser Ala Tyr Tyr Glu Ile
1               5                   10                  15

Trp Gln Leu Pro Asn Leu Asn Val Arg Gln Lys Ala Ala Phe Ile Gly
            20                  25                  30
```

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 108
<211> LENGTH: 133
<212> TYPE: DNA
<213> ORGANISM: Artificial Sequence
<220> FEATURE:
<223> OTHER INFORMATION: Library oligonucleotide
<220> FEATURE:
<221> NAME/KEY: misc_feature
<222> LOCATION: (31)..(39)
<223> OTHER INFORMATION: n is a, c, g, or t
<220> FEATURE:
<221> NAME/KEY: misc_feature
<222> LOCATION: (43)..(48)
<223> OTHER INFORMATION: n is a, c, g, or t
<220> FEATURE:
<221> NAME/KEY: misc_feature
<222> LOCATION: (55)..(60)
<223> OTHER INFORMATION: n is a, c, g, or t
<220> FEATURE:
<221> NAME/KEY: misc_feature
<222> LOCATION: (76)..(81)
<223> OTHER INFORMATION: n is a, c, g, or t
<220> FEATURE:
<221> NAME/KEY: misc_feature
<222> LOCATION: (85)..(90)
<223> OTHER INFORMATION: n is a, c, g, or t
<220> FEATURE:
<221> NAME/KEY: misc_feature
<222> LOCATION: (100)..(102)
<223> OTHER INFORMATION: n is a, c, g, or t
<220> FEATURE:
<221> NAME/KEY: misc_feature
<222> LOCATION: (109)..(111)
<223> OTHER INFORMATION: n is a, c, g, or t

<400> SEQUENCE: 108
ctcgaggcgg aagccaaata cgccaaagaa nnnnnnnnng cgnnnnnnga gatcnnnnnn      60
ttacctaact taaccnnnnn ncaannnnnn gccttcatcn nnaaattann ngatgaccca     120
agccagagct ctc                                                        133

<210> SEQ ID NO 109
<211> LENGTH: 46
<212> TYPE: PRT
<213> ORGANISM: Artificial Sequence
<220> FEATURE:
<223> OTHER INFORMATION: Engineered albumin binding polypeptide

<400> SEQUENCE: 109

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 110
<211> LENGTH: 29
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (4)..(4)

```
<223> OTHER INFORMATION: Xaa is selected from A, E, L, M, N, Q, R, S
      and T
<220> FEATURE:
<221> NAME/KEY: MISC_FEATURE
<222> LOCATION: (7)..(7)
<223> OTHER INFORMATION: Xaa is selected from F and Y
<220> FEATURE:
<221> NAME/KEY: MISC_FEATURE
<222> LOCATION: (11)..(11)
<223> OTHER INFORMATION: Xaa is selected from E and Q
<220> FEATURE:
<221> NAME/KEY: MISC_FEATURE
<222> LOCATION: (17)..(17)
<223> OTHER INFORMATION: Xaa is selected from K, N, R and V
<220> FEATURE:
<221> NAME/KEY: MISC_FEATURE
<222> LOCATION: (18)..(18)
<223> OTHER INFORMATION: Xaa is selected from F, M, N, R, T, Y and W
<220> FEATURE:
<221> NAME/KEY: MISC_FEATURE
<222> LOCATION: (20)..(20)
<223> OTHER INFORMATION: Xaa is selected from A and K
<220> FEATURE:
<221> NAME/KEY: MISC_FEATURE
<222> LOCATION: (26)..(26)
<223> OTHER INFORMATION: Xaa is selected from K and S
<220> FEATURE:
<221> NAME/KEY: MISC_FEATURE
<222> LOCATION: (28)..(28)
<223> OTHER INFORMATION: Xaa is selected from E and Q

<400> SEQUENCE: 110

Glu Lys Tyr Xaa Ala Tyr Xaa Glu Ile Trp Xaa Leu Pro Asn Leu Thr
1               5                   10                  15

Xaa Xaa Gln Xaa Ala Ala Phe Ile Gly Xaa Leu Xaa Asp
            20                  25

<210> SEQ ID NO 111
<211> LENGTH: 20
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (1)..(2)
<223> OTHER INFORMATION: HER3 binding motif
<220> FEATURE:
<221> NAME/KEY: MISC_FEATURE
<222> LOCATION: (7)..(7)
<223> OTHER INFORMATION: Xaa is selected from A and S
<220> FEATURE:
<221> NAME/KEY: MISC_FEATURE
<222> LOCATION: (8)..(8)
<223> OTHER INFORMATION: Xaa is selected from N and E
<220> FEATURE:
<221> NAME/KEY: MISC_FEATURE
<222> LOCATION: (11)..(11)
<223> OTHER INFORMATION: Xaa is selected from A, S and C
<220> FEATURE:
<221> NAME/KEY: MISC_FEATURE
<222> LOCATION: (19)..(19)
<223> OTHER INFORMATION: Xaa is selected from A and S

<400> SEQUENCE: 111

Lys Asp Pro Ser Gln Ser Xaa Xaa Leu Leu Xaa Glu Ala Lys Lys Leu
1               5                   10                  15

Asn Asp Xaa Gln
            20

<210> SEQ ID NO 112
<211> LENGTH: 24
<212> TYPE: PRT
```

<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (3)..(4)
<223> OTHER INFORMATION: HER3 binding motif
<220> FEATURE:
<221> NAME/KEY: MISC_FEATURE
<222> LOCATION: (13)..(13)
<223> OTHER INFORMATION: Xaa is selected from S and C

<400> SEQUENCE: 112

Tyr Ala Lys Asp Pro Ser Gln Ser Ser Glu Leu Leu Xaa Glu Ala Lys
1               5                   10                  15

Lys Leu Asn Asp Ser Gln Ala Pro
            20

<210> SEQ ID NO 113
<211> LENGTH: 24
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (3)..(4)
<223> OTHER INFORMATION: HER3 binding motif
<220> FEATURE:
<221> NAME/KEY: MISC_FEATURE
<222> LOCATION: (13)..(13)
<223> OTHER INFORMATION: Xaa is selected from A and C

<400> SEQUENCE: 113

Phe Asn Lys Asp Pro Ser Gln Ser Ala Asn Leu Leu Xaa Glu Ala Lys
1               5                   10                  15

Lys Leu Asn Asp Ala Gln Ala Pro
            20

<210> SEQ ID NO 114
<211> LENGTH: 29
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (7)..(8)
<223> OTHER INFORMATION: HER3 binding motif

<400> SEQUENCE: 114

Ala Asp Asn Asn Phe Asn Lys Asp Pro Ser Gln Ser Ala Asn Leu Leu
1               5                   10                  15

Ser Glu Ala Lys Lys Leu Asn Glu Ser Gln Ala Pro Lys
            20                  25

<210> SEQ ID NO 115
<211> LENGTH: 29
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (7)..(8)
<223> OTHER INFORMATION: HER3 binding motif

<400> SEQUENCE: 115

Ala Asp Asn Lys Phe Asn Lys Asp Pro Ser Gln Ser Ala Asn Leu Leu

-continued

```
                1               5                  10                 15
Ala Glu Ala Lys Lys Leu Asn Asp Ala Gln Ala Pro Lys
            20                  25
```

<210> SEQ ID NO 116
<211> LENGTH: 29
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (7)..(8)
<223> OTHER INFORMATION: HER3 binding motif

<400> SEQUENCE: 116

```
Ala Asp Asn Lys Phe Asn Lys Asp Pro Ser Val Ser Lys Glu Ile Leu
1               5                   10                  15
Ala Glu Ala Lys Lys Leu Asn Asp Ala Gln Ala Pro Lys
            20                  25
```

<210> SEQ ID NO 117
<211> LENGTH: 32
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (10)..(11)
<223> OTHER INFORMATION: HER3 binding motif

<400> SEQUENCE: 117

```
Ala Asp Ala Gln Gln Asn Asn Phe Asn Lys Asp Pro Ser Gln Ser Thr
1               5                   10                  15
Asn Val Leu Gly Glu Ala Lys Lys Leu Asn Glu Ser Gln Ala Pro Lys
            20                  25                  30
```

<210> SEQ ID NO 118
<211> LENGTH: 27
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (5)..(6)
<223> OTHER INFORMATION: HER3 binding motif

<400> SEQUENCE: 118

```
Ala Gln His Asp Glu Asp Pro Ser Gln Ser Ala Asn Val Leu Gly Glu
1               5                   10                  15
Ala Gln Lys Leu Asn Asp Ser Gln Ala Pro Lys
            20                  25
```

<210> SEQ ID NO 119
<211> LENGTH: 29
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (7)..(8)
<223> OTHER INFORMATION: HER3 binding motif

<400> SEQUENCE: 119

Val Asp Asn Lys Phe Asn Lys Asp Pro Ser Gln Ser Ala Asn Leu Leu
1               5                   10                  15

Ala Glu Ala Lys Lys Leu Asn Asp Ala Gln Ala Pro Lys
                20                  25

<210> SEQ ID NO 120
<211> LENGTH: 29
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (7)..(8)
<223> OTHER INFORMATION: HER3 binding motif

<400> SEQUENCE: 120

Val Asp Ala Lys Tyr Ala Lys Asp Pro Ser Gln Ser Ser Glu Leu Leu
1               5                   10                  15

Ala Glu Ala Lys Lys Leu Asn Asp Ala Gln Ala Pro Lys
                20                  25

<210> SEQ ID NO 121
<211> LENGTH: 29
<212> TYPE: PRT
<213> ORGANISM: Artificial Sequence
<220> FEATURE:
<223> OTHER INFORMATION: Engineered HER3 Binding Polypeptide
<220> FEATURE:
<221> NAME/KEY: MISC_FEATURE
<222> LOCATION: (7)..(8)
<223> OTHER INFORMATION: HER3 binding motif

<400> SEQUENCE: 121

Ala Glu Ala Lys Tyr Ala Lys Asp Pro Ser Glu Ser Ser Glu Leu Leu
1               5                   10                  15

Ser Glu Ala Lys Lys Leu Asn Lys Ser Gln Ala Pro Lys
                20                  25

<210> SEQ ID NO 122
<211> LENGTH: 8
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(1)
<223> OTHER INFORMATION: Z variant

<400> SEQUENCE: 122

Leu Glu His His His His His His
1               5

<210> SEQ ID NO 123
<211> LENGTH: 10
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: Z variant
<220> FEATURE:
<221> NAME/KEY: MISC_FEATURE
<222> LOCATION: (10)..(10)
<223> OTHER INFORMATION: albumin binding domain

<400> SEQUENCE: 123

Met Gly Ser Ser Leu Gln Val Asp Ser Ser
1               5                   10

<210> SEQ ID NO 124
<211> LENGTH: 20
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(2)
<223> OTHER INFORMATION: Z variant
<220> FEATURE:
<221> NAME/KEY: MISC_FEATURE
<222> LOCATION: (11)..(12)
<223> OTHER INFORMATION: albumin binding domain
<220> FEATURE:
<221> NAME/KEY: MISC_FEATURE
<222> LOCATION: (20)..(20)
<223> OTHER INFORMATION: Z variant

<400> SEQUENCE: 124

Met Gly Ala Pro Gly Gly Gly Ser Thr Ser Gly Thr Gly Gly
1               5                   10                  15

Gly Ser Pro Arg
            20

<210> SEQ ID NO 125
<211> LENGTH: 50
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(2)
<223> OTHER INFORMATION: Z variant
<220> FEATURE:
<221> NAME/KEY: MISC_FEATURE
<222> LOCATION: (26)..(27)
<223> OTHER INFORMATION: albumin binding domain
<220> FEATURE:
<221> NAME/KEY: MISC_FEATURE
<222> LOCATION: (50)..(50)
<223> OTHER INFORMATION: Z variant

<400> SEQUENCE: 125

Met Gly Ala Pro Gly Gly Gly Ser Gly Gly Gly Ser Gly Gly
1               5                   10                  15

Gly Gly Ser Gly Gly Gly Ser Thr Ser Gly Thr Gly Gly Gly
                20                  25                  30

Ser Gly Gly Gly Ser Gly Gly Gly Ser Gly Gly Gly Gly Ser
            35                  40                  45

Pro Arg
    50

<210> SEQ ID NO 126
<211> LENGTH: 10
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(1)
<223> OTHER INFORMATION: Z variant
<220> FEATURE:

```
<221> NAME/KEY: MISC_FEATURE
<222> LOCATION: (5)..(6)
<223> OTHER INFORMATION: albumin binding domain
<220> FEATURE:
<221> NAME/KEY: MISC_FEATURE
<222> LOCATION: (10)..(10)
<223> OTHER INFORMATION: Z variant

<400> SEQUENCE: 126

Gly Gly Gly Gly Ser Gly Gly Gly Gly Ser
1               5                   10

<210> SEQ ID NO 127
<211> LENGTH: 38
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(1)
<223> OTHER INFORMATION: Z variant
<220> FEATURE:
<221> NAME/KEY: MISC_FEATURE
<222> LOCATION: (20)..(21)
<223> OTHER INFORMATION: albumin binding domain
<220> FEATURE:
<221> NAME/KEY: MISC_FEATURE
<222> LOCATION: (40)..(40)
<223> OTHER INFORMATION: Z variant

<400> SEQUENCE: 127

Gly Gly Gly Gly Ser Gly Gly Ser Gly Gly Gly Ser Gly Gly
1               5                   10                  15

Gly Gly Ser Gly Gly Gly Gly Ser Gly Gly Ser Gly Gly Gly Gly
                20                  25                  30

Ser Gly Gly Gly Gly Ser
        35

<210> SEQ ID NO 128
<211> LENGTH: 6
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(6)
<223> OTHER INFORMATION: Z variant Z08699

<400> SEQUENCE: 128

His Glu His Glu His Glu
1               5

<210> SEQ ID NO 129
<211> LENGTH: 6
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(6)
<223> OTHER INFORMATION: Z variant Z08698

<400> SEQUENCE: 129

His Glu His Glu His Glu
1               5
```

```
<210> SEQ ID NO 130
<211> LENGTH: 6
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(6)
<223> OTHER INFORMATION: Z variant Z08698 derivatized with 1,4,7-
      triazacyclononane-N,N',N''-triacetic acid (NOTA)

<400> SEQUENCE: 130

His Glu His Glu His Glu
1               5

<210> SEQ ID NO 131
<211> LENGTH: 6
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(6)
<223> OTHER INFORMATION: Z Variant Z08699 derivatized with
      1,4,7-triazacyclononane-N,N',N''-triacetic acid (NOTA)

<400> SEQUENCE: 131

His Glu His Glu His Glu
1               5

<210> SEQ ID NO 132
<211> LENGTH: 6
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(1)
<223> OTHER INFORMATION: In-111 labelled
<220> FEATURE:
<221> NAME/KEY: MISC_FEATURE
<222> LOCATION: (7)..(7)
<223> OTHER INFORMATION: Z variant Z08698 derivatized with
      1,4,7-triazacyclononane-N,N',N''-triacetic acid (NOTA)

<400> SEQUENCE: 132

His Glu His Glu His Glu
1               5

<210> SEQ ID NO 133
<211> LENGTH: 6
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (1)..(1)
<223> OTHER INFORMATION: In-111
<220> FEATURE:
<221> NAME/KEY: MISC_FEATURE
<222> LOCATION: (6)..(6)
<223> OTHER INFORMATION: Z variant Z08699 derivatized with
      1,4,7-triazacyclononane-N,N',N''-triacetic acid (NOTA)

<400> SEQUENCE: 133

His Glu His Glu His Glu
1               5
```

HER3 BINDING POLYPEPTIDES

This application is a U.S. National Stage Application of PCT/EP2013/070605 filed Oct. 3, 2013, which claims priority to U.S. Provisional Patent Application No. 61/710,051, filed Oct. 5, 2012, European Patent Application No. 12187457.2 filed Oct. 5, 2012, U.S. Provisional Patent Application No. 61/753,963 filed Jan. 18, 2013 and European Patent Application No. 13151882.1 filed Jan. 18, 2013. All of these applications are incorporated by reference in their entireties.

FIELD OF THE INVENTION

The present disclosure relates to polypeptides which bind to human epidermal growth factor receptor 3 (herein referred to as HER3), and to use of such polypeptides in imaging and therapy.

BACKGROUND

The epidermal growth factor family of transmembrane tyrosine kinase receptors, including EGFR (ErbB1 or HER1), ErbB2 (HER2), ErbB3 (ERBB3 or HER3) and ErbB4 (HER4) are involved in regulating key cellular functions (e.g. cell proliferation, survival, differentiation and migration) through a complex network of intracellular signaling pathways. HER3 differs from the other receptors of this family due to its inactive tyrosine kinase domain, and hence signals via ligand-induced heterodimer formation with other tyrosine kinase receptors (Guy et al, Proc Natl Acad Sci 91: 8132-8136 (1994); Sierke et al, Biochem J 322 (Pt 3): 757-763 (1997)). As a result, the implication of this receptor in tumor progression has long been a mystery. Recently, however, HER3 has gained interest as an allosteric kinase activator of its family members. Especially the heterodimer formed by HER2 and HER3 is said to be an exceptionally strong activator of downstream intracellular signaling (Jura et al, Proc Natl Acad Sci 106: 21608-21613 (2009); Citri et al, Exp Cell Res 284: 54-65 (2003)). This HER2-HER3 signaling pair has even been suggested as an oncogenic unit in HER2-driven breast cancer (Holbro T, et al, Proc Natl Acad Sci 100: 8933-8938 (2003)). In addition, up-regulation of the HER3 receptor has been shown to play an important role for the resistance to tyrosine kinase inhibitors in breast cancers overexpressing HER2 in vitro and in vivo (Sergina et al, Nature 445: 437-441 (2007); Kong et al, PLoS One 3: e2881 (2008); Garrett et al, Proc Natl Acad Sci 108: 5021-5026 (2011)).

However, the importance of HER3 in human cancers is not limited to HER2-driven breast cancers. HER3 has also been shown to be required for tumorigenicity of HER3-overexpressing prostate cancer xenografts in vivo, to maintain in vivo proliferation of a subset of ovarian cancers via an autocrine signaling loop, and to be involved in endocrine resistance of ER+ breast cancer cell lines, to name a few examples (Soler et al, Int J Cancer 125: 2565-2575 (2009); Sheng Q et al, Cancer Cell 17: 412-412 (2010); Liu et al, Int J Cancer 120: 1874-1882 (2007); Frogne et al, Breast Cancer Res Treat 114: 263-275 (2009)). Altogether, these findings demonstrate the potential of the HER3-signaling pathway as an important therapeutic target in human cancers. In addition, HER3 expression has a prognostic value, since high levels of receptor expression are associated with significantly shorter survival time compared with patients that overexpress HER2 (Tanner et al, J Clin Oncol 24(26):4317-23 (2006), Reschke et al, Clin Cancer Res 14(16):5188-97 (2008)).

A relatively large fraction of recently approved therapies directed towards the EGFR and HER2 receptors is based on monoclonal antibodies. In contrast to the well investigated EGFR and HER2 receptor members of the ErbB-family, there are relatively few reports on the use of anti-HER3 antibodies. Ullrich and co-workers have reported that anti-HER3 monoclonal antibodies inhibit HER3 mediated signaling in cell models of breast cancer (van der Horst et al, Int J Cancer 115(4):519-27 (2005)). However, although several successful cancer therapy studies have been reported using full-length monoclonal antibodies, this class of agents is not always optimal for targeting solid tumors (neither for diagnostic nor for therapeutic pay-load purposes). Therapeutic effect is dependent on an efficient distribution of the drug throughout the tumor, and molecular imaging depends on a high ratio between tumor uptake and surrounding normal tissue. Since tumor penetration rate (including extravasation) is negatively associated with the size of the molecule, the relatively large antibody molecule (e.g. IgG) inherently has poor tissue distribution and penetration capacity. Moreover, for molecular imaging, the extraordinarily long in vivo half-life of antibodies results in relatively high blood signals and thereby relatively poor tumor-to-blood contrasts.

Recently, much smaller HER3-specific molecules based on the three-helical bundle scaffold of the Z domain, derived from domain B of Protein A from *Staphylococcus aureus*, were generated using combinatorial protein engineering (Kronqvist et al, Protein Eng Des Sel 24: 385-396 (2010); WO2011/056124). These Z variants, with subnanomolar affinities for HER3, demonstrated anti-proliferative effects through blockage of ligand-induced HER3-signalling of breast cancer cell lines in vitro (Gostring et al, PLoS One 7:e40023 (2012)). These growth-inhibitory effects were further demonstrated to be a result of competitional HER3 binding between the Z variant molecules and the ligand heregulin.

However, in vivo targeting of the HER3 receptor may be challenging, due to relatively low expression of the receptor on tumor cells. Typical expression levels of $10^3$ to $10^4$ receptors per cell have been reported (Aguilar et al, Oncogene 18: 6050-6062 (1999); Robinson et al, Br J Cancer 99: 1415-1425 (2008)). In addition to a high tumor uptake, a prolonged retention in the tumor is of great importance for efficient therapeutic effects of a drug. Small targeting agents, such as polypeptides derived from the Z domain, have the ability to accumulate at high levels in tumors due to high vascular permeability and rapid diffusivity into the tumor (Schmidt and Wittrup, Mol Cancer Ther 8: 2861-2871 (2009)). However, unbound proteins of low molecular weight will be cleared rapidly from the tumor and then from the circulation via the kidneys. As a consequence, a high affinity of a small-size targeting agent towards the cancer cell is of great importance for increased tumor retention. Furthermore, for efficient targeting of a receptor protein with low expression ($10^4$ target proteins, or less, per cell), recent results suggest that the affinity of small polypeptides (for example polypeptides derived from the Z domain) should be as high as possible, preferably with a binding constant, $K_D$, in the low picomolar range or less (Tolmachev et al (2012), J Nucl Med 53(6):953-60).

Since HER3 may be expressed on the same tumor cell as other members of the EGF family, production of bispecific molecules targeting HER3 and another member of the EGF family has recently attracted some interest. Such bispecific molecules could for example be utilized as targeting vehicles for increasing the specificity of targeting in molecular imaging applications and simultaneously targeting HER3 and another antigen expressed on tumors.

DESCRIPTION OF THE INVENTION

It is an object of the present disclosure to provide a novel group of HER3 binding agents, which bind HER3 with a high affinity.

It is another object of the present disclosure to provide a novel group of HER3 binding agents, which for example may be used in targeting HER3 expressing cells, molecular imaging of such HER3 expressing cells and/or treatment of HER3 related conditions.

Another object of the present disclosure is to provide a defined group of HER3 binding agents, which group differs from the groups of HER3 binding polypeptides previously defined in WO2011/056124.

Thus, according to one aspect of the invention, there is provided a HER3 binding polypeptide, comprising a HER3 binding motif (BM), which motif consists of an amino acid sequence selected from i) EKYX$_4$AYX$_7$EIW X$_{11}$LPNLTX$_{17}$X$_{18}$QX$_{20}$ AAFIGX$_{26}$LX$_{28}$D (SEQ ID NO: 110):

wherein, independently of each other,

X$_4$ is selected from A, E, L, M, N Q, R, S and T;
X$_7$ is selected from F and Y;
X$_{11}$ is selected from E and Q;
X$_{17}$ is selected from K, N, R and V;
X$_{18}$ is selected from F, M, N, R, T, Y and W;
X$_{20}$ is selected from A and K;
X$_{26}$ is selected from K and S;
X$_{28}$ is selected from E and Q; and ii) an amino acid sequence which has at least 96% identity to the sequence defined in i).

The above definition of a class of sequence related HER3 binding polypeptides is based on the analysis of sequences of several novel polypeptide variants, selected from a library that was designed based on sequences previously shown to exhibit HER3 binding and disclosed in WO2011/056124. These polypeptides, in turn, were random variants of a parent scaffold derived from one of the domains of staphylococcal protein A.

The identified HER3 binding motif, or "BM", corresponds to the target binding region of the parent scaffold, which region constitutes two alpha helices within a three-helical bundle protein domain. In the parent scaffold, the varied amino acid residues of the two BM helices constitute a binding surface for interaction with the constant Fc part of antibodies. By random variation of binding surface residues and subsequent selection of variants, the Fc interaction capacity of the binding surface was originally replaced with a capacity for interaction with HER3 as described in WO2011/056124. In the work leading to the present disclosure, new sequences were generated which show unexpectedly superior properties, for example in connection with affinity parameters suitable for molecular imaging.

As the skilled person will realize, the function of any polypeptide, such as the HER3 binding capacity of the polypeptides as defined herein, is dependent on the tertiary structure of the polypeptide. It is therefore possible to make minor changes to the amino acid sequence of a polypeptide without largely affecting the tertiary structure and the function thereof.

Thus, in one embodiment, the polypeptide comprises modified variants of the BM of sequence i), which are such that the resulting sequence is at least 96% identical to a sequence belonging to the class defined by sequence i). In some embodiments, such changes may be made in all positions of the sequences of the HER3 binding polypeptides as disclosed herein. In other embodiments, such changes may be made only in the non-variable positions, also denoted as scaffold amino acid residues. In such cases, changes are not allowed in the variable positions, i.e. positions denoted with an "X" (e.g. X$_4$, X$_7$, X$_{11}$, X$_{17}$, X$_{18}$, X$_{20}$, X$_{26}$ and X$_{28}$ of the above defined BM). For example, it is possible that an amino acid residue belonging to a certain functional grouping of amino acid residues (e.g. hydrophobic, hydrophilic, polar etc) could be exchanged for another amino acid residue from the same functional group.

The term "% identity", as used throughout the specification, may be calculated as follows. The query sequence is aligned to the target sequence using the CLUSTAL W algorithm (Thompson et al, Nucleic Acids Research, 22: 4673-4680 (1994)). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared, and the percentage of positions in the query sequence that have identical correspondences in the target sequence is reported as % identity.

In one embodiment, the invention provides a HER3 binding polypeptide as defined above, in which, in sequence i), independently of each other, X$_4$ is selected from A, E, M, N, Q, S and T;
X$_7$ is selected from F and Y;
X$_{11}$ is Q;
X$_{17}$ is selected from K and R;
X$_{18}$ is selected from M, Y and W;
X$_{20}$ is K;
X$_{26}$ is K;
X$_{28}$ is Q.

In one embodiment, X$_4$ in sequence i) is selected from A, E, M, N, Q, S and T. In a more specific embodiment, X$_4$ in sequence i) is selected from N and Q. In an even more specific embodiment, X$_4$ in sequence i) is N. In another embodiment, X$_4$ in sequence i) is Q.

In one embodiment, X$_{11}$ in sequence i) is Q.

In one embodiment, X$_{17}$ in sequence i) is selected from K, N and R. In another embodiment, X$_{17}$ in sequence i) is selected from K and R. In a more specific embodiment, X$_{17}$ in sequence i) is K. In another embodiment, X$_{17}$ in sequence i) is R.

In one embodiment, X$_{18}$ in sequence i) is selected from M, Y and W. In a more specific embodiment, X$_{18}$ in sequence i) is selected from Y and W. In an even more specific embodiment, X$_{18}$ in sequence i) is Y. In another embodiment, X$_{18}$ in sequence i) is W. In another embodiment, X$_{18}$ in sequence i) is M.

In one embodiment, X$_{17}$X$_{18}$ in sequence i) is selected from KW, KY, KM and RY.

In one embodiment, X$_{20}$ in sequence i) is K.
In one embodiment, X$_{26}$ in sequence i) is K.
In one embodiment, X$_{28}$ in sequence i) is Q.

In one embodiment, sequence i) fulfills at least two of the following four conditions I, II, III and IV:

I) X$_{ii}$ is Q;
II) X$_{17}$X$_{18}$ is selected from KW, KY, KM and RY;
III) X$_{20}$ is K;
IV) X$_{28}$ is Q.

In more specific embodiments, the sequence i) fulfills at least three, such as at all four, of the conditions I, II, III and IV.

As described in detail in the experimental section to follow, the selection of HER3 binding variants led to the identification of individual HER3 binding motif (BM) sequences. These sequences constitute individual embodiments of HER3 binding polypeptides according to this aspect. The sequences of individual HER3 binding motifs are presented in FIG. 1 and as SEQ ID NO:1-35. Thus, in some embodiments of this aspect, there is provided a HER3 binding polypeptide, wherein the BM sequence i) is selected from any one of SEQ ID NO:1 to SEQ ID NO:35, such as from any one of SEQ ID NO:1-10, such as from SEQ ID NO:1-2. In one particular embodiment, said sequence is SEQ ID NO:2. In another particular embodiment, said sequence is SEQ ID NO:1.

In some embodiments of the present disclosure, the BM as defined above "forms part of" a three-helix bundle protein domain. This is understood to mean that the sequence of the BM is "inserted" into or "grafted" onto the sequence of the original three-helix bundle domain, such that the BM replaces a similar structural motif in the original domain. For example, without wishing to be bound by theory, the BM is thought to constitute two of the three helices of a three-helix bundle, and can therefore replace such a two-helix motif within any three-helix bundle. As the skilled person will realize, the replacement of two helices of the three-helix bundle domain by the two BM helices has to be performed so as not to affect the basic structure of the polypeptide. That is, the overall folding of the Cα backbone of the polypeptide according to this embodiment of the invention is substantially the same as that of the three-helix bundle protein domain of which it forms a part, e.g. having the same elements of secondary structure in the same order etc. Thus, a BM according to the invention "forms part" of a three-helix bundle domain if the polypeptide according to this embodiment of the invention has the same fold as the original domain, implying that the basic structural properties are shared, those properties e.g. resulting in similar CD spectra. The skilled person is aware of other parameters that are relevant.

In particular embodiments, the HER3 binding motif (BM) thus forms part of a three-helix bundle protein domain. For example, the BM may essentially constitute two alpha helices with an interconnecting loop, within said three-helix bundle protein domain. In particular embodiments, said three-helix bundle protein domain is selected from domains of bacterial receptor proteins. Non-limiting examples of such domains are the five different three-helical domains of Protein A from *Staphylococcus aureus*, such as domain B, and derivatives thereof. In some embodiments, the three-helical bundle protein domain is a variant of protein Z, which is derived from domain B of staphylococcal protein A.

In embodiments where the HER3 binding polypeptide of the invention forms part of a three-helix bundle protein domain, the HER3 binding polypeptide may comprise an amino acid sequence selected from:

iii) K-[BM]-DPSQS $X_aX_bLLX_c$ EAKKL $NDX_dQ$ (SEQ ID NO: 111);
wherein
  [BM] is a HER3 binding motif as defined above;
  $X_a$ is selected from A and S;
  $X_b$ is selected from N and E;
  $X_c$ is selected from A, S and C;
  $X_d$ is selected from A and S; and
iv) an amino acid sequence which has at least 89% identity to any one of the sequences defined in iii).

Said amino acid sequence iv) may have at least 91%, such as at least 93%, such as at least 95%, such as at least 97% identity to any one of the sequences defined in iii).

In one embodiment of the HER3 binding polypeptide as defined above, $X_a$ in sequence iii) is A. In an alternative embodiment of the HER3 binding polypeptide as defined above, $X_a$ in sequence iii) is S.

In one embodiment of the HER3 binding polypeptide as defined above, $X_b$ in sequence iii) is N. In an alternative embodiment, $X_b$ in sequence iii) is E.

In one embodiment of the HER3 binding polypeptide as defined above, $X_c$ in sequence iii) is A. In an alternative embodiment, $X_c$ in sequence iii) is S. In yet another alternative embodiment, $X_c$ in sequence iii) is C.

In one embodiment of the HER3 binding polypeptide as defined above, $X_d$ in sequence iii) is A. In an alternative embodiment, $X_d$ in sequence iii) is S.

In one embodiment of the HER3 binding polypeptide as defined above, $X_a$ is A; $X_b$ is N; $X_c$ is A and $X_d$ is A, in sequence iii).

In a further embodiment of the HER3 binding polypeptide as defined above, $X_a$ is A; $X_b$ is N; $X_c$ is C and $X_d$ is A, in sequence iii).

In a further embodiment of the HER3 binding polypeptide as defined above, $X_a$ is S; $X_b$ is E; $X_c$ is S and $X_d$ is S, in sequence iii).

In a further embodiment of the HER3 binding polypeptide as defined above, $X_a$ is S; $X_b$ is E; $X_c$ is C and $X_d$ is S, in sequence iii).

In yet a further embodiment, sequence iii) in the definition above of a HER3 binding polypeptide according to the invention is selected from SEQ ID NO:36-70, in particular from SEQ ID NO:36-45, such as from SEQ ID NO:36 and SEQ ID NO:37. In a specific embodiment, sequence iii) is SEQ ID NO:37. In another specific embodiment, sequence iii) is SEQ ID NO:36.

Also, in a further embodiment, there is provided a HER3 binding polypeptide as defined above, which comprises an amino acid sequence selected from:

v) YAK-[BM]-DPSQS SELL$X_c$ EAKKL NDSQA P (SEQ ID NO: 112); wherein [BM] is a HER3 binding motif as defined above and $X_c$ is selected from S and C; and
vi) an amino acid sequence which has at least 90% identity to the sequence defined in v).

In another embodiment, there is provided a HER3 binding polypeptide which comprises an amino acid sequence selected from (SEQ ID NO: 113):
vii) FNK-[BM]-DPSQS ANLL$X_c$ EAKKL NDAQA P; wherein [BM] is a HER3 binding motif as defined above and $X_c$ is selected from A and C; and
viii) an amino acid sequence which has at least 90% identity to any one of the sequences defined in vii) above.

As discussed above, polypeptides comprising minor changes as compared to the above amino acid sequences without largely affecting the tertiary structure and the function thereof are also within the scope of the present disclosure. Thus, in some embodiments, the HER3 binding polypeptides as defined above may for example have a sequence which is at least 92%, at least 94%, at least 96%, or at least 98% identical to a sequence defined by v) or vii).

In some embodiments and as disclosed in the Examples below, the HER3 binding motif may form part of a polypeptide which comprises an amino acid sequence selected from
ADNNFNK-[BM]-DPSQSANLLSEAKKLNESQAPK; (SEQ ID NO: 114)

ADNKFNK-[BM]-DPSQSANLLAEAKKLNDAQAPK; (SEQ ID NO: 115)
ADNKFNK-[BM]-DPSVSKEILAEAKKLNDAQAPK; (SEQ ID NO: 116)
ADAQQNNFNK-[BM]-DPSQSTNVLGEAKKL-NESQAPK; (SEQ ID NO: 117)
AQHDE-[BM]-DPSQSANVLGEAQKLNDSQAPK; (SEQ ID NO: 118)
VDNKFNK-[BM]-DPSQSANLLAEAKKLNDAQAPK; (SEQ ID NO: 119)
VDAKYAK-[BM]-DPSQSSELLAEAKKLNDAQAPK; (SEQ ID NO: 120) and
AEAKYAK-[BM]-DPSESSELLSEAKKLNKSQAPK; (SEQ ID NO: 121) wherein [BM] is a HER3 binding motif as defined above.

In one embodiment, the HER3 binding polypeptide comprises an amino acid sequence selected from:

ix) AEAKYAK-[BM]-DPSESSELLSEAKKLNKSQAPK; (SEQ ID NO: 121) wherein [BM] is a HER3 binding motif as defined above, and x) an amino acid sequence which has at least 91% identity to the sequence defined in ix).

Again, polypeptides comprising minor changes as compared to the above amino acid sequences without largely affecting the tertiary structure and the function thereof are also within the scope of the present disclosure. Thus, in some embodiments, the HER3 binding polypeptides as defined above may for example have a sequence which is at least 93%, at least 94%, at least 96%, or at least 98% identical to the sequence defined by ix).

Sequence ix) in such a polypeptide may be selected from any one of SEQ ID NO:71-105. In particular, sequence ix) may be selected from any one of SEQ ID NO:71-80, such as selected from SEQ ID NO:71-72. In a specific embodiment of this polypeptide, sequence ix) is SEQ ID NO:72. In another specific embodiment, sequence ix) is SEQ ID NO:71.

The HER3 binding polypeptide of the class defined above exhibits advantageous binding properties in comparison to the previously known general group of HER3 binding polypeptides (i.e. those presented in WO2011/056124). In particular, in one embodiment of the HER3 binding polypeptide of the present disclosure, the off-rate ($k_{off}$) of the interaction between said HER3 binding polypeptide and human HER3 is at least four-fold reduced, when compared to the off-rate ($k_{off}$) of the interaction between a comparative HER3 binding polypeptide comprising the amino acid sequence SEQ ID NO:107 and human HER3, as measured using the same experimental conditions. In another embodiment, the HER3 binding polypeptide defined herein is such that said off-rate ($k_{off}$) is at least 8-fold reduced, such as at least 12-fold reduced, such as at least 15-fold reduced in comparison to that of the HER3 binding polypeptide comprising SEQ ID NO:107. In a more specific embodiment, said off-rate ($k_{off}$) is at least 20-fold reduced in comparison to that of the HER3 binding polypeptide comprising SEQ ID NO:107.

In one embodiment of the HER3 binding polypeptide according to the present disclosure, the interaction between said HER3 binding polypeptide and human HER3 is such that the $K_D$ value of the interaction is at most $1 \times 10^{-9}$ M, such as at most $1 \times 10^{-10}$ M, such as at most $1 \times 10^{-11}$ M.

These kinetic parameters, and others, may for example be measured qualitatively and quantitatively using surface plasmon resonance in a Biacore® or Proteon XPR instrument, and/or using fluorescence activated cell sorting as in the examples which follow.

The skilled person will understand that various modifications and/or additions can be made to a HER3 binding polypeptide according to any aspect disclosed herein in order to tailor the polypeptide to a specific application without departing from the scope of the present disclosure. For example, any HER3 binding polypeptide disclosed herein may comprise further C terminal and/or N terminal amino acids. Such a polypeptide should be understood as a polypeptide having additional amino acid residues at the very first and/or the very last position in the polypeptide chain, i.e. at the N- and/or C-terminus. Thus, in one embodiment, the HER3 binding polypeptide as defined herein may comprise any suitable number of additional amino acid residues, for example at least one additional amino acid residue. Each additional amino acid residue may individually or collectively be added in order to, for example, improve production, purification, stabilization in vivo or in vitro, coupling, or detection of the polypeptide. Such additional amino acid residues may comprise one or more amino acid residues added for the purpose of chemical coupling. One example of this is the addition of a cysteine residue. Such additional amino acid residues may also provide a "tag" for purification or detection of the polypeptide, such as a $His_6$ tag, HEHEHE tag or a "myc" (c-myc) tag or a "FLAG" tag for interaction with antibodies specific to the tag or immobilized metal affinity chromatography (IMAC) in the case of the $His_6$-tag and the HEHEHE tag.

The further amino acids as discussed above may be coupled to the HER3 binding polypeptide by means of chemical conjugation (using known organic chemistry methods) or by any other means, such as expression of the HER3 binding polypeptide as a fusion protein.

The further amino acids as discussed above may for example comprise one or more polypeptide domain(s).

A further polypeptide domain may provide the HER3 binding polypeptide with another function, such as for example another binding function, or an enzymatic function, or a toxic function (e.g. an immunotoxin), or a fluorescent signaling function, or a therapeutic function, or a diagnostic function, or a prognostic function, or combinations thereof.

A further polypeptide domain may moreover provide the HER3 binding polypeptide with the same binding function. Thus, a HER3 binding polypeptide as disclosed herein may comprise at least two HER3 binding polypeptide monomer units, the amino acid sequences of which may be the same or different. Multimeric forms of the polypeptides may comprise a suitable number of domains, each having a HER3 binding motif, and each forming a "monomer" within the multimer. These domains may all have the same amino acid sequence, but alternatively, they may have different amino acid sequences. In particular, the HER3 binding polypeptide as disclosed herein may form homo- or heterodimers.

In other words, in a second aspect of the present disclosure, there is provided a fusion protein or conjugate comprising a first moiety consisting of a HER3 binding polypeptide as described herein; and a second moiety consisting of a polypeptide having a desired biological activity. Examples of desired biological activities include, but are not limited to, therapeutic activity, binding activity, diagnostic activity, prognostic activity and enzymatic activity, as well as combinations thereof.

In one embodiment, said second moiety is selected from the group consisting of human endogenous enzymes, hormones, growth factors, chemokines, cytokines and lymphokines. In another embodiment, said second moiety is a binding polypeptide capable of selective interaction with a target molecule, such as a target molecule selected from the group consisting of albumin, HER3, HER2, EGFR, IGF1R, cMet, VEGFR and PDGFR. Thus, the second or further moeities may provide the HER3 binding polypeptide with another binding function. Alternatively, said second or further moeities may provide the HER3 binding polypeptide with another HER3 binding function. Hence, multimeric forms (such as, but not limited to dimeric, trimeric and tetrameric forms) of the HER3 binding polypeptides fall within the scope of said disclosure. As stated above, the multimer units may all have the same amino acid sequence, but alternatively, they may have different amino acid sequences.

As described above, the present disclosure also encompasses HER3 binding polypeptides, fusion proteins or conjugates comprising at least one HER3 binding polypeptide monomer unit and at least one monomer unit with a binding affinity for another target. Such other target may be selected from other epidermal growth factor receptors, such as in particular HER2 and EGFR, or if suitable from other targets, such as, but not limited to IGF1R, cMet, VEGFR and PDGFR. Such heteromultimeric forms of the polypeptide may comprise a suitable number of domains, having at least one HER3 binding motif, and a suitable number of domains with binding motifs conferring affinity to the one or more other target. See for example WO2011/056124 for a detailed discussion of the possibilities in this regard, which is equally relevant for the novel HER3 binding polypeptides presented herein.

A non-limiting list of contemplated binding polypeptides includes polypeptides selected from the group consisting of antibodies and fragments and domains thereof substantially retaining antibody binding activity; microbodies, maxybodies, avimers and other small disulfide-bonded proteins; and binding proteins derived from a scaffold selected from the group consisting of staphylococcal protein A and domains thereof, other three helix domains, lipocalins, ankyrin repeat domains, cellulose binding domains, γ crystallines, green fluorescent protein, human cytotoxic T lymphocyte-associated antigen 4, protease inhibitors such as Kunitz domains, PDZ domains, SH3 domains, peptide aptamers, staphylococcal nuclease, tendamistats, fibronectin type III domain, transferrin, zinc fingers and conotoxins.

Fusion proteins or conjugates according to the present disclosure, in which a HER3 binding polypeptide according to the invention constitutes a first moiety and the second and/or further moieties have other functions than binding HER3 also fall within the scope of this disclosure. The second and/or further moiety/moieties of the fusion polypeptide or conjugate may suitably have a desired biological activity. Hence, in one embodiment, there is provided a fusion protein or conjugate as described herein, comprising a further moiety consisting of a polypeptide having a further, desired biological activity, which may be the same as or different from that of the second moiety. Examples of fusion proteins or conjugates according to the present invention include fusion proteins or conjugates, wherein the second moiety has a therapeutic activity, binding activity, enzymatic activity, is a therapeutically active polypeptide or is selected from the group consisting of human endogenous enzymes, hormones, growth factors, chemokines, cytokines and lymphokines, and the further moiety is a binding polypeptide capable of selective interaction with a target molecule. In another example, the second and further moieties are binding polypeptides capable of selective interaction with a target molecule, wherein said target molecule may be the same or different.

In some embodiments, the second or further moiety/moieties may comprise a moiety which increases the half life of the HER3 binding polypeptide in vivo. As understood by the skilled person, increased, or extended, half life means slowed clearance of a particular molecule from blood. There are a number of known strategies for prolonging half life of a particular polypeptide in vivo, such as coupling to the Fc domain of an antibody (Fc conjugation) or coupling to albumin. Another example is coupling to a half life extending moiety, e.g. a peptide or protein, which will associate to serum albumin in vivo. In particular, the half life extending moiety may be an albumin binding moiety. An albumin binding moiety may e.g. consist of a naturally occurring polypeptide, or an albumin binding fragment thereof, or an engineered polypeptide. An engineered polypeptide may be derived from a naturally occurring starting polypeptide through subjecting it to protein engineering techniques, such as mutations and alterations in a site-directed or randomized approach, with a view to create novel or enhanced properties, such as binding affinity for a molecule such as albumin. Such an engineered albumin binding polypeptide may for example be a variant of a protein scaffold, which variant has been selected for its specific binding affinity for albumin. In a specific embodiment, the protein scaffold may be selected from domains of streptococcal Protein G or derivatives thereof, such as for example domain GA1, domain GA2 and domain GA3 of Protein G from *Streptococcus* strain G148, in particular domain GA3.

Accordingly, in one embodiment of the HER3 binding polypeptide, the further amino acids comprise an albumin binding domain (GA or ABD) of streptococcal protein G, or a derivative thereof. Non-limiting examples of albumin binding domains which may be comprised as a second and/or further moiety in a fusion protein or conjugate with the HER3 binding polypeptide described herein are disclosed in WO 2009/016043 and WO 2012/004384. Without wishing to be bound by theory, it is contemplated that such a fusion protein or conjugate binds to serum albumin in vivo, and benefits from its longer half life, which increases the net half life of the polypeptide itself (see e.g. WO91/01743). The pharmacokinetic profile of a HER3 binding polypeptide, fusion protein or conjugate comprising an albumin binding moiety as defined above thus resembles that of serum albumin when administered for example to a mammalian subject. ABD and derivatives thereof bind very strongly to human serum albumin (HSA), as well as to serum albumin from other species, such as mouse and rat.

ABD of streptococcal protein G, and known variants thereof, is approximately 46 amino acid long. Thus, when a HER3 binding polypeptide, fusion protein or conjugate as described herein comprises an ABD moiety or a derivative thereof, the overall size of the HER3 binding molecule is relatively small. When administered for example to a mammalian subject, such as a human subject, the albumin binding part of the HER3 binding molecule will associate non-covalently with serum albumin and the polypeptide may thereby benefit from decreased renal clearance and increased recirculation in epithelial cells. Furthermore, a HER3 binding polypeptide, fusion protein or conjugate comprising a half life extending moiety may not only display an extended half life in vivo, but also a reduced immunologic response in vivo, as compared to a polypeptide lacking a corresponding half life extending moiety (see e.g. WO 2005/097202).

With regard to the description herein of fusion proteins or conjugates incorporating an HER3 binding polypeptide according to the invention, it is to be noted that the designation of first, second and further moieties is made for clarity reasons to distinguish between HER3 binding polypeptide or polypeptides according to the invention on the one hand, and moieties exhibiting other functions on the other hand. These designations are not intended to refer to the actual order of the different domains in the polypeptide chain of the fusion protein or conjugate. Thus, for example, said first moiety may without restriction appear at the N-terminal end, in the middle, or at the C-terminal end of the fusion protein or conjugate.

The further polypeptide domain(s) as described above may be joined to the HER3 binding polypeptide by covalent coupling using known organic chemistry methods. Alternatively, the HER3 binding polypeptide comprising the further polypeptide domain(s) may be expressed as one or more fusion polypeptides, for example in a system for recombinant expression of polypeptides, or joined in any other fashion, either directly or via a linker, for example an amino acid linker. Non-limiting examples of useful amino acid linkers are selected from G, GS, $[G_2S]_n$, $[G_3S]_n$, $[G_4S]_n$, $GS[G_4S]_n$, wherein n is an integer between 1 and 7, such as between 1 and 2, $[S_2G]_m$, $[S_3G]_m$, $[S_4G]_m$, wherein m is an integer between 1 and 7, and VDGS.

The disclosure also encompasses embodiments of HER3 binding polypeptides according to the first aspect and fusion proteins or conjugates according to the second aspect, which further comprise a cytotoxic agent, such as a cytotoxic agent selected from the group consisting of auristatin, anthracycline, calicheamycin, combretastatin, doxorubicin, duocarmycin, the CC-1065 anti-tumorantibiotic, ecteinsascidin, geldanamycin, maytansinoid, methotrexate, mycotoxin, taxol, ricin, bouganin, gelonin, pseudomonas exotoxin 38 (PE38), diphtheria toxin (DT), and their analogues, and derivates thereof and combinations thereof.

In other embodiments, the disclosed HER3 binding polypeptide, fusion protein or conjugate, further comprises a label, such as a label selected from the group consisting of fluorescent dyes and metals, chromophoric dyes, chemiluminescent compounds and bioluminescent proteins, enzymes, radionuclides and particles, for example for purposes of detection of the polypeptide in vivo or in vitro.

Said label may be used for labeling the polypeptide directly, but indirect labeling is also contemplated. In some embodiments, the labeled HER3 binding polypeptide is present as a moiety in a fusion protein or conjugate also comprising a second moiety having a desired biological activity. The label may in some instances be coupled only to the HER3 binding polypeptide, and in some instances both to the HER3 binding polypeptide and to the second moiety of the conjugate or fusion protein. Furthermore, it is also possible that the label may be coupled to a second moiety only and not the HER3 binding moiety. Hence in yet another embodiment, there is provided an HER3 binding polypeptide, fusion protein or conjugate comprising a second moiety, wherein said label is coupled to the second moiety only. When reference is made to a labeled polypeptide, this should be understood as a reference to all aspects of polypeptides as described herein, including fusion proteins and conjugates comprising an HER3 binding polypeptide and a second and optionally further moieties.

Thus, a labeled polypeptide may contain only the HER3 binding polypeptide and for example a radionuclide suitable for medical imaging or suitable for therapy, which may be chelated or covalently coupled to the HER3 binding polypeptide. Alternatively, a labeled polypeptide or may contain the HER3 binding polypeptide, a radionuclide suitable for medical imaging or suitable and a second moiety such as a small molecule having a desired biological activity, for example a therapeutic efficacy.

Due to the strong association between the labeled polypeptide and HER3, a labeled polypeptide may be used visualize the presence of HER3 expressing cells, such as cells within a cancer tumor.

A majority of radionuclides have a metallic nature and metals are typically incapable of forming stable covalent bonds with elements presented in proteins and peptides. For this reason, labeling of proteins and peptides with radioactive metals is performed with the use of chelators, i.e. multidentate ligands, which form non-covalent compounds, called chelates, with the metal ions. In an embodiment of the albumin binding polypeptide, fusion protein or conjugate, the incorporation of a radionuclide is enabled through the provision of a chelating environment, through which the radionuclide may be coordinated, chelated or complexed to the polypeptide.

One example of a chelator is the polyaminopolycarboxylate type of chelator. Two classes of such polyaminopolycarboxylate chelators can be distinguished: macrocyclic and acyclic chelators.

In one embodiment, the HER3 binding polypeptide, fusion protein or conjugate comprises a chelating environment provided by a polyaminopolycarboxylate chelator conjugated to the HER3 binding polypeptide via a thiol group of a cysteine residue or an epsilon amine group of a lysine residue.

The most commonly used macrocyclic chelators for radioisotopes of indium, gallium, yttrium, bismuth, radioactinides and radiolanthanides are different derivatives of DOTA (1,4,7,10-tetraazacyclododecane-1,4,7,10-tetraacetic acid). In one embodiment, a chelating environment of the HER3 binding polypeptide, fusion protein or conjugate is provided by DOTA or a derivative thereof. More specifically, in one embodiment, the chelating polypeptides encompassed by the present disclosure are obtained by reacting the DOTA derivative 1,4,7,10-tetraazacyclododecane-1,4,7-trisacetic acid-10-maleimidoethylacetamide (maleimidomonoamide-DOTA) with said polypeptide.

Additionally, 1,4,7-triazacyclononane-1,4,7-triacetic acid (NOTA) and derivatives thereof may be used as chelators. Hence, in one embodiment, there is provided a HER3 binding polypeptide, fusion protein or conjugate, wherein the polyaminopolycarboxylate chelator is 1,4,7-triazacyclononane-1,4,7-triacetic acid or a derivative thereof.

The most commonly used acyclic polyaminopolycarboxylate chelators are different derivatives of DTPA (diethylenetriamine-pentaacetic acid). Hence, polypeptides having a chelating environment provided by diethylenetriaminepentaacetic acid or derivatives thereof are also encompassed by the present disclosure.

In one embodiment there is provided a HER3 binding polypeptide, fusion protein or conjugate as described herein comprising a radionuclide suitable for medical imaging, said radionuclide being selected from the group consisting of $^{99m}$Tc, $^{61}$Cu, $^{64}$Cu, $^{66}$Ga, $^{67}$Ga, $^{68}$Ga, $^{110m}$In, $^{111}$In, $^{44}$Sc and $^{86}$Y, or with a radionuclide suitable for therapy, said radionuclide being selected from the group consisting of $^{225}$Ac, $^{212}$Bi, $^{213}$Bi, $^{67}$Cu, $^{166}$Ho, $^{177}$Lu, $^{212}$Pb, $^{149}$Pm, $^{153}$Sm, $^{227}$Th and $^{90}$Y, wherein the radionuclide is complexed with the HER3 binding polypeptide via a chelating environment. In one particular embodiment, the radionuclide is selected from the group consisting of $^{99m}$Tc, $^{111}$In, $^{64}$Cu and $^{68}$Ga. In one embodiment, the radionuclide is selected from $^{99m}$Tc and $^{111}$In.

The use of NOTA provides stable labeling of Z polypeptides with $^{111}$In for SPECT (Tolmachev et al, Bioconjug Chem 22: 894-902 (2011); Hescamp et al, J Nucl Med 53:143-153 (2012)), and $^{68}$Ga or $^{18}$F (using $^{18}$F-AlF chemistry (McBride et al, J Nucl Med 50:991-8 (2009))) for PET (Hescamp et al, supra). Besides, the same chelator might be used for stable labeling with the long-lived positron emitter $^{64}$Cu (Prasanphanich et al, Proc Nat Acad Sci 104:12462-7 (2007), Fournier et al, EJNMMI Res 2:8 (2012)), if an optimal imaging time would be more than 6 h after injection.

Additionally, a skilled person could also foresee a number of other chelators, capable to chelate such cores as "naked" Me, Me═O, O═Me═O, Me═N, Me(CO)3, or HYNIC-Me-co-ligand(s) core (wherein Me is a radioactive isotope of Tc or Re), which can be attached to a polypeptide site-specifically during peptide synthesis or conjugated to a recombinantly produced polypeptide using known conjugation chemistry for radiolabeling. Preferably, such chelators have a hydrophilic character.

In a related aspect of the present disclosure, there is provided a composition comprising a HER3 binding polypeptide, fusion protein or conjugate as defined herein and at least one pharmaceutically acceptable excipient or carrier. In one embodiment, said composition comprises at least one additional active agent, such as a therapeutic agent. A suitable therapeutic agent may be an agent that potentiates the activity of the HER3 binding polypeptide, fusion protein or conjugate or an agent that has a different mode of action, for example affecting a different aspect of a HER3-related condition, such as cancer. Non limiting examples of additional active agent are a therapeutic agents selected from the group consisting of immunostimulatory agents, radionuclides, toxic agents, enzymes, factors recruiting effector cells and photosensitizers.

It should be understood that the HER3 binding polypeptide according to the present disclosure may be useful as a therapeutic or diagnostic agent in its own right or as a means for targeting other therapeutic or diagnostic agents, with e.g. direct or indirect effects on HER3. A direct therapeutic effect may for example be accomplished by inhibiting HER3 signaling. For an indirect effect, one embodiment provides a combination of a HER3 binding polypeptide according to the invention with a therapeutic agent. Non-limiting examples of therapeutic agents that may prove useful in such a combination are immunostimulatory agents, radionuclides, toxic agents, enzymes, factors recruiting effector cells (e.g. T or NK cells) and photosensitizers. Thus, in one embodiment, the HER3 binding polypeptide as such, or as comprised in a HER3 binding combination (such as a fusion protein, conjugate or composition) according to the present disclosure is provided for use in therapy.

HER3 may also serve as a valuable marker to predict the prognosis of certain cancers, such as colon cancer, endometrial cancer, gastric cancer, glioma, breast cancer, pancreas cancer, head and neck squamous carcinoma, lung cancer, melanoma, medulloblastoma, neuroepithelioma, ovarian cancer, Paget's disease, papillary thyroid cancer, prostate cancer, skin squamous cell carcinoma, transitional cell carcinoma and vestibular schwannoma. For example, HER3 expression has been shown to have prognostic value since high levels of receptor expression are associated with significantly shorter survival time compared with patients that overexpress HER2.

Hence, in another aspect of the present disclosure, there is provided a HER3 binding polypeptide, fusion protein, conjugate or composition as described herein for use as a medicament, a diagnostic agent or a prognostic agent. In one embodiment, said polypeptide, fusion protein, conjugate or composition modulates HER3 function or signaling. Herein the term "modulate" refers to changing the activity of HER3, such as rendering HER3 hypomorph, partially inhibiting or fully inhibiting HER3 signaling or function. In one embodiment, said polypeptide, fusion protein, conjugate or composition inhibits HER3 signaling and hence has a therapeutic effect as a medicament. A diagnostic agent and/or prognostic agent may comprise polypeptide, fusion protein, conjugate or composition which modulates or inhibits HER3 signaling. However, said polypeptide, fusion protein, conjugate or composition which does not modulate or inhibit HER3 signaling may be equally useful as a prognostic or diagnostic agent.

In one embodiment, there is provided a HER3 binding polypeptide, fusion protein, conjugate or composition for use in the treatment, diagnosis or prognosis of a HER3 related condition, such as cancer. In one embodiment, said cancer is selected from the group consisting of cancer disease, such as colon cancer, endometrial cancer, gastric cancer, glioma, breast cancer, pancreas cancer, head and neck squamous carcinoma, lung cancer, melanoma, medulloblastoma, neuroepithelioma, ovarian cancer, Paget's disease, papillary thyroid cancer, prostate cancer, skin squamous cell carcinoma, transitional cell carcinoma and vestibular schwannoma. In one embodiment, said cancer is selected from breast cancer, ovarian cancer and prostate cancer. Other cancer diseases characterized by over-expression of HER3 may also be suitable for treatment with the disclosed HER3 binding polypeptide, fusion protein, conjugate or composition.

In another aspect, there is provided a method of detecting HER3, comprising providing a sample suspected to contain HER3, contacting said sample with a HER3 binding polypeptide, fusion protein, conjugate or a composition as described herein, and detecting the binding of the HER3 binding polypeptide, fusion protein, conjugate or composition to indicate the presence of HER3 in the sample. In one embodiment, said method further comprises an intermediate washing step for removing non-bound polypeptide, fusion protein, conjugate or composition, after contacting the sample.

In one embodiment, there is provided a method, such as a diagnostic or prognostic method, for determining the presence of HER3 in a subject, the method comprising the steps:

contacting the subject, or a sample isolated from the subject, with a HER3 binding polypeptide, fusion protein, conjugate or a composition as described herein, and obtaining a value corresponding to the amount of the HER3 binding polypeptide, fusion protein, conjugate or composition that has bound in said subject or to said sample.

In one embodiment, said method further comprises an intermediate washing step for removing non-bound polypeptide, fusion protein, conjugate or composition, after contacting the subject or sample and before obtaining a value.

In one embodiment, said method further comprises a step of comparing said value to a reference. Said reference may be scored by a numerical value, a threshold or a visual indicator, for example based on a color reaction. The skilled person will appreciate that different ways of comparison to a reference are known in the art may be suitable for use.

In one embodiment, said method is performed in vivo.

In one embodiment, said method is performed in vitro.

In one embodiment of such a method, said subject is a mammalian subject, such as a human subject.

In yet another related aspect there is provided a method for in vivo imaging of the body of a subject, such as a mammalian subject, such as a human subject, having or suspected of having a HER3 related condition characterized by over-expression of HER3, such as cancer, comprising the steps:

administering a radiolabeled polypeptide, fusion polypeptide or conjugate as described herein, wherein the radionuclide is suitable for imaging, into the body of the mammalian subject; and obtaining one or more images, within 1-72 hours of administration of the radiolabeled polypeptide, of at least a part of the subject's body using a medical imaging instrument, said image(s) indicating the presence of the radionuclide inside the body.

Said medical instrument may for example be a gamma camera, a PET scanner or a SPECT scanner. The skilled person will know what other medical imaging instruments may be suitable for use. The skilled person will also know that any cancer manifested by solid tumors and HER3 expression may be visualized in vivo by said method.

In a related aspect, there is provided a method of treatment of a HER3 related condition, comprising administering to a subject in need thereof an effective amount of a HER3 binding polypeptide, fusion protein, conjugate or composition as described herein. Consequently, in the method of treatment, the subject is treated with a HER3 binding polypeptide, fusion protein, conjugate or composition according to the invention. In a more specific embodiment of said method, the HER3 binding polypeptide, fusion protein, conjugate or composition as described herein modulates, such as inhibits, HER3 function or signaling. In a more specific embodiment of said method, the binding of the HER3 binding polypeptide, fusion protein, conjugate or composition to HER3 expressed on a cell surface in the subject inhibits HER3 signaling.

In one embodiment, said HER3 related condition is cancer, such as a cancer selected from the group consisting of cancer disease, such as colon cancer, endometrial cancer, gastric cancer, glioma, breast cancer, pancreas cancer, head and neck squamous carcinoma, lung cancer, melanoma, medulloblastoma, neuroepithelioma, ovarian cancer, Paget's disease, papillary thyroid cancer, prostate cancer, skin squamous cell carcinoma, transitional cell carcinoma and vestibular schwannoma. In one embodiment, said cancer is selected from the group consisting of breast cancer, ovarian cancer and prostate cancer. Any cancer manifested by solid tumors and HER3 expression.

In a further aspect, there is provided a polynucleotide encoding a HER3 binding polypeptide as described above, as well as an expression vector comprising such a polynucleotide. Such an expression vector may enable production of a HER3 binding polypeptide, for example by expression in a host cell.

While the invention has been described with reference to various exemplary embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated for carrying out this invention, but that the invention will include all embodiments falling within the scope of the appended claims.

BRIEF DESCRIPTION OF THE FIGURES

FIG. 1A-1D is a listing of the amino acid sequences of examples of HER3 binding motifs comprised in HER3 binding polypeptides of the invention (SEQ ID NO:1-35), examples of 49-mer HER3 binding polypeptides according to the invention (SEQ ID NO:36-70), examples of 58-mer HER3 binding polypeptides according to the invention (SEQ ID NO:71-105), previously published, HER3 specific Z variants Z05416 (SEQ ID NO:106) and Z05417 (SEQ ID NO:107), and the albumin binding polypeptide PP013 (SEQ ID NO:109).

FIG. 3 shows density plots from the fluorescent activated cell sorting, described in Example 2, of the affinity maturation library Sc:$Z_{HER3LIB2}$ displayed on S. carnosus. The HER3 binding signal (FL-2) is represented on the y-axis and the surface expression level (FL-6) is represented on the x-axis. The dot plots show cells from the original unsorted library as well as cells isolated in the $1^{st}$, $2^{nd}$, $3^{rd}$ and $4^{th}$ selection round, respectively. Only results from labeling strategy 2 (S2) are shown, but similar results were observed for labeling strategy 1 (S1). For comparison of HER3 binding signals, a dot plot is shown for the reference polypeptide Z05417.

FIG. 4A-4B shows the biosensor off-rate ranking of the ten affinity matured HER3 binding polypeptides Z08694-Z08703 as described in Example 3. (A) Sensorgrams of purified Z variants isolated from Sc:$Z_{HER3LIB2}$ injected over immobilized human HER3-Fc. The sensorgrams for Z08698 and Z08699 are highlighted (dark grey and as indicated). The sensorgrams for the other affinity matured variants (Z08694-Z08697 and Z08700-Z08703) are shown in black. For comparison, the reference polypeptide Z05417 was included in the analysis (light grey). (B) Off-rate ranking ($k_d = k_{off}$) was performed by estimating the fold-change of $k_{off}$ values for each Z variant molecule compared to the off-rate of Z05417.

Figure 2:
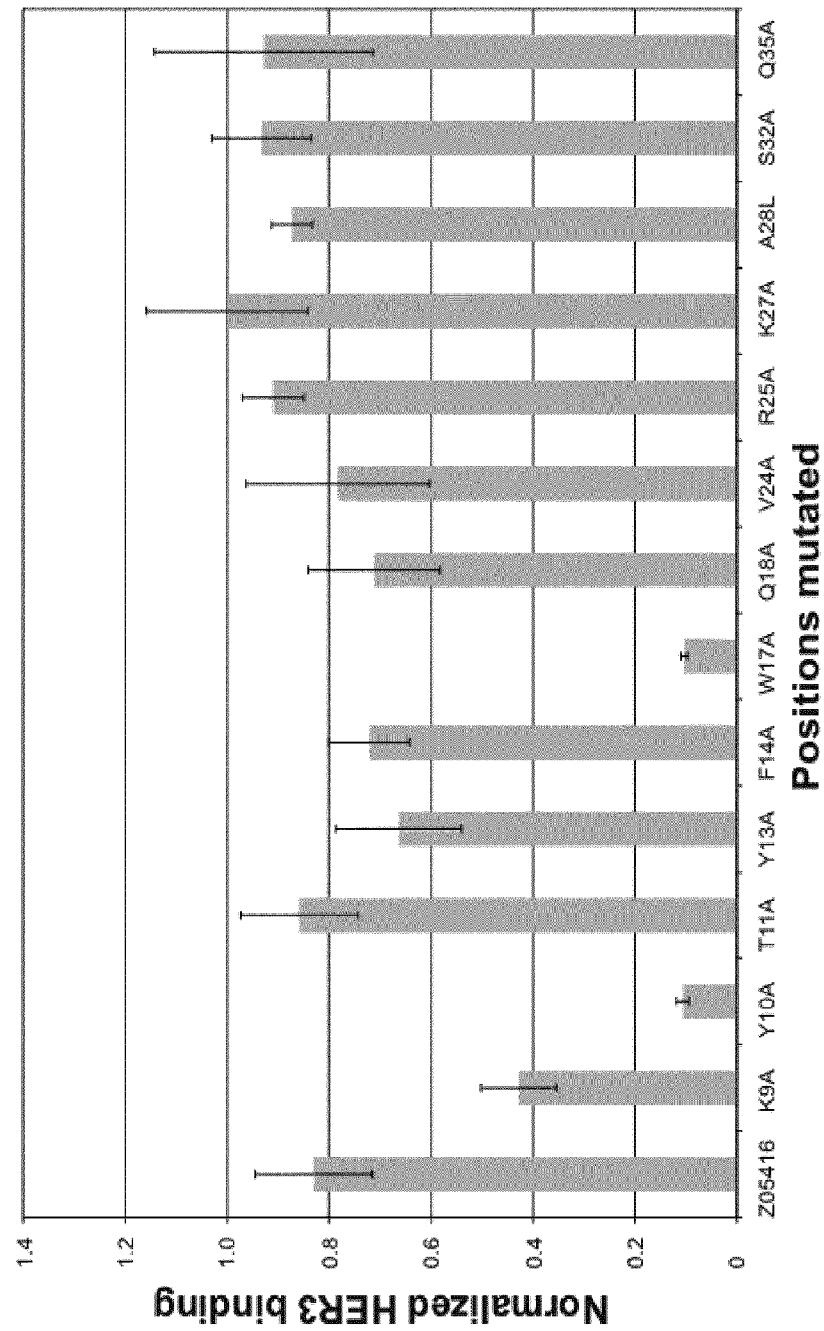
FIG. 2 shows the result from the flow cytometric analysis of the alanine scanning experiment described in Example 1. The 13 residues in the HER3 binding polypeptide that were substituted one by one with alanine are represented on the x axis, and a ratio of FL-2 fluorescence intensity, corresponding to HER3 binding, and FL-6 fluorescence intensity, corresponding to surface expression level (monitored by HSA binding), is represented on the y-axis.

The invention will now be illustrated further through the non-limiting description of experiments conducted in accordance therewith. Unless otherwise specified, conventional chemistry and molecular biology methods were used throughout.

EXAMPLES

Example 1

Rational Design of a New Generation of HER3 Binding Z Variants

In this Example, an affinity maturation library was constructed based on HER3 binding polypeptides Z05416 (SEQ ID NO:106) and Z05417 (SEQ ID NO:107), selected from a previous affinity maturation library (Kronqvist et al, 2010, supra), as well as on results from an alanine scanning analysis of Z05416 assessed by Fluorescence-Activated Cell Sorting (FACS) as described in this Example.

Materials and Methods

Labeling of HER3 and HSA:

Biotinylation of recombinant human HER3/Fc chimera (R&D Systems, cat. no. 348-RB-050), here denoted HER3-Fc, was performed using the Biotin-XX Microscale Protein Labeling Kit (Invitrogen, cat. no. B30010) according to the supplier's recommendations. The concentration of labeled protein was determined using amino acid analysis. The extracellular domain of HER3 (Sino Biological Inc., cat. no. 10201-H08H), here denoted HER3-ECD, was conjugated with biotin carboxylic acid, succinimidyl ester in NaHCO$_3$ (0.1 M, pH 8.5) for 1.5 h. Subsequently, glycine was added to stop the reaction followed by buffer exchange to PBS (10 mM phosphate, 137 mM NaCl, 2.68 mM KCl, pH 7.4) using a PD MiniTrap G-25 column (GE Healthcare, cat. no. 28-9180-07) according to manufacturer's recommendations. Human serum albumin (HSA; Sigma, cat. no. A-3782) was fluorescently labeled using ALEXA FLUOR 647 (Fluorescent Dye)succinimidyl ester (Invitrogen, cat. no. A20006) according to the supplier's recommendations. The protein buffer was changed to PBS (10 mM phosphate, 137 mM NaCl, 2.68 mM KCl, pH 7.4) or PBS supplemented with 0.1% PLURONIC F108 NF Surfactant (PBSP; BASF Corporation, cat. no. 30085231) in order to remove any excess fluorophore.

Alanine Scanning Mutagenesis:

The Z variant Z05416, selected previously as described in Kronqvist et al (2010, supra), was used as a template for construction of 12 mutants in which residues at positions 9, 10, 11, 13, 14, 17, 18, 24, 25, 27, 32 and 35 were replaced with an alanine, one for each of the mutants. Conventional site-directed mutagenesis was performed using a vector (pSCZ05416 (Kronqvist et al, 2010 supra)) encoding Z05416, and oligonucleotides encoding the respective alanine replacements (using the codon GCG). In an additional mutant, the original alanine residue at position 28 within Z05416 was substituted to a valine (using the codon GTG) by the same means. Gene sequences were digested with NheI and XhoI restriction enzymes (New England Biolabs) and ligated to the staphylococcal display vector pSCZ1 (Kronqvist et al, Protein Engineering Design & Selection 21: 247-255 (2008)) that had been digested with the same enzymes, using T4 DNA ligase (New England Biolabs) according to supplier's recommendations. The *E. coli* strain RR1ΔM15 (Rüther, Nucleic Acids Res 10:5765-5772 (1982)) was used as host for plasmid construction and preparation was performed with a JETSTAR Kit (Genomed, cat. no. 220 020) according to the supplier's recommendations. BigDye Thermo Cycle Sequencing reactions and an ABI Prism 3700 instrument (Applied Biosystems, Foster City, Calif.) were used to verify the presence of the alanine or valine mutation in each plasmid. The constructs were transformed to electrocompetent *S. carnosus* TM300, as described in Lofblom et al (J Appl Microbiol 102: 736-747 (2007)).

FACS Analysis of Alanine and Valine Mutants:

Staphylococcal cells displaying the alanine and valine mutants were inoculated into 10 ml tryptic soy broth supplemented with yeast extract (TSB-YE; Merck, Darmstadt, Germany) and with 20 μg/ml chloramphenicol, and grown overnight at 37° C. at 150 rpm agitation. 10$^6$ cells from overnight cultures were washed with 800 μl PBS supplemented with 0.1% PLURONIC F108 NF Surfactant (PBSP; pH 7.4; BASF Corporation, cat. no. 30085231). The cells were pelleted by centrifugation (3500×g, 4° C., 6 min) and resuspended in 50 μl of PBSP containing biotinylated 5 nM HER3-Fc. Equilibrium binding was reached by incubation at room temperature for 2 h with gentle mixing. The cells were washed with 180 μl ice-cold PBSP, followed by incubation for 40 min in the dark in 200 μl ice-cold PBSP containing 150 nM Alexa Fluor® 647-conjugated HSA and Streptavidin-Alexa 488 conjugate. Following one wash with 180 μl ice-cold PBSP, cells were resuspended in 200 μl ice-cold PBSP prior to flow cytometric analysis. The mean fluorescence intensity (MFI) was measured using a FACS Vantage SE (BD Biosciences, San Jose, Calif.) flow cytometer. The experiment was carried out in duplicates on different days using freshly prepared solutions.

Library Design:

A new library was designed, in which 13 positions in the Z molecule were biased towards the amino acid residues based on the sequences of the HER3 binding Z variants Z05416 and Z05417 (Kronqvist et al, 2010 supra). Each position was randomized with 17 codons corresponding to amino acids: A, E, F, G, H, I, K, L, M, N, Q, R, S, T, Y, V, W (excluding C, D, P in all positions) with the amino acid residues based on the sequences of the HER3 binding Z variants Z05416 and Z05417 spiked in at a higher proportion to generate an average mutation frequency of approximately three mutations per molecule (Table 1). The randomization frequency in each position was also normalized with the results from the alanine scanning experiment described above, resulting in less mutations in important positions and vice versa (Table 1).

A SLONOMAX library of double-stranded DNA encoding partially randomized positions in helix 1 and 2 of the HER3 binding polypeptide, flanked with the restriction sites XhoI and SacI (5'-CTC GAG GCG GAA GCC AAA TAC GCC AAA GAA NNN NNN NNN GCG NNN NNN GAG ATC NNN NNN TTA CCT AAC TTA ACC NNN NNN CAA NNN NNN GCC TTC ATC NNN AAA TTA NNN GAT GAC CCA AGC CAG AGC TCT C' (SEQ ID NO:108; randomized codons illustrated as NNN) was ordered from Sloning Biotechnology GmbH (Pucheim, Germany). The theoretical distributions of amino acid residues in the new library for the 13 variable Z positions are given in Table 1.

and ethanol precipitation for purification and concentration of DNA fragments. Next, the library-encoding plasmids were transformed into electrocompetent E. coli SS320 (Lucigen, cat. no. 60512-1) by electroporation and individual clones were sequenced for library validation by BigDye Thermo Cycle Sequencing using an ABI Prism 3700 instrument (Applied Biosystems, Foster City, Calif.). The library plasmids were subsequently isolated using a JETSTAR Maxi Kit (Genomed cat. no. 220020), purified by phenol-chloroform extraction and concentrated by isopropanol precipitation. Finally, the library (hereafter denoted Sc:$Z_{HER3LIB2}$) was transformed by electroporation into electrocompetent S. carnosus as previously described (Lofblom et al, 2007, supra).

Library quality analysis: An aliquot of Sc:$Z_{HER3LIB2}$ (at least ten times the library size, i.e. more than $6.7 \times 10^8$) was inoculated to 100 ml TSB-YE with 20 µg/ml chloramphenicol and grown overnight at 37° C. and 150 rpm. After 16 h, $10^7$ cells were washed once with 1 ml PBSP. The cells were pelleted by centrifugation (3500×g, 4° C., 6 min) and resuspended in PBSP containing 225 nM ALEXA FLUOR 647-conjugated HSA and incubated for 1 h at RT in the dark. Following one wash with 1 ml ice-cold PBSP, cells were resuspended in 300 µl ice-cold PBSP prior to flow cytometric analysis. The mean fluorescence intensity (MFI) was measured using a MoFlo Astrios Cell Sorter (Beckman Coulter) flow cytometer.

Results

FACS Analysis of Alanine and Valine Mutants of a HER3 Binding Polypeptide:

TABLE 1

Library design

| Amino acid position in the Z variant molecule | Randomization (amino acid abbreviations) | No of amino acids | Proportion | Randomization (amino acid abbreviations) | No of amino acids | Proportion |
|---|---|---|---|---|---|---|
| 9 | A, E, F, G, H, I, L, M, N, Q, S, T, V, W, Y | 15 | 0.8 | K, R | 2 | 44.00 |
| 10 | A, E, F, G, H, I, K, L, M, N, Q, R, S, T, V, W | 16 | 0.2 | Y | 1 | 96.00 |
| 11 | A, E, F, G, , H, I, K, L, M, N, Q, R, V, W, Y | 15 | 1.9 | T, S | 2 | 35.75 |
| 13 | A, E, F, G, H, I, K, L, M, N, Q, R, S, T, V, W | 16 | 1.8 | Y | 1 | 96.80 |
| 14 | A, E, G, H, I, K, L, M, N, Q, R, S, T, V, W | 15 | 1.9 | F, Y | 2 | 71.20 |
| 17 | A, E, F, G, H, I, K, L, M, N, Q, R, S, T, V, Y | 16 | 0.2 | W | 1 | 71.20 |
| 18 | A, E, F, G, H, I, K, L, M, N, R, S, T, V, W, Y | 16 | 1.8 | Q | 1 | 71.20 |
| 24 | A, E, F, G, H, I, K, L, M, N, Q, R, S, T, W, Y | 16 | 1.8 | V | 1 | 71.20 |
| 25 | A, E, F, G, H, I, K, L, M, N, Q, S, T, V, W, Y | 16 | 1.8 | R | 1 | 71.20 |
| 27 | A, E, F, G, H, I, L, M, N, Q, R, S, T, V, W, Y | 16 | 1.8 | K | 1 | 71.20 |
| 28 | E, F, G, H, I, K, L, M, N, Q, R, S, T, V, W, Y | 16 | 1.8 | A | 1 | 71.20 |
| 32 | A, E, F, H, I, K, L, M, N, Q, R, T, V, W, Y | 15 | 1.9 | S, G | 2 | 35.75 |
| 35 | A, E, F, G, H, I, K, L, M, N, R, S, T, V, W, Y | 16 | 1.8 | Q | 1 | 71.20 |

Library Construction and Cloning:

The library was amplified using Phusion DNA polymerase (Finnzymes, cat. no. F530L) during 11 cycles of PCR. The PCR product was purified using QIAquick PCR Purification Kit (Qiagen, cat. no. 28106) according to the supplier's recommendations. Subsequently, the library oligonucleotides were digested by XhoI and SacI-HF (New England Biolabs) restriction enzymes and purified by preparative gel electrophoresis (2% agarose gel) using QIAquick gel extraction kit (Qiagen, cat.no. 28704). A modified version of the S. carnosus expression vector pSCZ1 (Kronqvist et al, 2008 supra) was restricted by XhoI and SacI-HF enzymes and purified by preparative gel electrophoresis as described above. The library oligonucleotides were ligated into the vector using T4 DNA ligase at a 1:5 molar ratio of vector to insert, followed by phenol-chloroform extraction Alanine scanning mutagenesis was used to study the high-affinity binding site of known HER3 binder Z05416 to the extracellular domain of human HER3-Fc. The thirteen originally randomized residues in the Z scaffold were each substituted to an alanine or valine amino acid, and each construct was subcloned into the staphylococcal display vector for subsequent transformation to the staphylococcal host. Staphylococcal cells displaying the thirteen replacements were incubated with biotinylated HER3-Fc. Next, cells were washed and incubated with Streptavidin-Alexa 488 conjugate and HSA for binding to the albumin binding protein (ABP) in fusion with the Z variant molecules to monitor the surface expression level and normalization of the antigen-binding signal. After washing, the effect of each alanine or valine replacement on HER3 binding was analyzed using flow cytometry. The results showed that alanine substitutions at positions 9, 10, and 17 drastically reduced the affinity for HER3-Fc, indicating that these positions are involved in target binding (FIG. 2). Furthermore, the alanine replacement at residue 27 showed a slightly increased affinity for the target, indicating that the original residue does not affect target binding to a larger extent.

Library Construction and Cloning:

The new library was designed based on the previously selected HER3 binding polypeptides Z05416 and Z05417 as well as the result from the alanine scan. The theoretical size of the designed library was $5.6 \times 10^6$ clones, including Z variants with up to 3 mutations. The library of DNA fragments was cloned into the staphylococcal expression vector. Sequence analysis of individual library members verified a distribution of codons in accordance with the theoretical design and a low proportion of frame shifts (1.8%). The mutation frequency was somewhat lower than the intended 3 out of 13 amino acids; on average 2 mutations per clone were found. The library was transformed into *S. carnosus* generating a diversity of approximately $6.7 \times 10^7$ individual clones.

Library Quality Analysis:

In order to verify that the Z variants of the maturation library Sc:$Z_{HER3LIB2}$ were functionally displayed on the bacterial surface, staphylococcal cells from the library were incubated with fluorescently labeled HSA and analyzed using flow cytometry. The result showed that around 80% of the library expressed full-length proteins with functional ABP fusions on the cell surface. A new maturated library of HER3 binding polypeptides had thus been successfully constructed.

Example 2

Selection, Screening and Characterization of HER3 Binding Z Variants

Materials and Methods

Cell Labeling and Staphylococcal Cell Sorting Using FACS:

An aliquot of the library Sc:$Z_{HER3LIB2}$ designed in Example 1 (at least ten times the library size, i.e. more than $6.7 \times 10^8$ variants) was inoculated into TSB-YE with 10 µg/ml chloramphenicol and grown overnight at 37° C. and 150 rpm. The following day, cells were harvested by centrifugation (6000 rpm, 6 min, 4° C.) and washed in PBSP before addition of HER3-ECD, biotinylated as described in Example 1. Cells were incubated at room temperature with gentle mixing until equilibrium binding was reached. Washing with ice-cold PBSP was performed prior to incubation with 5 µg/ml streptavidin conjugated with phycoerythrin (SAPE; Invitrogen, cat. no. S21388) and 300 nM ALEXA FLUOR 647-conjugated HSA for 30 min on ice in the dark. Cells were once again washed and finally resuspended in ice-cold PBSP. The library was labeled and sorted in altogether four rounds using a MOFLO Astrios (Beckman Coulter) flow cytometer. For sort 1 and 2, the library was labeled with 5 nM of biotinylated HER3-ECD while sort 3 was performed using two different labeling strategies with either 1 nM (strategy 1) or 5 nM (strategy 2) of biotinylated HER3-ECD. In strategy 2, the library was additionally subjected to an off-rate selection by subsequently incubating cells with 5 nM of non-biotinylated HER3-ECD for 1 h at room temperature prior to labeling with SAPE and HSA ALEXA FLUOR 647. Prior to sort 4, both strategies from sort 3 were subjected to an off-rate selection by first incubating the cells with 1 nM of biotinylated HER3-ECD; cells were then washed before addition of 1 nM of non-biotinylated HER3-ECD for 4 h at room temperature. For each round of sorting, a number of cells corresponding to approximately ten times the library size was analyzed in the flow cytometer and the top fraction of cells (approximately 0.1-0.5%), with the highest ratio of HER3 binding to cell surface expression, was gated out and sorted into an eppendorf tube with TSB-YE. Subsequently, sorted cells were inoculated into TSB-YE supplemented with chloramphenicol (1 µg/ml) for overnight amplification prior to the next sorting round. Finally, isolated cells after the $3^{rd}$ and $4^{th}$ sorting rounds were spread on agar plates containing chloramphenicol.

Sequencing:

Sequencing of individual staphylococcal clones was performed after sorting rounds 3 and 4: 96 individual colonies from each selection strategy were picked for BigDye Thermo Cycle Sequencing reactions using an ABI Prism 3700 instrument (Applied Biosystems, Foster City, Calif.).

On-Cell Affinity Ranking:

40 individual Sc:$Z_{HER3LIB2}$ clones, selected based on the sequencing result, were inoculated into TSB-YE with chloramphenicol (10 µg/ml) and grown overnight at 37° C. and 150 rpm. Cells were then pelleted by centrifugation and washed in PBSP before resuspension in either 0.5 nM or 2 nM of biotinylated HER3-ECD. After 1 h incubation at room temperature with gentle mixing, cells were washed with ice-cold PBSP and labeled with SAPE at a final concentration of 5 µg/ml and ALEXA FLUOR 647-conjugated HSA at a concentration of 300 nM for 30 min on ice. Finally, cells were washed and resuspended in ice-cold PBSP. All samples were ranked based on the ratio between mean fluorescence intensities (MFI) from HER3 binding and cell surface expression signals in a Gallios (Beckman Coulter) flow cytometer. In addition, the precursor Z variant Z05417 was analyzed for comparison.

Results

Flow Cytometric Sorting for Isolation of Improved Z Variants:

For isolation of matured HER3 binding Z variants, the staphylococcal library was subjected to four rounds of FACS. The selection stringency was modified throughout the selection process by changing the sorting parameters and gates, and also by decreasing the target concentration as well as incorporating off-rate selections at later sorting rounds. Prior to the $3^{rd}$ round of sorting, the selection scheme was divided into two different tracks using different labeling strategies (referred to as strategy 1 and strategy 2) as described in the Materials and methods section.

The visualization of the target-binding properties of the library in the flow cytometer revealed an enrichment of HER3-positive clones in each sorting round (FIG. 3). In addition, enrichment of binders with improved HER3 binding signals compared to the precursor Z variant Z05417, included as a reference, could be observed throughout the sorting. Both strategy 1 and 2 gave similar results. After the $3^{rd}$ and $4^{th}$ rounds of FACS, isolated cells were spread on semi-solid medium for sequencing and characterization of individual candidates.

Sequencing:

After the $3^{rd}$ sorting round, 70 unique sequences out of 130 total reads were identified, while 37 unique sequences out of 142 reads where identified after the $4^{th}$ and final round. These results indicated an enrichment of individual HER3 binding clones between sorting rounds 3 and 4.

On-Cell Affinity Ranking:

40 unique clones from either the $3^{rd}$ or the $4^{th}$ sorting round were affinity ranked by flow cytometry, by determining the ratio between the HER3 binding signal and the surface expression level. The vast majority of analyzed clones showed improved affinity towards HER3 compared to the precursor HER3 binding polypeptide Z05417. The amino acid sequences of the 58-mer Z variants of these binders with improved affinity are listed in FIG. 1A-1D and in the sequence listing as SEQ ID NO:71-105. The deduced HER3 binding motifs of these Z variants are listed in FIG. 1 and in the sequence listing as SEQ ID NO:1-35. The amino acid sequences of the 49-mer polypeptides predicted to constitute the complete three-helix bundle within each of these Z variants are listed in FIG. 1A-1D and in the sequence listing as SEQ ID NO:36-70.

Example 3

Production and Characterization of a Selection of HER3 Binding Z Variants

In this Example, the top ten candidates (Z08694-Z08703; SEQ ID NO:71-80; see FIG. 1A-1D) from the on cell-affinity ranking described in Example 2 were recloned and purified from *E. coli* cell extracts as C-terminally $His_6$-tagged Z variants, and characterized further in terms of stability and binding affinity for HER3.

Materials and Methods

Cloning, Protein Expression and Purification of Z Variants:

DNA sequences encoding ten HER3 binding polypeptides selected in Example 2 (Z08694-Z08703; SEQ ID NO:71-80) were amplified from colonies by PCR, using primers introducing NdeI and XhoI restriction sites. The Z variants were subsequently cloned into the NdeI and XhoI restricted expression vector pET26b+ (Novagen), for encoding of monomeric Z variants with a C-terminal $His_6$-tag in the format Z#####-LEHHHHHH (SEQ ID NO: 122). The plasmids were transformed into Rosetta(DE3) *E. coli* cells by heat shock. Cells were cultured in TSB-YE at 37° C. and protein expression was induced by the addition of IPTG (isopropyl-β-D-1-thiogalactopyranoside) to a final concentration of 1 mM when the $OD_{600}$ had reached approximately 1. After incubation overnight at 25° C., the cells were harvested by centrifugation at 4000 rpm for 8 min at 4° C. The cell pellets were resuspended in lysis buffer (7 M guanidinium chloride, 47 mM $Na_2HPO_4$, 2.65 mM $NaH_2PO_4$, 10 mM Tris-HCl, 100 mM NaCl) and incubated for 2 h at 37° C. and 150 rpm. Subsequently, cell debris was removed by centrifugation at 16000 rpm for 20 min at 4° C. The supernatants were isolated and the Z variants were purified by IMAC using a HisPurTM Cobalt resin (Thermo Scientific, cat. no 89965) under denaturing conditions. Buffer was exchanged to PBS by dialysis using Slide-A-Lyzer dialysis cassettes, 3.5 kDa cutoff (Thermo Scientific). The molecular weight and the purity of the purified Z variants were verified by LC/MS (Agilent Technologies 6520 ESI-Q-TOF) and SDS-PAGE. The protein concentration was determined by absorbance measurement at 280 nm.

Off-Rate Ranking by Biosensor Analysis:

All biosensor assays were performed on a ProteOn XPR36 instrument (Bio Rad Laboratories, CA, USA) using PBS+0.05% Tween (PBST) as running buffer and 15 mM NaOH for regeneration. In all experiments, subtraction of responses from each sample over a blank surface was performed to minimize buffer contributions. Recombinant human and murine HER3-Fc (R&D systems, cat. no. 348-RB-050 and 4518-RB-050, respectively) was immobilized on separate GLC chips (Bio Rad Laboratories, CA, USA) using standard sulfo-NHS/EDAC amine coupling chemistry. The ligands were diluted to a final concentration of 10 μg/ml in 10 mM NaAc, pH 4.5, and final immobilization levels were approximately 3000 RU. The purified polypeptides were subjected to off-rate ranking by injection of 25 nM of each Z variant over the immobilized ligands at a flow rate of 100 μl/min; association and dissociation time was set to 120 and 1800 seconds, respectively. Each Z variant was analyzed in duplicate and the fold-change of the off-rates of each HER3-specific Z variant compared to the $k_{off}$-value reported previously for the Z variant Z05417 (Kronqvist et al, 2010 supra) was determined by fitting a curve to the dissociation phase.

Biosensor Analysis of HER3 Binding Before and after Heat Treatment:

Z variants Z08698 and Z08699 at concentrations of 25 and 50 nM were subjected to heat treatment at 90° C. for 15 min. Binding to HER3 was evaluated by injection of 400 μl of each sample, before and after heat treatment, over immobilized human and mouse HER3, respectively, at a flow rate of 100 μl/min.

Circular Dichroism Spectroscopy:

Z variants Z08698 and Z08699 were diluted to 0.2 mg/ml in PBS and subjected to circular dichroism analysis. For each Z variant, a CD spectrum at 250-195 nm was recorded at 20° C. using a Jasco J-810 spectropolarimeter (Jasco Scandinavia AB) and a cell with an optical path-length of 1 mm. In addition, a variable temperature measurement (VTM) was performed to determine the melting temperature (Tm). In the VTM, the absorbance was measured at 220 nm while the temperature was raised from 20 to 90° C., with a temperature slope of 5° C./min.

Affinity Determination by Biosensor Analysis:

The equilibrium dissociation constant ($K_D$) was determined for the Z variants Z08698 and Z08699. A GLC sensor chip (Bio Rad Laboratories, CA, USA) was immobilized with human HER3-Fc as described above, with a final immobilization level of approximately 650 RU. Duplicate injections of a two-fold dilution series of each Z variant, ranging from 7.2 to 1.8 nM for Z08698 and from 6.8 to 1.7 nM for Z08699 (protein concentrations determined by amino acid analysis), were injected over immobilized human HER3. The flow rate was set to 50 μl/min and the association and dissociation was followed for 300 s and 4 h respectively. The on-rate ($k_{on}$) and off-rate ($k_{off}$) as well as the $K_D$ value were determined by fitting the sensorgrams to a Langmuir one-site binding model.

Results

Protein Expression and Purification:

The ten monomeric Z variant molecules (Z08694-Z08703) in Z#####-$His_6$ format yielded good production levels of soluble product and the purity of produced batches was estimated to exceed 95% by SDS-PAGE analysis. The LC/MS analysis verified the correct molecular weight for all pure Z variant molecules.

Figure 4A:
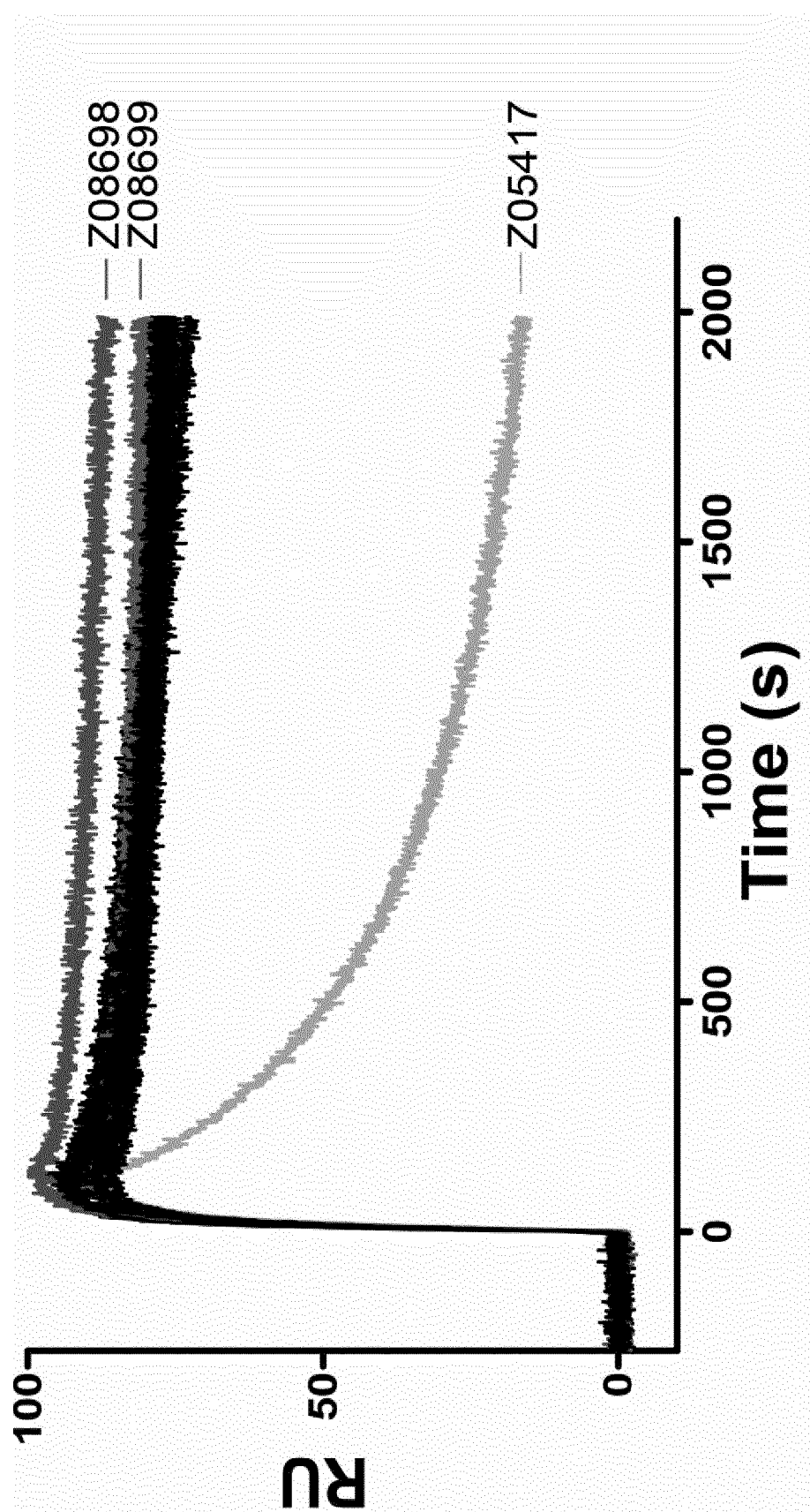

Off-Rate Ranking by Biosensor Analysis:

The ten Z variants expressed as described above were injected over a sensor chip surface immobilized with human HER3-Fc, and dissociation was followed during 30 min. All Z variant molecules generated similar binding curves to HER3 with greatly reduced off-rates compared to the precursor variant Z05417 (FIG. 4A). Due to the very slow off-rates of the isolated Z variant molecules, absolute dissociation constants were not determined at this stage.

Instead, the fold-change of dissociation constants compared to the previously reported $k_{off}$-value of Z05417 (Kronqvist et al, 2010 supra) were determined in order to rank the binders in terms of affinity (FIG. 4B). All purified affinity matured Z variants had off-rates reduced by at least 8-fold compared to Z05417. The two best binders, Z08698 and Z08699, showed the lowest $k_{off}$-values corresponding to approximately 21 times slower dissociation rates than that of Z05417.

Figure 5A:
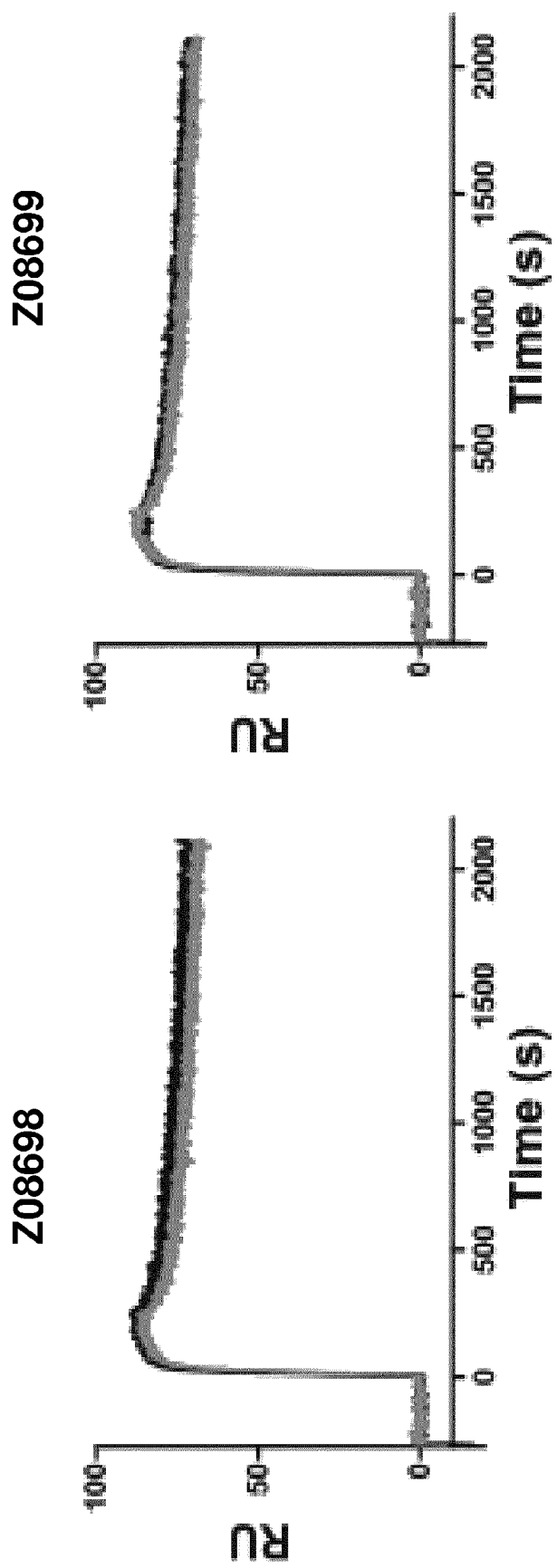
FIG. 5A, 5B, 5C shows the heat stability of affinity matured HER3 binding polypeptides evaluated by SPR and CD as described in Example 3. (A) Injections of 50 nM Z08698 and Z08699 as indicated before (black) and after (grey) heat treatment at 90° C., over immobilized human HER3-Fc in a ProteOn XPR36 instrument. (B) Variable temperature measurement (VTM) spectra obtained at 221 nm while heating the HER3-specific Z variants Z08698 and Z08699 from 20 to 90° C. (C) CD spectra of Z08698 and Z08699 as indicated, at wavelengths ranging from 250 to 195 nm at 20° C. before (black) and after (grey) the VTM. As seen in the figure, the spectra recorded before and after VTM completely overlap.

Biosensor Analysis of HER3 Binding Before and after Heat Treatment:

The interaction between HER3 and the Z variants Z08698 and Z08699 before and after heat treatment at 90° C. was evaluated by surface plasmon resonance (SPR) technology. The Z variant molecules were injected, before and after heating, over immobilized human and mouse HER3-Fc, and the obtained binding curves were compared. As shown in FIG. 5A, the sensorgrams for binding of Z08698 and Z08699 to human HER3-Fc overlap before and after heat treatment, demonstrating that the binding capacity of the Z variant molecules is unaffected by the elevated temperature treatment. The same was observed for both Z variant concentrations (25 nM and 50 nM) that were analyzed, as well as for binding of the murine HER3 receptor before and after heating. These results indicate for example that the Z variants are suitable for labeling with drug-conjugates such as radionuclides, because such labeling procedures often require heating of the protein to high temperatures.

Figure 5B:
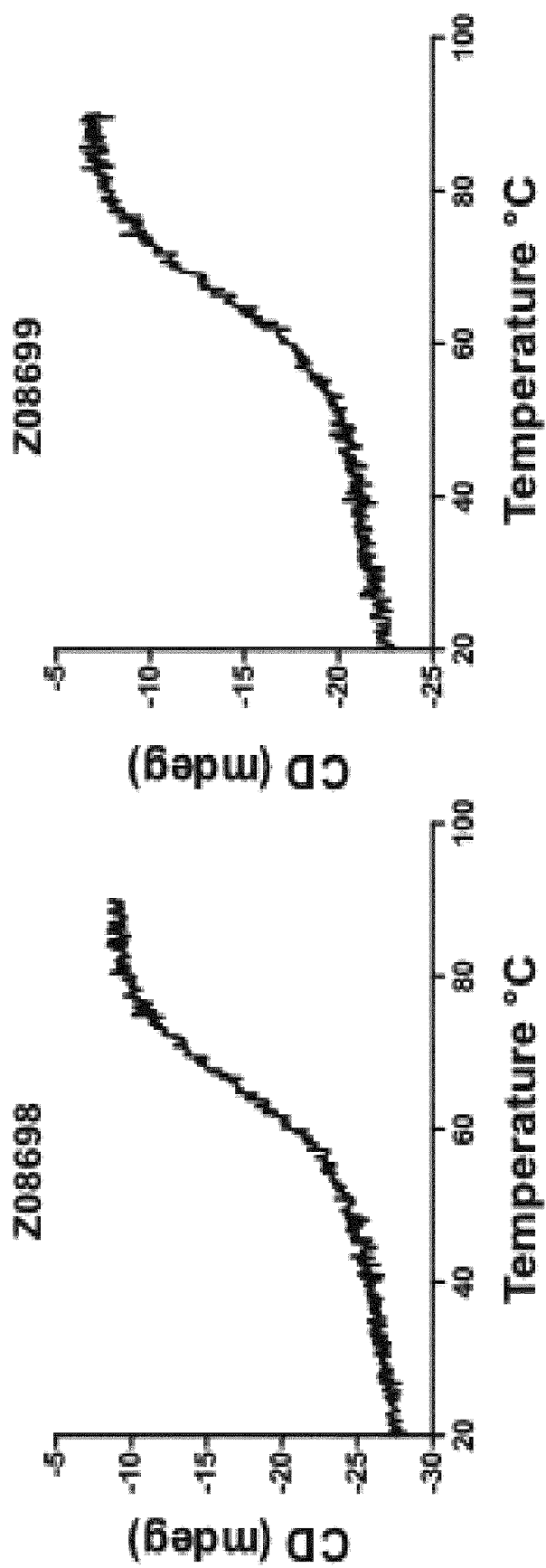
Figure 5C:
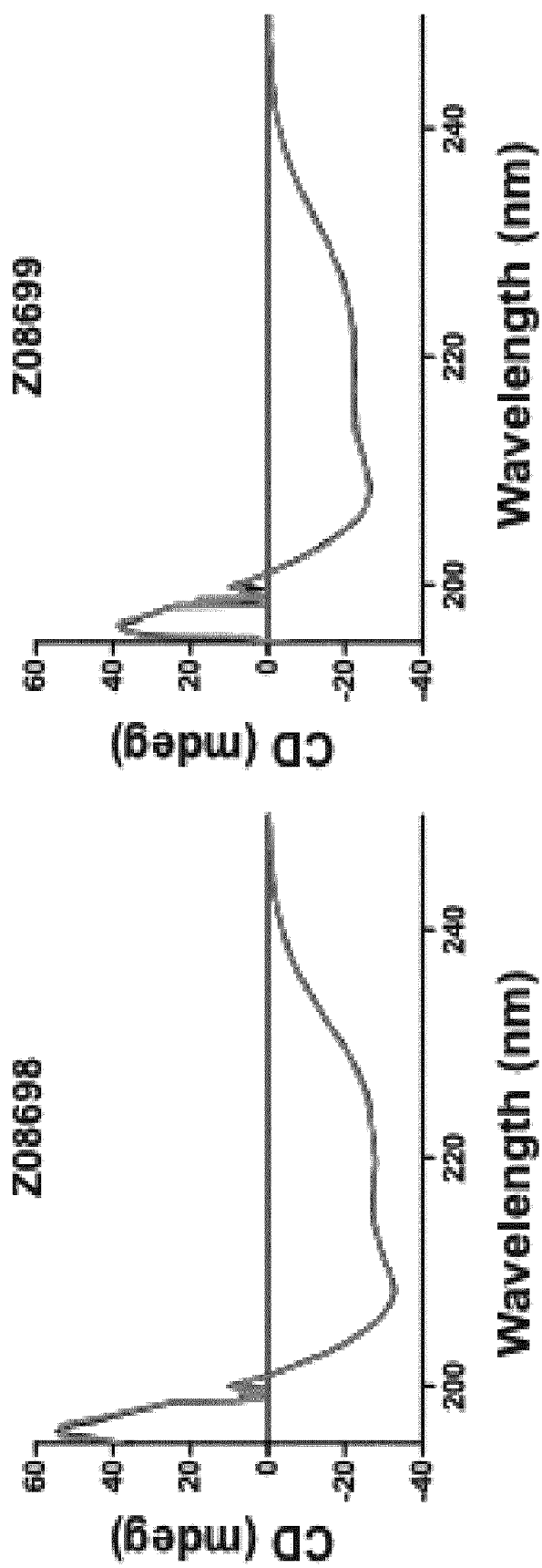

Circular Dichroism Spectroscopy:

From the VTM, the Tm for Z08698 and Z08699 were determined to be 64° C. and 65° C., respectively (FIG. 5B). Thus, these Z variant molecules demonstrate improved thermal stabilities compared to their precursors Z05416 and Z05417, which had Tm values of 61° C. and 57° C., respectively. In addition, the spectra at wavelengths ranging from 250-195 nm, obtained before and after the variable temperature measurement, show that both Z08698 and Z08699 maintain their alpha-helical structure and completely refold after heating to 90° C., as seen by the overlap between spectra generated before and after heating (FIG. 5C).

Affinity Determination by Biosensor Analysis:

The dissociation constants, $K_D$, of the Z variants Z08698 and Z08699 were determined using biosensor technology. A dilution series of each binder was injected over immobilized human HER3-Fc and $K_D$-values were determined by non-linear regression to a one-site binding model. The obtained affinities were estimated to 50 pM for Z08698 and 21 pM for Z08699 (Table 2), representing an affinity improvement of approximately 30 times when comparing the strongest binder Z08699 to the reference polypeptide Z05417. The reduced $K_D$-values of the affinity matured Z variants are due to the significantly slower dissociation rates compared to Z05417, which in turn are ascribed to a successful incorporation of off-rate selections in the sorting procedure described in Example 2.

TABLE 2

Affinities of two Z variants for human HER3 as determined by SPR

| Z variant | $K_D$ (pM, mean ± SD)[a] | $k_{on}$ ($M^{-1}s^{-1}$, mean)[a] | $k_{off}$ ($s^{-1}$, mean)[a] |
|---|---|---|---|
| Z08698 | 50 ± 5.0 | 8.3 × 10$^5$ | 4.1 × 10$^{-5}$ |
| Z08699 | 21 ± 2.4 | 1.9 × 10$^6$ | 3.9 × 10$^{-5}$ |

[a]Performed with duplicates of each concentration on the same day

Example 4

In Vitro Cell Assay Assessing the HER3 Specific Binding of Z Variants

In this Example, the Z variants Z08698 and Z08699 with a C-terminal His$_6$-tag were radiolabeled with $^{99m}$Tc and their in vitro cell binding properties to a range of different cancer cell lines were analyzed.

Materials and Methods

Labeling of Z Variants:

The Z variants Z08698 and Z08699 with a C-terminal His$_6$-tag, produced as described in Example 3, were labeled with $^{99m}$Tc at the His$_6$-tag using an IsoLink kit (Covidien) as described previously for other Z variants (Orlova et al, Journal of Nuclear Medicine 47: 512-519 (2006)). In brief, 500 µl (200-320 MBq) of $^{99m}$Tc-pertechnetate solution eluted, with sterile 0.9% NaCl, from an Ultra-TechneKow generator (Covidien) was added to the IsoLink carbonyl labeling agent of the IsoLink kit. The mixture was incubated at 100° C. for 20 min. 40 µl of the mixture was transferred to solutions containing respective Z variant (50 µg, appr. 6.8 nmol, in 40 µl PBS) and incubated at 50° C. The labeling yield after incubation for 60 min was analyzed by instant thin-layer chromatography (ITLC; using Tec-Control Chromatography strips, DARK GREEN from Biodex Medical Systems, cat. no. 150-771) and elution with PBS. The distribution of radioactivity along the thin layer chromatography strips was measured on a CYCLONE Storage Phosphor System and analyzed using the OPTIQUANT image analysis software (PerkinElmer). The labeled Z molecules were purified using NAP-5 desalting columns (GE Healthcare), pre-equilibrated and eluted with PBS. The purity of each preparation was assessed using ITLC cross-validated by SDS-PAGE.

Binding Specificity of Labeled Z Variants to HER3 Expressing Cells:

The specificity of $^{99m}$Tc(CO)$_3$-Z08698-His$_6$ and $^{99m}$Tc(CO)$_3$-Z08699-His$_6$ for binding to HER3-expressing cells was evaluated using LS174T colorectal carcinoma, NCI-N87 gastric carcinoma, MCG7 breast carcinoma, LNCaP and DU-145 prostate cancer cell lines (American Type Tissue Culture Collection, ATCC, via LGC Promochem, Boras, Sweden) The in vitro specificity test was performed according to methods described previously (Orlova et al, (2006), supra). Briefly, a solution of radiolabeled Z variant molecules (at 1 nM) was added to 6 Petri dishes (each containing approximately 2×10$^6$ cells). For blocking, 0.7 µM of non-labeled Z variant molecule was added 15 min before the radiolabeled conjugate to saturate the receptors. The cells were incubated for 1 h in a humidified incubator at 37° C. Thereafter, the media was collected and the cells were detached using trypsin-EDTA solution (0.25% trypsin, 0.02% EDTA in buffer, Biochrom AG, Berlin, Germany). The radioactivity in both media and cells was measured using an automated gamma-counter equipped with a 3-inch NaI(TI) detector (1480 WIZARD, Wallac Oy, Turku, Finland), and the fraction of cell-bound radioactivity was calculated. The data on cellular uptake was statistically assessed by an unpaired, two-tailed t-test using GraphPad Prism (version 4.00 for Windows GraphPad Software, San Diego Calif. USA) in order to determine any significant differences (p<0.05).

Results

Labeling of Z Variants:

Radiolabeling using an IsoLink kit provided a yield of 43±6% for $^{99m}$Tc(CO)$_3$-Z08698-His$_6$ and 73±12% $^{99m}$Tc (CO)$_3$-Z08699-His$_6$. After purification with disposable NAP-5 columns, the purity was more than 97% for both labeled conjugates.

Figure 6:
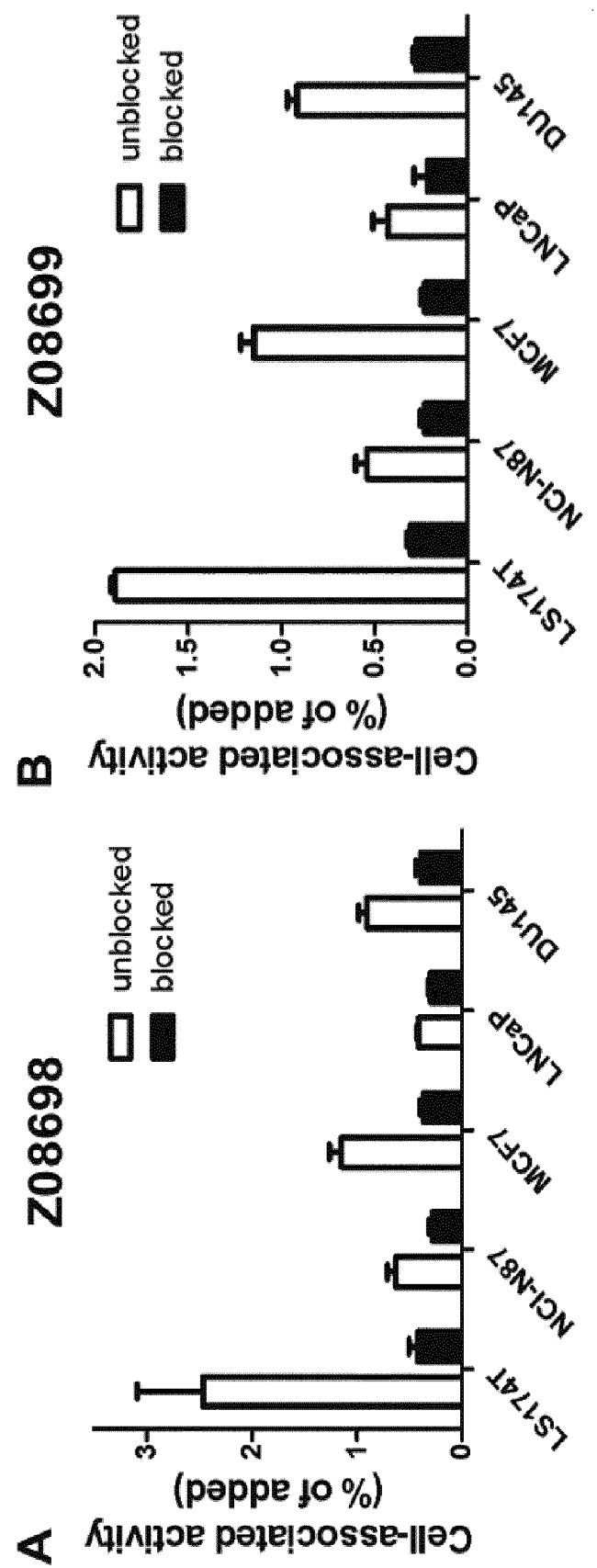
FIG. 6 shows the in vitro specificity of binding of radiolabeled Z variant molecules to various HER3-expressing cells as described in Example 4. Cells were incubated for 1 h with 1 nM of radiolabeled (A) Z08698 or (B) Z08699. For pre-saturation (blocking) of receptors, 0.7 µM nonlabeled Z variant molecules was added to a control group. Data are presented as percent of added radioactivity that is cell-bound (mean values of three cell dishes) and standard deviations are shown. The difference between uptake by non-blocked and blocked cells was statistically significant (p<0.05).

Binding Specificity of Labeled Z Variants to HER3 Expressing Cells:

Binding specificity tests were performed to assess if the binding of $^{99m}$Tc(CO)$_3$-Z08698-His$_6$ and $^{99m}$Tc(CO)$_3$-Z08699-His$_6$ to HER3-expressing cells was receptor mediated. Saturation of the receptors by pre-incubation with the same, but unlabeled, Z variant molecules, significantly (p<0.05) decreased the binding of the radiolabeled Z variant molecules, suggesting specific binding (FIG. 6).

Example 5

In Vivo Biodistribution Studies of HER3 Binding Z Variants

This Example describes in vivo studies performed in mice using radiolabeled conjugates of Z08698 and Z08699, demonstrated in Example 3 to cross-react with murine HER3. First, normal mice were used to study the biodistribution properties, as well as to test the specificity of in vivo accumulation of the two radiolabeled Z variant molecules in organs where HER3 is normally expressed, such as in lung, liver, stomach, small intestines and salivary gland. Second, the biodistribution and tumor targeting properties of radiolabeled Z08699 were further assessed in nude mice bearing a prostate cancer xenograft.

Materials and Methods

The biodistribution studies were performed using $^{99m}$Tc(CO)$_3$-Z08698-His$_6$ and $^{99m}$Tc(CO)$_3$-Z08699-His$_6$ Z variants labeled as described in Example 4. The animal studies were planned and performed in accordance with national legislation on laboratory animals' protection and approved by the local ethics committee for animal research.

Biodistribution Studies in Normal NMRI Mice:

$^{99m}$Tc(CO)$_3$-Z08698-His$_6$ or $^{99m}$Tc(CO)$_3$-Z08699-His$_6$ (65 kBq in 100 μl PBS per mouse) was intravenously injected in a group of four female NMRI mice (average weight 24.5±1.6 g). The injected protein dose was adjusted by dilution with non-labeled Z variant molecule to 1 μg (0.13 nmol) or 10 μg (1.3 nmol) per mouse. At 4 h post injection (pi), a group of four mice were sacrificed by injection of a lethal dose of anesthesia (20 μl of Ketalar-Rompun per gram body weight; Ketalar (50 mg/ml, Pfizer); Rompun (20 mg/ml, Bayer)) followed by heart puncture and exsanguination with a syringe rinsed with heparin (5000 IE/ml, Leo Pharma). Samples of blood, lung, liver, spleen, stomach, small intestines, kidney, uterus, salivary gland, muscle and bone were collected and weighed, and their radioactivity was measured using an automated gamma-counter equipped with a 3-inch NaI(Tl) detector (1480 WIZARD, Wallac Oy, Turku, Finland). Technetium-99m radioactivity was measured in the energy range of 100-160 keV. The data were corrected for background. The tissue uptake was calculated as percent of injected radioactivity per gram (% IA/g). Radioactivity in carcass was calculated as % IA per whole sample. The biodistribution data was statistically assessed by an unpaired, two-tailed t-test using Graph-Pad Prism (version 4.00 for Windows, GraphPad Software) in order to determine any significant differences (p<0.05).

Biodistribution Studies in Nude Tumor Bearing Mice:

HER3-expressing prostate cancer xenografts were used to study the in vivo tumor targeting properties of $^{99m}$Tc(CO)$_3$-Z08699-His$_6$. LNCaP cells (6×10$^6$) were implanted in the right hind leg of male BALB/C nu/nu mice in 50% Matrigel. The biodistribution experiments were performed 4 weeks after implantation, at tumor weights of 0.8±0.4 g. The average animal weight was 20.1±0.6 g at the time of the experiment. To evaluate if the uptake in HER3 expressing organs is saturable, $^{99m}$Tc(CO)$_3$-Z08699-His$_6$ (85 kBq in 100 μl PBS per mouse) was intravenously injected in a group of three mice. The injected protein dose was adjusted by dilution with non-labeled Z08699-His$_6$ molecule to 0.1 μg (0.013 nmol) or 1 μg (0.13 nmol) per mouse. The animals were sacrificed 6 h after injection, and the biodistribution was measured and analyzed as described above.

Results

Biodistribution Studies in Normal Mice:

The biodistribution of $^{99m}$Tc(CO)$_3$-Z08698-His$_6$ and $^{99m}$Tc(CO)$_3$-Z08699-His$_6$ was assessed 4 h after injection in female NMRI mice. Both conjugates were rapidly cleared from blood and non-HER3-expressing tissues, such as bone and muscle. In HER3-expressing tissues (lung, liver, stomach, small intestines and salivary gland), the uptake (% IA/g) of both conjugates was lower at the higher injected protein dose (10 μg, 1.3 nmol). This result indicates a saturable uptake, which is a strong evidence of HER3-specific targeting.

Figure 7:
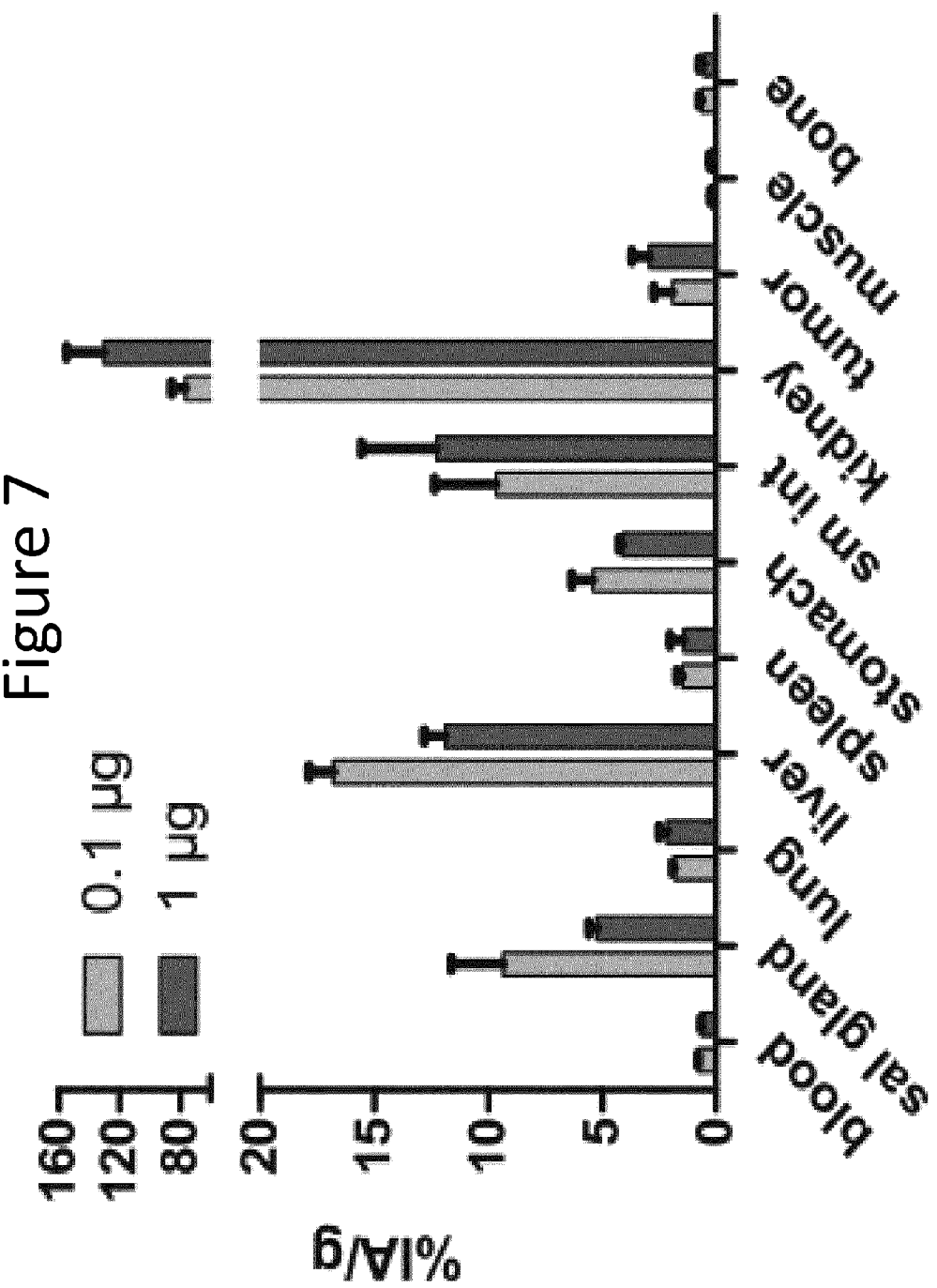
FIG. 7 shows data from the biodistribution study, performed as described in Example 5, of radiolabeled Z08699 in mice bearing LNCaP prostate cancer xenografts. Data from 6 h post injection are presented as percent of injected activity per gram (n=4) and the standard deviations are shown.

Biodistribution Studies in Tumor Bearing Mice:

The biodistribution data of $^{99m}$Tc(CO)$_3$-Z08699-His$_6$ in nude mice bearing LNCaP xenografts are presented in FIG. 7. In agreement with data for normal NMRI mice, increase of protein dose caused reduction of uptake in liver, stomach and salivary gland. There was a tendency to increased tumor uptake at a higher protein dose, but the increase was not statistically significant (1.9±0.8 versus 2.9±0.8% IA/g when injected at a dose of 0.1 μg and 1 μg, respectively). Increase of the protein dose resulted in significantly higher tumor-to-blood, tumor-to-salivary gland, tumor-to-liver and tumor-to-bone ratios. Taken together, the results of the biodistribution study in tumor-bearing mice suggest that for instance imaging of HER3 expression in prostate cancer is feasible using radiolabeled Z08699 for HER3 specific targeting. Thus, using the new generation high-affinity Z variants disclosed herein should provide a benefit e.g. over previously isolated HER3-specific Z variants, such as Z05416 and Z05417, which, despite having subnanomolar affinity for HER3, are believed not to provide sufficient contrast for imaging due to the relatively low expression of HER3 on tumor cells compared to in other tissues.

Example 6

Production of a Selection of HER3 Binding Z Variants in Fusion with an Albumin Binding Domain In this Example, two HER3 binding Z variants (Z08698 and Z08699) from the on-cell affinity ranking described in Example 2 and the two reference Z variants Z05416 and Z05417 were recloned as fusions with the albumin binding domain PP013 (SEQ ID NO:109), and purified from *E. coli* cell extracts.

Materials and Methods

Subcloning of Z Variants:

This was performed essentially as described in WO2009/077175 for other Z variants described therein. Monomeric Z variants were amplified from pAY01449 vectors. A subcloning strategy for construction of Z variant molecules with N-terminal and/or C-terminal fusions was applied using standard molecular biology techniques. A PCR was performed using different primer pairs and the resulting gene fragments were purified and hybridized in ligase buffer. The hybridized gene fragments were subcloned in the pAY03362 vector, providing a C-terminal PP013 fusion. The HER3 binding Z variants were subcloned as monomers, and the exact constructs encoded by the expression vectors were MGSSLQ-[Z#####]-VDSS-[PP013] (SEQ ID NO: 123).

Cultivation and Purification:

E. coli BL21(DE3) cells (Novagen) were transformed with plasmids containing the monomeric gene fragment of each respective Z variant and cultivated at 37° C. in 1 l of TSB+YE medium (Tryptic Soy Broth with Yeast Extract) supplemented with 50 µg/ml kanamycin. At $OD_{600}$=1, IPTG at a final concentration of 0.17 mM was added to induce protein expression and the cultivation was incubated at 37° C. for another 5 h. The cells were harvested by centrifugation. Cell pellets harboring the Z variants were resuspended in TST buffer (25 mM Tris-HCl, 1 mM EDTA, 200 mM NaCl, 0.05%, Tween 20, pH 8.0) with an addition of 7 U/ml BENZONASE (Merck, cat. no. 1.01654.001) and disrupted by ultrasonication. The lysates were clarified by centrifugation (>20 min, 25000 g, 4° C.) and loaded on 1 ml pre-packed affinity agarose, pre-equilibrated with TST buffer. After wash with 5 column volumes (CV) TST buffer, followed by 3 CV 5 mM $NH_4Ac$ pH 5.5, bound Z variants were eluted with 2 CV 0.1 M HAc. Each Z variant was transferred to PBS (2.68 mM KCl, 0.47 mM $KH_2PO_4$, 137 mM NaCl, 8.1 mM $Na_2HPO_4$, pH 7.4) on PD-10 Desalting Columns (GE Healthcare, cat. no. 17-0851-01). Protein concentrations were determined by measuring the absorbance at 280 nm, using a NANODROP ND-1000 spectrophotometer, and using the extinction coefficient of the respective protein. Purity of the final products was analyzed by SDS-PAGE stained with Coomassie Blue. Identity of each purified protein variant was determined using HPLC-MS analysis on an Agilent 1100 LC/MSD system (Agilent Technologies).

Results

Subcloning of Z Variants:

The Z variants were chosen for subcloning in the expression vector pAY03362. The cloning resulted in four fusion proteins comprising one of the four monomers Z05416, Z05417, Z08698 and Z08699 in fusion with the albumin binding domain PP013.

Cultivation and Purification:

The two inventive Z variants Z08698 and Z08699, constructed as monomers and with a C-terminal ABD, expressed well in E. coli. The amount of affinity-purified Z variants from 2 g bacterial pellets, determined spectrophotometrically by measuring the absorbance at 280 nm, ranged from 3 mg to 6 mg for the different Z variants. Purity of the produced Z variants was estimated to exceed 95% as assessed by SDS-PAGE analysis. The correct molecular weight of each protein variant was confirmed by HPLC-MS.

Example 7

Evaluation of the Inhibitory Capacity of HER3 Binding Z Variants in an In Vitro Proliferation Assay In this Example, Z variants Z08698 and Z08699, fused at their C-termini to PP013 as described in Example 6, were tested for their ability to inhibit heregulin induced proliferation in an in vitro assay using MCF-7 cells.

Materials and Methods

The Z variants Z08698, Z08699, Z05416 and Z05417, all produced as described in Example 6 with a C-terminal albumin binding fusion partner, were tested. The cell line MCF-7 (ATCC HTB-22) was propagated as recommended in complete medium (RPMI 1640 medium with L-glut (Lonza) supplemented with sodium pyruvate (Lonza), non-essential amino acids (Lonza), penicillin/streptomycin (Lonza) and 10% fetal calf serum (FCS) (Gibco)). At the day of experiment, the cells were washed twice in RPMI 1640 without supplements and resuspended in assay medium (RPMI 1640 medium with L-glut containing sodium pyruvate, non-essential amino acids, penicillin/streptomycin, 9 pM recombinant human serum albumin (rHSA, Novozymes)+2% dialysed FCS (Gibco)). The ability of the Z variants to block heregulin (HRG) induced proliferation was analyzed by mixing the Z variants with 200 pM HRG (NRG1-J31/HRG1-J31 EGF domain, R&D Systems) in assay medium. The molecules were titrated in a 5-fold dilution series with a fixed concentration of HRG (200 pM). The titration was performed in 96-well cell culture plates in a volume of 100 µl. 1500 cells were added per well (100 µl) and plates were incubated at 37° C., 5% $CO_2$ for five days. After incubation, determination of the number of living cells in each well was performed using cell counting kit-8 (CCK-8, Fluka, Sigma Aldrich). 19 µl of CCK-8 cell proliferation reagent diluted two times in RPMI 1640 medium was added per well and absorbance was measured after 4 h at 450 nm using a microplate reader (Victor3, Perkin Elmer). The data on cell growth was assessed by non-linear regression to a four-parameter dose-response curve, and the half maximal inhibitory concentration (IC50) was determined using GraphPad Prism (version 5.01 for Windows, GraphPad Software).

Results

Figure 8:
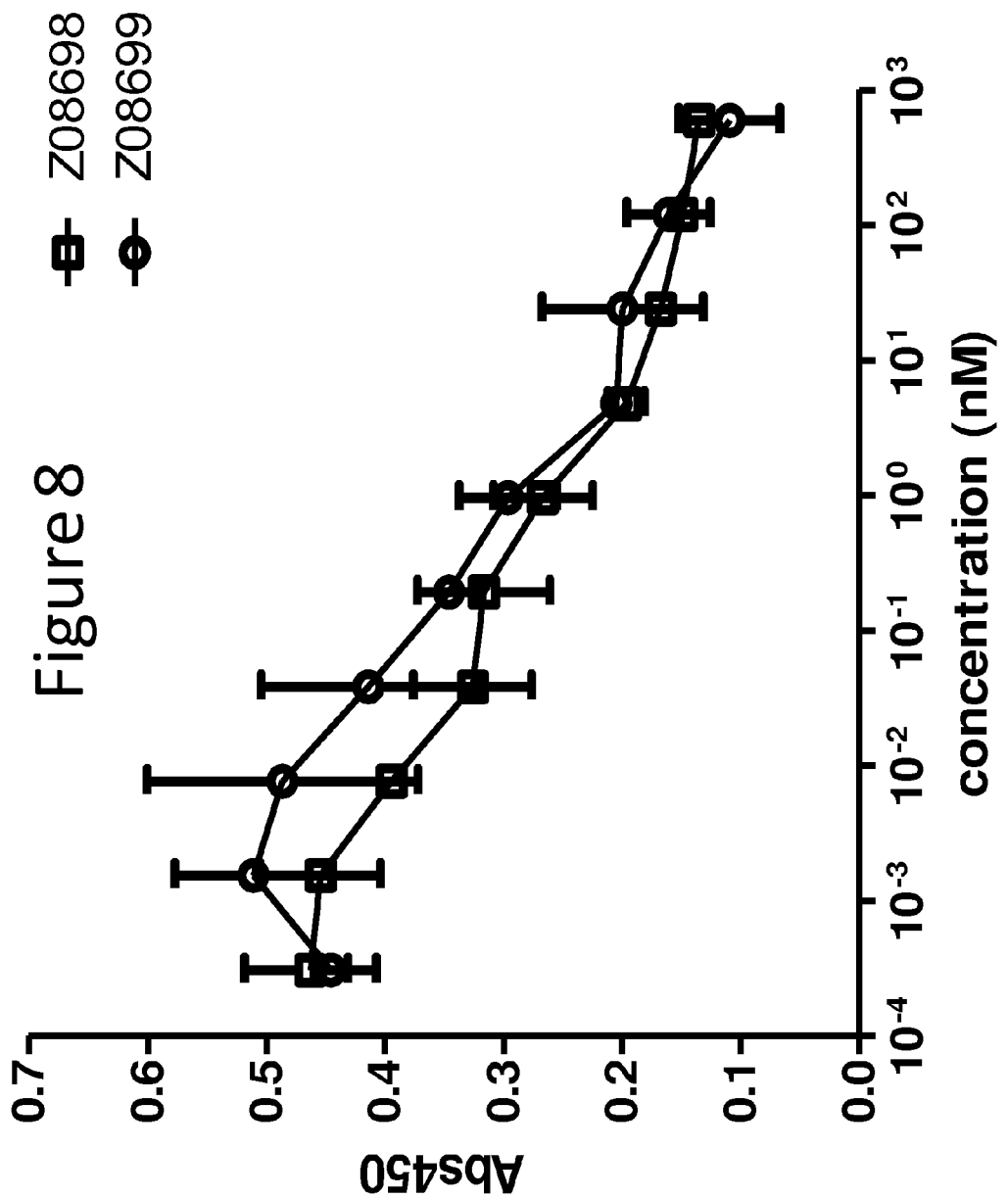
FIG. 8 shows the results from the inhibition of heregulin induced proliferation with the two Z variants Z08698 (open squares) and Z08699 (open circles) as described in Example 7. A dilution series of each binder was mixed with a fixed concentration of HRG (200 pM) and incubated with MCF-7 cells for five days in the presence of rHSA. The mean absorbance values±SD, which are proportional to the number of living cells, is represented on the y-axis and the concentration of the Z variants is represented on the x-axis.

Evaluation in HRG Induced Proliferation Assay:

The results are shown in FIG. 8. The half maximal inhibitory concentration, IC50, of the Z variants Z08698 and Z08699 in fusion with an albumin binding domain were determined in an HRG induced proliferation assay. A dilution series of each binder was mixed with a fixed concentration of HRG and incubated with MCF-7 cells for five days in the presence of rHSA. The IC50 values were determined by non-linear regression to a four-parameter dose-response curve. The obtained IC50 values for Z08698 and Z08699 were 0.4 nM and 0.6 nM respectively, representing an improvement in in vitro blocking capacity of approximately 100-fold and 70-fold, respectively, compared to the reference polypeptide Z05417.

Example 8

In Vitro Cell Assay Assessing the Inhibitory Capacity of HER3 Binding Z Variants in a HER3 Phosphorylation Assay In this Example, Z variants Z08698 and Z08699 produced with a C-terminal albumin binding domain were tested for their ability to inhibit HER3 phosphorylation.

Materials and Methods

The Z variants Z08698 and Z08699 were produced as described in Example 6 with a C-terminal PP013 fusion partner and tested. The cell line MCF-7 was propagated as recommended in complete medium.

Cell Lysate Production:

MCF-7 cells were seeded in 60×15 mm cell culture dishes (Corning) at a concentration of $1 \times 10^6$ cells/5 ml and allowed to grow for 24 h in complete medium. The medium was exchanged for assay medium 4 h prior to the start of the experiment. Z variants Z08698 and Z08699 were diluted to 4, 40 and 400 nM in assay medium with a fixed concentration of HRG (4 nM) and incubated with the cells for 10 min at 37° C. The cells were kept on ice and washed twice with ice cold PBS. The cells were loosened with a cell scraper in 2 ml of ice cold PBS with 1 mM activated sodium orthovanadate (Sigma), transferred to a tube and centrifugated at 400 g for 3 min in a pre-cooled (4° C.) centrifuge. The supernatant was discarded and 100 µl lysis buffer (1% NP-40, 20 mM Tris (pH 8.0), 137 mM NaCl, 10% glycerol, 2 mM EDTA, 1 mM activated sodium orthovanadate) was added per $10^6$ cells. After a 30 min incubation at 4° C., the samples were centrifuged in eppendorf tubes at 13000×g for 15 min in a pre-cooled (4° C.) centrifuge. The supernatant from each tube was collected and used in phospho-HER3 ELISA as follows.

Phospho-HER3 ELISA:

Human Phospho-ErbB3 ELISA kit (R&D Systems) for detection of phosphorylated HER3 was used according to the manufacturer's instructions. 96-well half area plates were coated with an anti-HER3 antibody, 4 µg/ml in PBS at room temperature overnight. The plate was washed and blocked with 1% BSA in PBS for 2 h at room temperature. After washing, 50 µl of cell lysate diluted 1:20 in "diluent #12" (1% NP-40, 20 mM Tris (pH 8.0), 137 mM NaCl, 10% glycerol, 2 mM EDTA, 1 mM activated sodium orthovanadate) was added to each well. The plate was incubated for 2 h, washed and incubated with HRP-labeled anti phosphotyrosine antibody, diluted 1:2000 in "diluent #14" (20 mM Tris, 137 mM NaCl, 0.05% Tween 20, 0.1% BSA, pH 7.2-7.4), for 2 h. The plate was washed and substrate added (R&D Systems). After about 20 min, the reaction was stopped with 2 M $H_2SO_4$ and the plate was read using a microplate reader (Victor3, Perkin Elmer) at 450 and 570 nm.

Results

Figure 9:
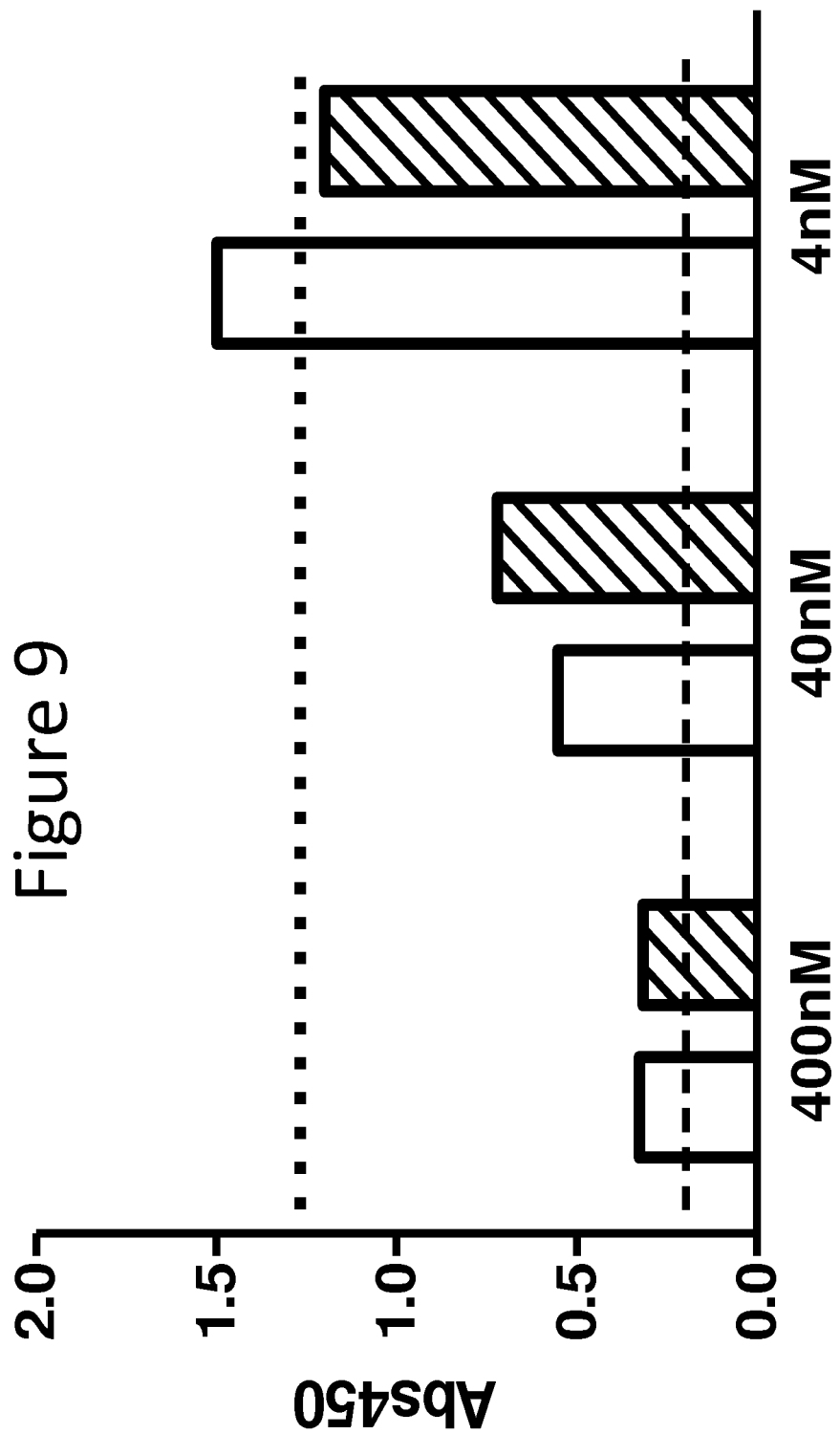
FIG. 9 shows the results from the HER3 phosphorylation assay described in Example 8, wherein the inhibitory capacity of Z variants Z08698 (open bar) and Z08699 (striped bar) was evaluated in the presence of 4 nM HER3 and rHSA. Data is given in mean absorbance values±SD, which are proportional to the amount of phosphorylated HER3. The dotted line indicates the response induced by the positive control (4 nM HRG). The striped line indicates the response induced by the negative control (assay medium).

HER3 Phosphorylation Assay:

The results are shown in FIG. 9. The capacity to inhibit HRG induced HER3 phosphorylation in MCF-7 cells was determined. A dilution series of each binder was mixed with a fixed concentration of HRG and incubated with MCF-7 cells for 10 min in the presence of rHSA. At a concentration of 400 nM, Z variants Z08698 and Z08699 inhibited HER3 phosphorylation by 89%. The effect was declining with the concentration of Z variants, and at 40 nM, Z08698 and Z08699 inhibited HER3 phosphorylation by 67% and 51%, respectively. At 4 nM, the effect was lost. These results represent an improvement in in vitro blocking capacity, as assessed by phosphorylation, of approximately 10-fold compared to the reference polypeptide Z05417.

Example 9

Evaluation of the Inhibitory Capacity of Dimeric HER3 Binding Z Variants

In this Example, dimeric Z variants comprising Z08698 in fusion with the albumin binding PP013 in the format Z-PP013-Z was tested for their ability to inhibit heregulin induced signaling in an in vitro assay using MCF-7 cells. Two different linker lengths with one or four repeats, respectively, of GGGGS between the Z and the albumin binding moieties were assessed i.e. Z08698-$G_4$S-PP013-$G_4$S-Z08698 (SEQ ID NO: 126) and Z08698-$(G_4S)_4$-PP013-$(G_4S)_4$-Z08698 (SEQ ID NO: 127).

Materials and Methods

Cloning and Production:

Subcloning of dimeric Z variants was performed essentially as described in Example 6 and applying standard molecular biology techniques using primers incorporating NdeI and AscI restriction sites. The HER3 binding Z variants were subcloned as dimers in fusion with PP013, and the exact constructs encoded by the expression vectors were M-[Z08698]-GAP(GGGGS)TS-[PP013]-GT(GGGGS)PR-[Z08698] (SEQ ID NO: 124) and M-[Z08698]-GAP$(GGGGS)_4$TS-[PP013]-GT$(GGGGS)_4$PR-[Z08698] (SEQ ID NO: 125), respectively. The protein variants were expressed in E. coli and purified essentially as described in Example 6, but with the addition of a preparative reverse phase high-performance liquid chromatography (RP-HPLC) purification step after the affinity chromatography step and prior to final buffer exchange to PBS.

In Vitro Cell Assay:

MCF-7 cells (ATCC HTB-22) were trypsinated and seeded at 25000 cells per well in an EnSpire-LFC microplate (Perkin Elmer, cat no 6055408) and allowed to grow for 20 h at 37° C. in complete medium. At the day of experiment, the cells were washed once with Hank's balanced salt solution (HBSS; Sigma, cat. no. H9269). 100 µl HBSS was added per well and the plates were incubated at ambient temperature for 1.5 h inside the EnSpire Instrument (Perkin Elmer) to be used for assay readout. The ability of Z08698-$G_4$S-PP013-$G_4$S-Z08698 (SEQ ID NO: 126) and Z08698-$(G_4S)_4$-PP013-$(G_4S)_4$-Z08698 (SEQ ID NO: 127), respectively, to block heregulin induced signaling was analyzed by mixing these Z-PP013-Z variants with 1 nM HRG in HBSS. The monomeric Z08698-PP013 was included for comparison. The molecules were titrated in a 5-fold dilution series with a fixed concentration of HRG (1 nM) in a final assay volume of 130 µl/well. The redistribution of dynamic mass upon addition of stimuli was recorded by an EnSpire Instrument every 60 s for 1 h. The half maximal inhibitory concentrations (IC50) were determined from the dose response curves.

Results

The obtained IC50 values for Z08698-$G_4$S-PP013-$G_4$S-Z08698 (SEQ ID NO: 126), Z08698-$(G_4S)_4$-PP013-$(G_4S)_4$-Z08698 (SEQ ID NO: 127) and Z08698-PP013 were 0.7 nM, 0.6 nM and 1 nM respectively. Thus, the capacity to inhibit heregulin induced signaling was increased by the dimeric constructs in the format Z-PP013-Z. The effect of linker length between the Z and albumin binding moieties was marginal. The IC50 value for the Z08698-PP013 variant (1 nM) is in line with the result obtained in the proliferation assay described in Example 7, where it was shown to be superior to the reference polypeptide Z05417-PP013.

Example 10

Imaging of HER3-Expressing Xenografts in Mice Using $^{99m}$Tc(CO)$_3$-Labeled Z Variant In this Example, the feasibility of using a radiolabelled HER3 specific Z variant for imaging was investigated. Z08699 with a HEHEHE-tag on the N-terminus was labeled with $^{99m}$Tc(CO)$_3$ and injected into LS174T colorectal carcinoma xenograft mouse. Tumors were visualized by microSPECT/CT 4 h post injection.

Materials and Methods

Cloning, Production and Labeling of Z Variant:

DNA encoding Z08699 was amplified by PCR using primers incorporating NdeI and XhoI restriction sites and codons for an N-terminal HEHEHE-tag. Subcloning and production of HEHEHE-Z08699 (SEQ ID NO: 128) was performed essentially as described in Example 3, but with the addition of a preparative reverse phase high-performance liquid chromatography (RP-HPLC) purification step after the IMAC purification. A histidyl-glytamyl-histidyl-glytamyl-histidyl-glytamyl-(HEHEHE)-tag was selected instead of a $His_6$ tag because it has a more favorable biodistribution profile, in particular reduced hepatic uptake, but yet allows IMAC-purification (Tolmachev et al, Bioconjug Chem 21:2013-2022 (2010)). Labeling with $^{99m}$Tc (CO)$_3$ using an IsoLink kit was performed as described in Example 4.

In Vivo Imaging:

A Balb/c nu/nu mouse bearing a subcutaneous LS174T colorectal carcinoma xenograft, was injected with $^{99m}$Tc (CO)$_3$-HEHEHE-Z08699 (1.6 MBq/1 µg). 4 h post injection, the animal was euthanized and the urinary bladder was excised post-mortem to improve image quality. Static whole body tomographical examinations was then performed by microSPECT (FOV: 8 cm, 75A10 collimators, acquisition over 200-250 keV, 32 projections). The animal was examined by CT for anatomical correlation.

Results

Figure 10:
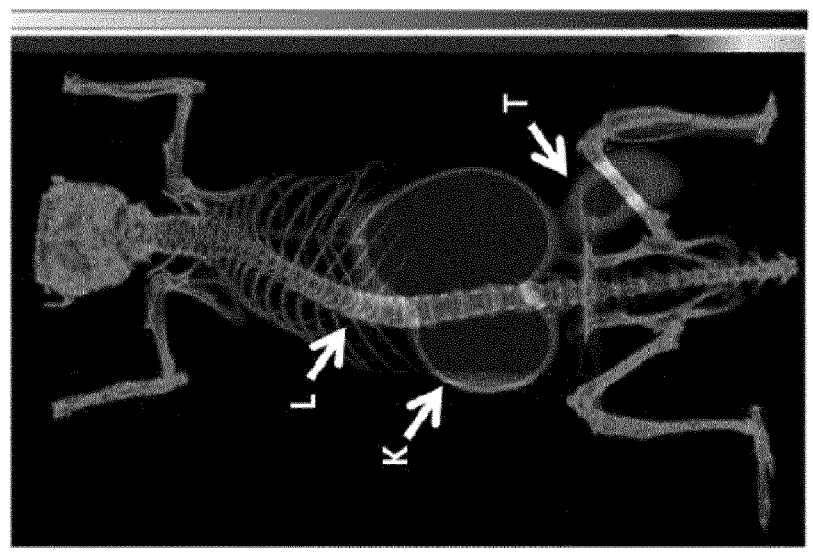
FIG. 10 shows imaging of HER3 expression in LS174T colorectal carcinoma xenografts in mouse using radiolabeled Z08699 variant ($^{99m}$Tc(CO)$_3$-HEHEHE-Z08699) as described in Example 10. The microSPECT/CT image was acquired 4 h after injection. Arrows point at liver (L), kidneys (K), and tumor (T).

A microSPECT image acquired 4 h after administration of $^{99m}$Tc(CO)$_3$-HEHEHE-Z08699 to tumor bearing mouse (LS174T colorectal carcinoma xenograft) is presented in FIG. 10. The tumor was clearly visualized. Accumulation of radioactivity in kidneys and liver is also seen.

Example 11

Imaging of HER3-Expressing Xenografts in Mice Using $^{111}$In-Labeled Z Variants In this Example, the feasibility of using radiolabeled HER3 specific Z variants for imaging was investigated further. The NOTA chelator, forming a stable complex with a number of radionuclides suitable for SPECT or PET imaging, was conjugated to HEHEHE-Z08698 (SEQ ID NO: 129) and HEHEHE-Z08699 (SEQ ID NO: 128) via a unique C-terminal cysteine. The molecules were labeled with $^{111}$In and injected into BT474 breast carcinoma xenograft mice. Tumors were visualized by SPECT gamma camera imaging 4 h post injection.

Materials and Methods

Cloning and Production of NOTA Coupled Z Variants:

HEHEHE-Z08698 (SEQ ID NO: 129) and HEHEHE-Z08699 (SEQ ID NO: 128), each with a C-terminal cysteine residue were cloned and expressed essentially as described in Example 3. Harvested cells were resuspended in 1×PBS and disrupted by the use of a French press. The samples were heat treated up to 70° C. and incubated for 10 min, followed by cooling on ice for 10 min. The lysates were clarified by centrifugation (10 min, 30000 g, 4° C.). The cysteines of the Z variants were reduced with DTT, 20 mM for 30 min at 40° C. Excess DTT was removed by buffer exchange on PD-10 columns to 20 mM $NH_4$ acetate, pH 5.5. The NOTA conjugation was performed with a three-fold molar excess of chelator, maleimide-NOTA (CheMatech, cat. no. C101). The mixture was incubated for 40 min at 40° C. Purification from non-conjugated chelators was performed by RP-HPLC. The correct molecular weight of each NOTA-coupled Z variant was confirmed by HPLC-MS and CD measurements were performed to verify preserved structural integrity.

Labelling with $^{111}$In:

HEHEHE-Z08698-NOTA (SEQ ID NO: 130) or HEHEHE-Z08699-NOTA (SEQ ID NO: 131) (40 µg, 6 nmol) in 100 µl 20 mM $NH_4$ acetate, pH 5.5 was mixed with 54 µl $^{111}$In-chloride solution (40 MBq). The mixture was incubated at 85° C. for 1 h. The labeling efficiency was analyzed by ITLC (as described in Example 4) eluted with 0.2 M citric acid, pH 2.0. The conjugates were purified using disposable NAP-5 columns (GE Healthcare) according to manufacturer's instructions.

In Vivo Imaging:

Tumor-bearing mice (BT474 breast carcinoma xenograft) were injected with 1 µg (0.8 MBq) $^{111}$In-HEHEHE-Z08698-NOTA (SEQ ID NO: 132) or $^{111}$In-HEHEHE-Z08699-NOTA (SEQ ID NO: 133). 4 h pi, the animals were euthanized and the urinary bladders were excised post-mortem to improve image quality. Static planar imaging was performed using a GE Infinia gamma camera equipped with a medium energy general purpose (MEGP) collimator. Static image (20 min) was obtained with a zoom factor of 3 in a 256×256 matrix.

Results

The correct molecular weight of each NOTA-conjugated Z variant was confirmed by HPLC-MS and purity was found to exceed 95%. CD measurements verified preserved helical structure as well as reversible folding after heating up to 90° C. The radiochemical yields of $^{111}$In-HEHEHE-Z08698-NOTA (SEQ ID NO: 132) and $^{111}$In-HEHEHE-Z08699-NOTA (SEQ ID NO: 133) were 97% and 96%, respectively.

Figure 11:
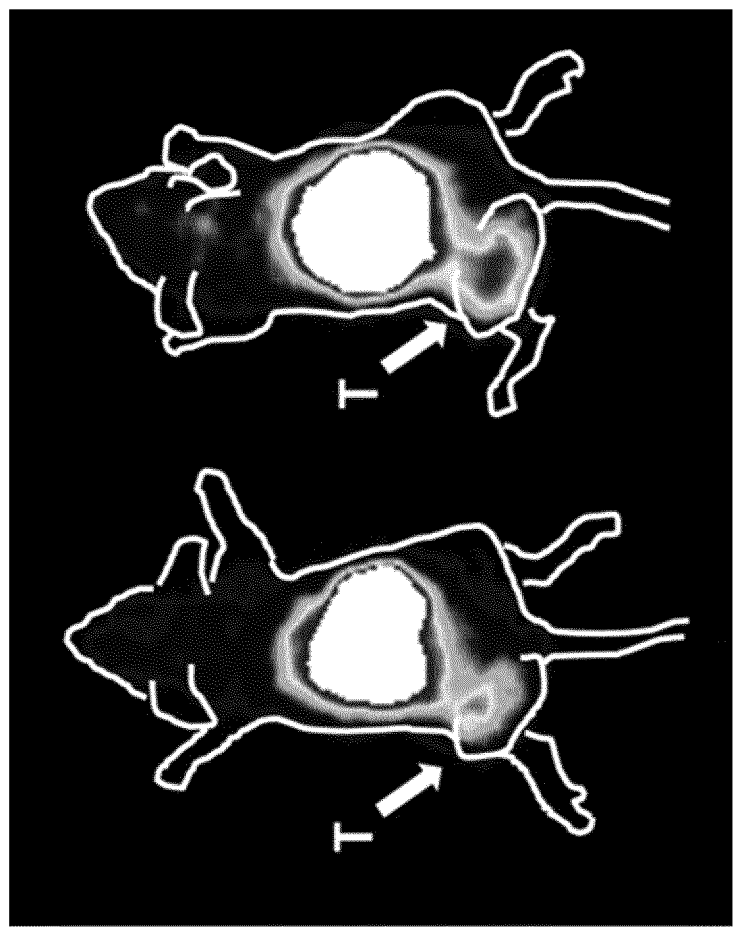
FIG. 11 shows gamma camera images of mice bearing HER3 expressing BT474 xenografts, 4 h post injection of 1 μg (0.8 MBq) $^{111}$In HEHEHE-Z08698-NOTA (SEQ ID NO: 132) (left) and $^{111}$In-HEHEHE-Z08699-NOTA (SEQ ID NO: 133) (right).

Gamma-camera images of tumor-bearing mice 4 h post injection of $^{111}$In-HEHEHE-Z08698-NOTA (SEQ ID NO: 132) and $^{111}$In-HEHEHE-Z08699-NOTA (SEQ ID NO: 133), respectively, are shown in FIG. 11. The tumors were clearly visualized and the images showed high renal clearance with little background in blood and other organs except liver and kidneys. The blood clearance was better for $^{111}$In-HEHEHE-Z08698-NOTA (SEQ ID NO: 132), which resulted in lower background radioactivity.

To conclude, the results disclosed in Examples 10 and 11 show that radionuclide imaging of HER3 expression in malignant tumors is feasible using the HER3 specific high affinity Z variants disclosed herein, despite low HER3 expression in tumors and background expression in normal tissues. Improved imaging contrast may be obtained by optimizing labeling chemistry and tracer dosing.

Example 12

Inhibition of Tumor Growth In Vivo by Administration of HER3 Binding Z Variant

To show that a HER3 binding Z variant as disclosed herein inhibits tumor growth in vivo, the Z variant is administered to xenografted mice and tumor growth is monitored. One useful such HER 3-expressing tumor model is the ACHN xenograft model.

To obtain cells for xenograft experiments, ACHN cells (CRL-1611, LGC standards) are cultured in vitro in MEM medium (Lonza, cat no 12-611) containing 10% fetal calf serum. ACHN tumors are established by subcutaneous injection of $5-10×10^6$ ACHN cells into the right flank of NMRI nu/nu mice (Charles River). Tumor volume is measured using calipers to measure the length and width of tumors three times a week. The tumor volume is calculated as length×width$^2$×0.44. According to generally accepted principles, the study is started when tumor volume reaches approximately 200 mm$^3$. Mice are randomized into groups containing similar size distribution of the tumors.

To inhibit tumor growth with a HER3 binding Z variant, mice (10 per group) are injected intravenously with 20, 2 or 0.2 mg/kg of endotoxin free Z variant or vehicle control (PBS buffer). The injections are repeated three times per week during three weeks. The therapeutic effect is followed by measuring tumor volume three times weekly using calipers, and the body weight of each mouse is simultaneously recorded. The difference in average tumor volume between treated and vehicle groups at the end of study is assessed by Students t-test.

The results of the experiment above is expected to show a dose dependent inhibition of tumor growth by the HER3 binding Z variant disclosed herein.

ITEMIZED LISTING OF EMBODIMENTS

1. HER3 binding polypeptide, comprising a HER3 binding motif (BM), which motif consists of an amino acid sequence selected from:
i)   EKYX$_4$AYX$_7$EIW   X$_{11}$LPNLTX$_{17}$X$_{18}$QX$_{20}$ AAFIGX$_{26}$LX$_{28}$D (SEQ ID NO: 110)
wherein, independently of each other,
X$_4$ is selected from A, E, L, M, N Q, R, S and T;
X$_7$ is selected from F and Y;
X$_{11}$ is selected from E and Q;
X$_{17}$ is selected from K, N, R and V;
X$_{18}$ is selected from F, M, N, R, T, Y and W;
X$_{20}$ is selected from A and K;
X$_{26}$ is selected from K and S;
X$_{28}$ is selected from E and Q; and
ii) an amino acid sequence which has at least 96% identity to the sequence defined in i).

2. HER3 binding polypeptide according to item 1, wherein in sequence i), independently from each other,
X$_4$ is selected from A, E, M, N, Q, S and T;
X$_7$ is selected from F and Y;
X$_{11}$ is Q;
X$_{17}$ is selected from K and R;
X$_{18}$ is selected from M, Y and W;
X$_{20}$ is K;
X$_{26}$ is K;
X$_{28}$ is Q.

3. HER3 binding polypeptide according to item 1, wherein X$_4$ in sequence i) is selected from A, E, M, N, Q, S and T.

4. HER3 binding polypeptide according to any preceding item, wherein X$_4$ in sequence i) is selected from N and Q.

5. HER3 binding polypeptide according to item 4, wherein X$_4$ in sequence i) is N.

6. HER3 binding polypeptide according to item 4, wherein X$_4$ in sequence i) is Q.

7. HER3 binding polypeptide according to any preceding item, wherein X$_{11}$ in sequence i) is Q.

8. HER3 binding polypeptide according to any preceding item, wherein X$_{17}$ in sequence i) is selected from K, N and R, such as selected from K and R.

9. HER3 binding polypeptide according to item 8, wherein X$_{17}$ in sequence i) is K.

10. HER3 binding polypeptide according to item 8, wherein X$_{17}$ in sequence i) is R.

11. HER3 binding polypeptide according to any preceding item, wherein X$_{18}$ in sequence i) is selected from M, Y and W.

12. HER3 binding polypeptide according to any item 11, wherein X$_{18}$ in sequence i) is selected from Y and W.

13. HER3 binding polypeptide according to item 12, wherein X$_{18}$ in sequence i) is Y.

14. HER3 binding polypeptide according to item 12, wherein X$_{18}$ in sequence i) is W.

15. HER3 binding polypeptide according to item 11, wherein X$_{18}$ in sequence i) is M.

16. HER3 binding polypeptide according to any preceding item, wherein X$_{17}$X$_{18}$ in sequence i) is selected from KW, KY, KM and RY.

17. HER3 binding polypeptide according to any preceding item, wherein X$_{20}$ in sequence i) is K.

18. HER3 binding polypeptide according to any preceding item, wherein X$_{26}$ in sequence i) is K.

19. HER3 binding polypeptide according to any preceding item, wherein X$_{28}$ in sequence i) is Q.

20. HER3 binding polypeptide according to any preceding item, wherein sequence i) fulfills at least two of the following four conditions I, II, III and IV:
I) X$_{11}$ is Q;
II) X$_{17}$X$_{18}$ is selected from KW, KY, KM and RY;
III) X$_{20}$ is K;
IV) X$_{28}$ is Q.

21. HER3 binding polypeptide according to item 20, which fulfills at least three of said four conditions I, II, III and IV.

22. HER3 binding polypeptide according to item 21, which fulfills all of said four conditions I, II, III and IV.

23. HER3 binding polypeptide according to any preceding item, wherein sequence i) is selected from any one of SEQ ID NO:1-35.

24. HER3 binding polypeptide according to item 23, wherein sequence i) is selected from any one of SEQ ID NO:1-10.

25. HER3 binding polypeptide according to item 24, wherein sequence i) is selected from SEQ ID NO:1 and SEQ ID NO:2.

26. HER3 binding polypeptide according to item 25, wherein sequence i) is SEQ ID NO:2.

27. HER3 binding polypeptide according to item 25, wherein sequence i) is SEQ ID NO:1.

28. HER3 binding polypeptide according to any preceding item, wherein said HER3 binding motif forms part of a three-helix bundle protein domain.

29. HER3 binding polypeptide according to item 28, wherein said HER3 binding motif essentially forms part of two helices with an interconnecting loop, within said three-helix bundle protein domain.

30. HER3 binding polypeptide according to item 29, wherein said three-helix bundle protein domain is selected from bacterial receptor domains.

31. HER3 binding polypeptide according to item 30, wherein said three-helix bundle protein domain is selected from domains of protein A from *Staphylococcus aureus* or derivatives thereof.

32. HER3 binding polypeptide according to any preceding item, which comprises an amino acid sequence selected from:
iii) K-[BM]-DPSQS X$_a$X$_b$LLX$_c$ EAKKL NDX$_d$Q (SEQ ID NO: 111);
wherein
[BM] is a HER3 binding motif as defined by any one of items 1-27;
X$_a$ is selected from A and S;
X$_b$ is selected from N and E;
X$_c$ is selected from A, S and C;
X$_d$ is selected from A and S; and
iv) an amino acid sequence which has at least 89% identity to the sequence defined in iii).

33. HER3 binding polypeptide according to item 32, wherein X$_a$ in sequence iii) is A.

34. HER3 binding polypeptide according to item 32, wherein X$_a$ in sequence iii) is S.

35. HER3 binding polypeptide according to any one of items 32-34, wherein $X_b$ in sequence iii) is N.

36. HER3 binding polypeptide according to any one of items 32-34, wherein $X_b$ in sequence iii) is E.

37. HER3 binding polypeptide according to any one of items 32-36, wherein $X_c$ in sequence iii) is A.

38. HER3 binding polypeptide according to any one of items 32-36, wherein $X_c$ in sequence iii) is S.

39. HER3 binding polypeptide according to any one of items 32-36, wherein $X_c$ in sequence iii) is C.

40. HER3 binding polypeptide according to any one of items 32-39, wherein $X_d$ in sequence iii) is A.

41. HER3 binding polypeptide according to any one of items 32-39, wherein $X_d$ in sequence iii) is S.

42. HER3 binding polypeptide according to item 32, wherein, in sequence iii), $X_a$ is A; $X_b$ is N; $X_c$ is A and $X_d$ is A.

43. HER3 binding polypeptide according to item 32, wherein, in sequence iii), $X_a$ is A; $X_b$ is N; $X_c$ is C and $X_d$ is A.

44. HER3 binding polypeptide according to item 32, wherein, in sequence iii), $X_a$ is S; $X_b$ is E; $X_c$ is S and $X_d$ is S.

45. HER3 binding polypeptide according to item 32, wherein, in sequence iii), $X_a$ is S; $X_b$ is E; $X_c$ is C and $X_d$ is S.

46. HER3 binding polypeptide according to any one of items 32-45, wherein sequence iii) is selected from any one of SEQ ID NO:36-70.

47. HER3 binding polypeptide according to item 46, wherein sequence iii) is selected from any one of SEQ ID NO:36-45.

48. HER3 binding polypeptide according to item 47, wherein sequence iii) is selected from SEQ ID NO:36 and SEQ ID NO:37.

49. HER3 binding polypeptide according to item 48, wherein sequence iii) is SEQ ID NO:37.

50. HER3 binding polypeptide according to item 48, wherein sequence iii) is SEQ ID NO:36.

51. HER3 binding polypeptide according to any one of items 1-32, which comprises an amino acid sequence selected from:
v) YAK-[BM]-DPSQS SELLX$_c$ EAKKL NDSQA P (SEQ ID NO: 112);
wherein [BM] is a HER3 binding motif as defined in any one of items 1-27 and $X_c$ is selected from S and C; and
vi) an amino acid sequence which has at least 90% identity to the sequence defined in v).

52. HER3 binding polypeptide according to any one of items 1-32, which comprises an amino acid sequence selected from:
vii) FNK-[BM]-DPSQS ANLLX$_c$ EAKKL NDAQA P (SEQ ID NO: 113);
wherein [BM] is a HER3 binding motif as defined in any one of items 1-27 and $X_c$ is selected from A and C; and
viii) an amino acid sequence which has at least 90% identity to the sequence defined in vii).

53. HER3 binding polypeptide according to any one of items 1-31, which comprises an amino acid sequence selected from: ADNNFNK-[BM]-DPSQSANLLSEAKKL-NESQAPK (SEQ ID NO: 114); ADNKFNK-[BM]-DPSQSANLLAEAKKLNDAQAPK (SEQ ID NO: 115); ADNKFNK-[BM]-DPSVSKEILAEAKKLNDAQAPK (SEQ ID NO: 116); ADAQQNNFNK-[BM]-DPSQSTNV-LGEAKKLNESQAPK (SEQ ID NO: 117); AQHDE-[BM]-DPSQSANVLGEAQKLNDSQAPK (SEQ ID NO: 118); VDNKFNK-[BM]-DPSQSANLLAEAKKLNDAQAPK (SEQ ID NO: 119); VDAKYAK-[BM]-DPSQSSELLAE-AKKLNDAQAPK (SEQ ID NO: 120); and AEAKYAK-[BM]-DPSESSELLSEAKKLNKSQAPK (SEQ ID NO: 121); wherein [BM] is a HER3 binding motif as defined in any one of items 1-27.

54. HER3 binding polypeptide according to any one of items 1-51, which comprises an amino acid sequence selected from:
ix) AEAKYAK-[BM]-DPSESSELLSEAKKLNKSQAPK (SEQ ID NO: 121);
wherein [BM] is a HER3 binding motif as defined in any one of items 1-27, and
x) an amino acid sequence which has at least 91% identity to the sequence defined in ix).

55. HER3 binding polypeptide according to item 54, wherein sequence ix) is selected from SEQ ID NO:71-105.

56. HER3 binding polypeptide according to item 55, wherein sequence ix) is selected from SEQ ID NO:71-80.

57. HER3 binding polypeptide according to item 56, wherein sequence ix) is selected from SEQ ID NO:71 and SEQ ID NO:72.

58. HER3 binding polypeptide according to item 57, wherein sequence ix) is SEQ ID NO:72.

59. HER3 binding polypeptide according to item 57, wherein sequence ix) is SEQ ID NO:71.

60. HER3 binding polypeptide according to any preceding item, wherein the off-rate ($k_{off}$) of the interaction between said HER3 binding polypeptide and human HER3 is at least four-fold reduced, when compared to the off-rate ($k_{off}$) of the interaction between a comparative HER3 binding polypeptide comprising the amino acid sequence SEQ ID NO:107 and human HER3, as measured using the same experimental conditions.

61. HER3 binding polypeptide according item 60, wherein said off-rate ($k_{off}$) is at least 8-fold reduced, such as at least 12-fold reduced, such as at least 15-fold reduced.

62. HER3 binding polypeptide according to item 61, wherein said off-rate ($k_{off}$) is at least 20-fold reduced.

63. HER3 binding polypeptide according to any preceding item, wherein the $K_D$ value of the interaction between said HER3 binding polypeptide and human HER3 is at most $1 \times 10^{-9}$ M, such as at most $1 \times 10^{-10}$ M, such as at most $1 \times 10^{-11}$ M.

64. HER3 binding polypeptide according to any preceding item, further comprising at least one additional amino acid residue.

65. Fusion protein or conjugate comprising
a) a first moiety consisting of a HER3 binding polypeptide according to any preceding item; and
b) a second moiety consisting of a polypeptide having a desired biological activity.

66. Fusion protein or conjugate according to item 65, wherein said desired biological activity is a therapeutic activity.

67. Fusion protein or conjugate according to item 65, wherein said desired biological activity is a binding activity.

68. Fusion protein or conjugate according to item 65, wherein said desired biological activity is an enzymatic activity.

69. Fusion protein or conjugate according to item 66, wherein the second moiety having a desired biological activity is a therapeutically active polypeptide.

70. Fusion protein or conjugate according to item 65, wherein the second moiety having a desired biological activity is selected from the group consisting of human endogenous enzymes, hormones, growth factors, chemokines, cytokines and lymphokines.

71. Fusion protein or conjugate according to item 67, wherein the second moiety having a binding activity is a binding polypeptide capable of selective interaction with a target molecule.

72. Fusion protein or conjugate according to item 71, wherein said target molecule is selected from the group consisting of albumin, HER3, HER2, EGFR, IGF1R, cMet, VEGFR and PDGFR.

73. Fusion protein or conjugate according to any one of items 65-72, comprising a further moiety consisting of a polypeptide having a further, desired biological activity, which may be the same as or different from that of the second moiety.

74. Fusion protein or conjugate according to item 73, wherein the second moiety is as defined in any one of items 66-70, and the further moiety is as defined in any one of items 71-72.

75. Fusion protein or conjugate according to item 73, wherein the second moiety and the further moiety each individually is as defined in any one of items 71-72.

76. HER3 binding polypeptide, fusion protein or conjugate according to any preceding item, further comprising a cytotoxic agent.

77. HER3 binding polypeptide, fusion protein or conjugate according to item 76, wherein the cytotoxic agent is selected from the group consisting of auristatin, anthracycline, calicheamycin, combretastatin, doxorubicin, duocarmycin, the CC-1065 anti-tumorantibiotic, ecteinsascidin, geldanamycin, maytansinoid, methotrexate, mycotoxin, taxol, ricin, bouganin, gelonin, pseudomonas exotoxin 38 (PE38), diphtheria toxin (DT), and their analogues, and derivates thereof and combinations thereof.

78. HER3 binding polypeptide, fusion protein or conjugate according to any preceding item further comprising a label.

79. HER3 binding polypeptide, fusion protein or conjugate according to item 78, wherein said label is selected from the group consisting of fluorescent dyes and metals, chromophoric dyes, chemiluminescent compounds and bioluminescent proteins, enzymes, radionuclides and particles.

80. HER3 binding polypeptide, fusion protein or conjugate according to any preceding item, comprising a chelating environment provided by a polyaminopolycarboxylate chelator conjugated to the HER3 binding polypeptide via a thiol group of a cysteine residue or an amine group of a lysine residue.

81. HER3 binding polypeptide, fusion protein or conjugate according to item 80, wherein the polyaminopolycarboxylate chelator is 1,4,7,10-tetraazacyclododecane-1,4,7,10-tetraacetic acid or a derivative thereof.

82. HER3 binding polypeptide, fusion protein or conjugate according to item 81, wherein the 1,4,7,10-tetraazacyclododecane-1,4,7,10-tetraacetic acid derivative is 1,4,7,10-tetraazacyclododecane-1,4,7-tris-acetic acid-10-maleimidoethylacetamide.

83. HER3 binding polypeptide, fusion protein or conjugate according to item 80, wherein the polyaminopolycarboxylate chelator is 1,4,7-triazacyclononane-1,4,7-triacetic acid or a derivative thereof.

84. HER3 binding polypeptide, fusion protein or conjugate according to item 80, wherein the polyaminopolycarboxylate chelator is diethylenetriaminepentaacetic acid or derivatives thereof.

85. HER3 binding polypeptide, fusion protein or conjugate according to any one of items 78-84, comprising a radionuclide suitable for medical imaging, said radionuclide being selected from the group consisting of $^{99m}$Tc, $^{61}$Cu, $^{64}$Cu, $^{66}$Ga, $^{67}$Ga, $^{68}$Ga, $^{110m}$In, $^{111}$In, $^{44}$Sc and $^{86}$Y, or with a radionuclide suitable for therapy, said radionuclide being selected from the group consisting of $^{225}$Ac, $^{212}$Bi, $^{213}$Bi, $^{67}$Cu, $^{166}$Ho, $^{177}$Lu, $^{212}$Pb, $^{149}$Pm, $^{153}$Sm, $^{227}$Th and $^{90}$Y, wherein the radionuclide is complexed with the HER3 binding polypeptide via the chelating environment.

86. HER3 binding polypeptide, fusion protein or conjugate according to item 85, wherein the radionuclide is selected from the group consisting of $^{99m}$Tc, $^{111}$In, $^{64}$Cu and $^{68}$Ga.

87. HER3 binding polypeptide, fusion protein or conjugate according to item 86, wherein the radionuclide is selected from $^{99m}$Tc and $^{111}$In.

88. Composition comprising a HER3 binding polypeptide, fusion protein or conjugate according to any preceding item and at least one pharmaceutically acceptable excipient or carrier.

89. Composition according to item 88, further comprising at least one additional active agent.

90. Composition according to item 89, wherein said at least one additional active agent is a therapeutic agent.

91. Composition according to item 90, wherein said therapeutic agent is selected from the group consisting of immunostimulatory agents, radionuclides, toxic agents, enzymes, factors recruiting effector cells and photosensitizers.

92. HER3 binding polypeptide, fusion protein or conjugate according to any one of items 1-87 or a composition according to any one of items 88-91 for use as a medicament, a diagnostic agent or a prognostic agent.

93. HER3 binding polypeptide, fusion protein, conjugate or composition for use according to item 92, wherein said polypeptide, fusion protein, conjugate or composition modulates HER3 signaling, such as inhibits HER3 signaling.

94. HER3 binding polypeptide, fusion protein, conjugate or composition for use according to item 92 or 93 in the treatment, diagnosis or prognosis of a HER3 related condition.

95. HER3 binding polypeptide, fusion protein, conjugate or composition for use according to item 94, wherein said HER3 related condition is cancer.

96. HER3 binding polypeptide, fusion protein, conjugate or composition for use according to item 95, wherein said cancer is selected from the group consisting of breast cancer, ovarian cancer and prostate cancer.

97. Method of detecting HER3, comprising providing a sample suspected to contain HER3, contacting said sample with a HER3 binding polypeptide, fusion protein or conjugate according to any one of items 1-87 or a composition according to any one of items 88-91, and detecting the binding of the HER3 binding polypeptide, fusion protein, conjugate or composition to indicate the presence of HER3 in the sample.

98. Method for determining the presence of HER3 in a subject, the method comprising the steps:
contacting the subject, or a sample isolated from the subject, with a HER3 binding polypeptide, fusion protein or conjugate according to any one of items 1-87 or a composition according to any one of items 89-91, and
obtaining a value corresponding to the amount of the HER3 binding polypeptide, fusion protein, conjugate or composition that has bound in said subject or to said sample.

99. Method according to item 98, further comprising a step of comparing said value to a reference.

100. Method according to any one of items 97-99, wherein the method is performed in vivo.

101. Method according to any one of items 97-99, wherein the method is performed in vitro.

102. Method of in vivo imaging of the body of a subject having or suspected of having a cancer characterized by over expression of HER3, the method comprising the steps:
administering a radiolabeled polypeptide, fusion polypeptide or conjugate according to any one of items 85-87, wherein the radionuclide is suitable for imaging, into the body of the mammalian subject; and
obtaining one or more images, within 1-72 hours of administration of the radiolabeled polypeptide, of at least a part of the subject's body using a medical imaging instrument, said image(s) indicating the presence of the radionuclide inside the body.

103. Method according to item 98-102, wherein said subject is a mammalian subject, such as a human subject.

104. Method of treatment of a HER3 related condition, comprising administering to a subject in need thereof an effective amount of a HER3 binding polypeptide, fusion protein or conjugate according to any one of items 1-87 or a composition according to any one of items 89-91.

105. Method according to item 104, wherein said HER3 binding polypeptide, fusion protein or conjugate or composition inhibits HER3 signaling.

106. Method according to item 104 or 105, wherein said HER3 related condition is cancer.

107. Method according to item 106, wherein said cancer is selected from the group consisting of breast cancer, ovarian cancer and prostate cancer.

108. Polynucleotide encoding an HER3 binding polypeptide or a fusion protein according to any one of items 1-75.

109. Expression vector comprising a polynucleotide according to item 108.

110. Host cell comprising an expression vector according to item 109.

111. Method of producing a polypeptide according to any one of items 1-75, comprising expressing a polynucleotide according to item 108.

112. Method of producing a polypeptide according to any one of items 1-75, comprising
culturing a host cell according to item 110 under conditions permitting expression of said polypeptide from said expression vector, and
isolating the polypeptide.

The invention claimed is:

1. A HER3 binding polypeptide, comprising a HER3 binding motif (BM), which motif consists of an amino acid sequence selected from SEQ ID NO. 1-35.

2. The HER3 binding polypeptide according to claim 1, selected from SEQ ID NO:71-105.

3. The HER3 binding polypeptide according to claim 1, wherein the off-rate ($k_{off}$) of the interaction between said HER3 binding polypeptide and human HER3 is at least four-fold reduced, when compared to the off-rate ($k_{off}$) of the interaction between a comparative HER3 binding polypeptide comprising the amino acid sequence SEQ ID NO:107 and human HER3, as measured using the same experimental conditions.

4. The HER3 binding polypeptide according to claim 1, wherein the $K_D$ value of the interaction between said HER3 binding polypeptide and human HER3 is at most $1\times10^{-8}$ M.

5. The HER3 binding polypeptide according to claim 1, further comprising a second moiety consisting of a polypeptide having a biological activity.

6. The HER3 binding polypeptide according to claim 5, wherein said biological activity is selected from a group consisting of a therapeutic activity, a binding activity and an enzymatic activity.

7. The HER3 binding polypeptide according to claim 1, further comprising a label, wherein said label is selected from the group consisting of fluorescent dyes and metals, chromophoric dyes, chemiluminescent compounds and bioluminescent proteins, enzymes, radionuclides and particles.

8. The HER3 binding polypeptide of claim 7, further comprising a second moiety comprising a polypeptide having a biological activity.

9. A composition comprising a HER3 binding polypeptide according to claim 1 and at least one excipient or carrier.

10. The composition of claim 9, wherein the HER3 binding polypeptide further comprises a second moiety comprising a label or a polypeptide having a biological activity.

11. The composition of claim 10, wherein the second moiety comprises a label.

12. The composition of claim 10, wherein the second moiety comprises a polypeptide having a biological activity.

13. A polynucleotide encoding an HER3 binding polypeptide according to claim 1.

14. The polynucleotide of claim 13, wherein the HER3 binding polypeptide further comprises a second moiety comprising a polypeptide having a biological activity.

15. A method of detecting HER3, comprising contacting a sample suspected to contain HER3 with a HER3 binding polypeptide according to claim 1, and detecting the binding of the HER3 binding polypeptide to indicate the presence of HER3 in the sample.

16. The method of claim 15, wherein the HER3 binding polypeptide further comprises a second moiety comprising a label or a polypeptide having a biological activity.

17. The method of claim 16, wherein the second moiety is the polypeptide having a biological activity.

18. The method of claim 16, wherein the second moiety is the label.

19. A method of in vivo imaging of the body of a subject having or suspected of having a cancer characterized by over expression of HER3, comprising the steps of:
    administering a radiolabeled HER3 binding polypeptide according to claim 7, wherein the radionuclide is suitable for imaging, into the body of the mammalian subject; and
    obtaining one or more images, within 1-72 hours of administration of the radiolabeled polypeptide, of at least a part of the subject's body using a medical imaging instrument, said image(s) indicating the presence of the radionuclide inside the body.

20. The method of claim 19, wherein the radiolabeled HER3 binding polypeptide further comprises a second moiety comprising a polypeptide having a biological activity.

21. A method of treatment of a HER3-expressing cancer, comprising administering to a subject in need thereof an effective amount of a HER3 binding polypeptide of claim 1.

22. The method of claim 21, wherein the HER3 binding polypeptide further comprises a second moiety comprising a label or a polypeptide having a biological activity.

23. The method of claim 22, wherein the second moiety is the polypeptide having a biological activity.

24. The method of claim 22, wherein the second moiety is the label.

* * * * *

UNITED STATES PATENT AND TRADEMARK OFFICE
CERTIFICATE OF CORRECTION

PATENT NO. : 9,745,350 B2
APPLICATION NO. : 14/431336
DATED : August 29, 2017
INVENTOR(S) : Magdalena Malm, John Löfblom and Stefan Ståhl It is certified that error appears in the above-identified patent and that said Letters Patent is hereby corrected as shown below:

In the Claims

In Claim 4, Line 2, "$1 \times 10^{-8}$ M" should read as --$1 \times 10^{-9}$ M--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*